(12) United States Patent
Gifford et al.

(10) Patent No.: US 11,306,308 B2
(45) Date of Patent: Apr. 19, 2022

US011306308B2

(54) HIGH-THROUGHPUT CRISPR-BASED LIBRARY SCREENING

(71) Applicants: Massachusetts Institute of Technology, Cambridge, MA (US); The Brigham and Women's Hospital, Inc., Boston, MA (US)

(72) Inventors: David K. Gifford, Boston, MA (US); Nisha Rajagopal, Boston, MA (US); Richard Irving Sherwood, Boston, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 261 days.

(21) Appl. No.: 15/775,621

(22) PCT Filed: Nov. 11, 2016

(86) PCT No.: PCT/US2016/061691
§ 371 (c)(1),
(2) Date: May 11, 2018

(87) PCT Pub. No.: WO2017/083766
PCT Pub. Date: May 18, 2017

(65) Prior Publication Data
US 2018/0327740 A1     Nov. 15, 2018

Related U.S. Application Data

(60) Provisional application No. 62/255,359, filed on Nov. 13, 2015.

(51) Int. Cl.
| | | |
|---|---|---|
| *C12N 15/10* | (2006.01) |
| *C12N 9/22* | (2006.01) |
| *C12N 15/11* | (2006.01) |
| *C12N 15/113* | (2010.01) |
| *C12N 15/63* | (2006.01) |
| *C12N 15/79* | (2006.01) |
| *C12N 15/90* | (2006.01) |

(52) U.S. Cl.
CPC .......... *C12N 15/1082* (2013.01); *C12N 9/22* (2013.01); *C12N 15/102* (2013.01); *C12N 15/111* (2013.01); *C12N 15/113* (2013.01); *C12N 15/63* (2013.01); *C12N 15/79* (2013.01); *C12N 15/907* (2013.01); *C12N 2310/20* (2017.05); *C12N 2310/531* (2013.01); *C12N 2800/80* (2013.01)

(58) Field of Classification Search
None
See application file for complete search history.

(56) References Cited

U.S. PATENT DOCUMENTS

| 8,795,965 B2 | 8/2014 | Zhang |
| 2014/0068797 A1* | 3/2014 | Doudna ............. A61P 31/00 800/18 |
| 2015/0143588 A1 | 5/2015 | Sastry-Dent et al. |

OTHER PUBLICATIONS

International Search Report and Written Opinion for PCT/US2016/061691, dated Jan. 26, 2017.
International Preliminary Report on Patentability for PCT/US2016/061691, dated May 24, 2018.
Qi et al., Repurposing CRISPR as an RNA-guided platform for sequence-specific control of gene expression. Cell. Feb. 28, 2013;152(5):1173-83. doi: 10.1016/j.cell.2013.02.022. Erratum in: Cell. Feb. 4, 2021;184(3):844. PMID: 23452860; PMCID: PMC3664290.
Rajagopal et al., High-throughput mapping of regulatory DNA. Nat Biotechnol. Feb. 2016;34(2):167-74. doi: 10.1038/nbt.3468. Epub Jan. 25, 2016. PMID: 26807528; PMCID: PMC5108523.
Zhou et al., High-throughput screening of a CRISPR/Cas9 library for functional genomics in human cells. Nature. May 22, 2014;509(7501):487-91. doi: 10.1038/nature13166. Epub Apr. 9, 2014. PMID: 24717434.

\* cited by examiner

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

Provided herein is an improved method for performing CRISPR/Cas based screening that is not dependent on viral cloning methods.

14 Claims, 20 Drawing Sheets

Specification includes a Sequence Listing.

HIGH-THROUGHPUT CRISPR-BASED LIBRARY SCREENING

RELATED APPLICATIONS

This application is a national stage filing under 35 U.S.C. § 371 of International Application No. PCT/US2016/061691, filed Nov. 11, 2016, which was published under PCT Article 21(2) in English and claims the benefit under 35 U.S.C. § 119(e) of U.S. Provisional Application Ser. No. 62/255,359 entitled "HIGH-THROUGHPUT CRISPR-BASED SCREENING" filed on Nov. 13, 2015, the entire contents of each of which are incorporated by reference herein.

FEDERALLY SPONSORED RESEARCH

This invention was made with Government support under Grant Nos. R01 HG008754, U01 HG007037 and K01 DK101684 awarded by the National Institutes of Health. The Government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 7, 2020, is named M065670371US01-SEQ-MAT and is 55.7 kilobytes in size.

BACKGROUND

Gene regulation provides the basis for cell type-specific function, and differences in cis-regulatory DNA underlie human variation, disease, and cancer. Our rudimentary understanding of gene regulation impairs our ability to predict the effects of cis-regulatory variants on gene expression and to predictively alter gene expression during stem cell differentiation and reprogramming.

Strides have been made over the last decade to catalogue gene regulatory elements. A histone modification code has been found to correlate with cis-regulatory elements such as enhancers and promoters and states such as active and poised[1-5]. Gene expression reporter assays, which can now be done in high-throughput[6-8], have confirmed elements that are sufficient to activate gene expression in heterologous contexts. Additionally, techniques to identify distal DNA interactions have begun to associate enhancers with their cognate promoters[9-12], which are often not in close proximity and can at times be megabases apart.

However, existing gene regulatory techniques have several shortcomings. Reporter assays, by focusing on elements that are sufficient to activate gene expression in a heterologous context, cannot characterize elements that are necessary but not sufficient for gene expression or elements whose activity does not transfer to a non-native context. Additionally, genes can have dozens of regulatory elements, and there is no high-throughput approach capable of determining the relative importance of each gene regulatory element on native gene expression levels.

SUMMARY

This disclosure provides, inter alia, methods for studying the function of genomic regions, as well as methods for identifying genomic regions and elements involved in transcription regulation. These methods rely in part on a newly developed CRISPR/Cas system-based library screen provided herein. This disclosure therefore also provides an improved method for performing CRISPR/Cas system-based library screens.

The method exploits the ability of the CRISPR/Cas system to cleave specific genomic sites in order to introduce exogenous guide sequences of interest into the cell and then to allow such exogenous sequences to target the CRISPR/Cas system to homologous genomic sites in the cell. The targeted genomic sequences are then mutated in the host cell, and the effect of such mutation is analyzed. As is known in the art, CRISPR/Cas system nucleases require a guide RNA to cleave genomic DNA. These guide RNAs are composed of (1) a 19-21 nucleotide spacer (guide) of variable sequence that targets the CRISPR/Cas system nuclease to a genomic location in a sequence-specific manner, and (2) an invariant hairpin sequence that is constant between guide RNAs and allows the guide RNA to bind to the CRISPR/Cas system nuclease.

The methods provided herein involve a first step of integrating one or more DNA sequences that each code for a dummy guide RNA, into the genome of a cell, at one or more typically defined loci. This step comprises integrating a defined (or controlled) number of such DNA sequences into the cell. The integration occurs at a defined (or controlled) number of loci in the cell. In some instances, the number of DNA sequences and loci will be known to the end user. There may be 1, 2, 3, 4, 5, 6, 7, 8, 9, 10 or more such DNA sequences integrated into the genome of the cell, and such DNA sequences may be integrated in proximity to each other or distally to each other. When a host cell has more than one dummy guide RNA construct integrated, such dummy guide RNA constructs may be identical to each other (i.e., their sequences may be identical) or they may differ from each other (i.e., their sequences may be different).

The "variable" or guide sequence of the dummy guide RNA is not homologous to any sequence in the host cell and thus it is not able to direct a CRISPR/Cas nuclease to any particular site in the genome. Thus the presence and/or expression of the dummy guide RNA, whether in the presence or absence of a CRISPR/Cas nuclease, does not trigger a CRISPR/Cas-based genomic cleavage event in the cell. Accordingly, such dummy guide RNA is referred to as defective.

The second step introduces into the host cell a library of DNA fragments that each comprises a candidate variable/guide sequence. The variable/guide sequences in these DNA fragments may be derived from genomic DNA of the cell type being used as the host cell. These fragments may be prepared through fragmentation of genomic DNA, optionally followed by amplification using any number of amplification techniques, including but not limited to PCR. Through the amplification process, the genomic fragments may be modified to facilitate their integration into the dummy RNA genomic locus. For example, the genomic fragments may have additional sequences added to one and typically both ends during amplification. These end sequences may be homologous to sequences that flank the variable/guide sequence at the integrated dummy guide RNA construct. Using a CRISPR/Cas system nuclease such as Cas9, the variable/guide sequence of the dummy guide RNA construct is cleaved and, through a process of homologous recombination, is replaced with the variable/guide sequence in one of the amplified fragments to form a new guide RNA construct or locus. The new guide RNA that is encoded by the recombined locus is homologous to a genomic region in the cell, and it is thus able to direct a CRISPR/Cas nuclease to that specific genomic region in the cell, thereby facilitating cleavage of that region by the CRISPR/Cas nuclease. Accordingly, the newly formed guide RNA locus or construct is referred to as a functional guide RNA locus or construct, and the guide RNA encoded by such locus is referred to herein as a functional guide RNA. When the dummy guide RNA constructs are converted to functional guide RNA constructs, such functional guide RNA constructs are more likely to be different from each other, particularly if the library of DNA fragments introduced into the host cell is complex (i.e., has low redundancy).

As will be understood, the number of integrated DNA sequences that each encode a dummy guide RNA is controlled by the end user. In turn, in these embodiments, the cell can only have as many functional guide RNAs as it has integrated DNA sequences that encode the dummy guide RNAs.

All other CRISPR library screens to date have relied upon molecular cloning of the variable/spacer/guide sequences, typically into lentiviral vectors, to achieve libraries of thousands of distinct guide RNAs. This process has proven difficult and laborious. The methods provided herein eliminate the molecular cloning step. Importantly, these methods intrinsically control the number of functional guide RNAs encoded in a cell. The Examples demonstrate the use of these methods in a high-throughput CRISPR/Cas-based library screen.

The foregoing methods can be used to screen for the effect of mutations anywhere in the genome provided a suitable readout is apparent. The mutations that can be studied include mismatch mutations of single or multiple nucleotides such as but not limited to single nucleotide polymorphisms as well as deletions of one or more nucleotides including deletions of genomic regions spanning tens, hundreds, thousands, or more nucleotides. The former can arise if a single cleavage event occurs at a locus. The latter can arise if two relatively proximal guide RNAs are used together to cleave relatively proximal sequences, with the end result being that genomic sequence between the cleavage sites is deleted from the genome.

In some instances, the method further comprises analyzing the effect of the mutation(s) in a defined region. Such regions include for example a regulatory region in the vicinity of the coding region of interest. The expression of the gene (coding sequence) of interest or the expression or functional activity of its gene product (encoded protein) may be used as the readout of the effect of the mutation. Alternatively, a coding sequence for a reporter gene may be inserted into the genome (e.g., in place of the native coding sequence) and its expression or the functional activity of its gene product may be used as the readout. In some instances, the coding sequence of a reporter gene is fused to the native coding sequence, and the readout is the mRNA or protein expression of the resultant fusion protein or the functional activity of the fusion protein. The method can be used to screen and identify sequences involved in cellular processes other than transcription, including for example cell division, cell metabolism, etc. The method can be used to identify mutations that result in loss of function or gain of function, or decrease or increase of transcription. The method may be used to identify the effect of one or more mutations simultaneously. The method may be used to identify the effect of mutations in two or more genes, including two or more regulatory regions, two or more coding sequences, or some combination thereof.

As an example, a population of cells is transfected with a library of DNA fragments each encoding the variable sequence of a guide RNA along with sufficient flanking DNA to enable homologous recombination of the fragment at the dummy guide RNA locus, the DNA fragments are integrated into the dummy guide RNA loci, the functional guide RNAs are expressed in the cells, and in the presence of CRISPR/Cas the functional guide RNAs induce DNA mutations in the cell. The RNA profile and transcriptome of each cell may be analyzed using techniques such as but not limited to single-cell RNA-seq technology. The analysis will reveal the consequence(s) of the genomic mutation on the RNA profile of the cell including the type and abundance of RNA molecules. The method can also be used to identify the nature (e.g., sequence) of the guide RNA that effected the DNA mutation in the first instance. Thus, the effect of a mutation can be observed on the entire cellular transcriptome at once by performing the experiment in a single cell.

In one particular aspect, also provided herein is a method for identifying and elucidating the function of non-coding genomic DNA regions. This method typically inserts a coding sequence for a reporter protein at a genomic locus of interest, and uses the reporter protein as the readout. The resultant locus comprises the coding sequence for a reporter protein (such as for example a fluorescent reporter protein) under the control of regulatory elements of the genomic locus of interest. A CRISPR/Cas system-based library screen is performed in which the genomic region surrounding the reporter coding sequence is "blanketed" with functional guide RNAs which induce a single mutation in each cell at one position. Regulatory regions of interest are then identified as those which result in loss of signal from the reporter protein when mutated. This method takes advantage of the random nature of CRISPR/Cas system mutation. Once such regions of interest are identified, they may be further analyzed using deep sequencing in order to identify the mutation(s) at nucleotide resolution. Analysis of a plurality of cells having altered reporter function (e.g., fluorescence) compared to control (including reduced, absent or enhanced reporter function (e.g., fluorescence)) can be further performed to identify genomic regions that are important in regulation of the reporter coding sequence and thus the native locus of interest. This approach can be used to further our understanding of non-coding DNA regions such as GWAS-identified non-coding SNPs.

Thus, provided herein is a defective CRISPR/Cas "guide RNA" construct comprising a guide sequence that is not homologous to a eukaryotic genome, and a guide hairpin sequence, operably linked to a promoter. In some embodiments, the guide sequence has less than 100% homology to a eukaryotic genome. In some embodiments, the guide sequence has less than 90%, less than 80%, less than 70%, less than 60%, less than 50%, less than 40%, less than 30%, less than 20%, less than 10%, or less than 5% homology to the eukaryotic genome. The guide sequence is sufficiently non-homologous to not trigger a CRISPR/Cas-mediated cleavage event in the eukaryotic genome.

The eukaryotic genome may be a human genome, and thus the defective CRISPR/Cas guide construct may be intended for use in human cells.

The guide sequence may be 19-21 nucleotides in length. The hairpin sequence may be less than 100 nucleotides, less than 80 nucleotides, less than 60 nucleotides, or about 40 nucleotides in length. In other embodiments, the hairpin sequence may be about 20-60 nucleotides in length. Once transcribed, the hairpin sequence can be bound to a CRISPR/Cas nuclease.

The defective CRISPR/Cas guide construct is DNA in nature and when transcribed produces a defective guide RNA.

The construct may be isolated, and thus provided as a single nucleic acid molecule or it may be integrated into the genome of a host cell (i.e., a host cell genome).

Thus, also provided herein is a host cell having integrated into its genome one or more of any of the preceding defective CRISPR/Cas guide constructs. In some embodiments, a single defective CRISPR/Cas guide construct is integrated into the host cell genome. In some embodiments, 2-10 defective CRISPR/Cas guide constructs are integrated into the host cell genome.

Also provided is a population of cells comprising any of the preceding host cells. The population of host cells may be homogeneous or heterogeneous.

Thus, also provided is a cell comprising a CRISPR/Cas dummy guide RNA construct, integrated into the cell genome and comprising a guide sequence that is not homologous to native genomic sequence in the cell.

In some embodiments, the cell comprises a single CRISPR/Cas dummy guide RNA construct. In some embodiments, the cell comprises a coding sequence for a reporter protein or a fusion protein comprising a reporter protein, integrated into the genome.

In some embodiments, the cell further comprises a CRISPR/Cas nuclease and/or a coding sequence for the CRISPR/Cas nuclease. In some embodiments, the cell further comprises a Cas9 nuclease and/or a coding sequence for Cas9 nuclease.

In some embodiments, the cell further comprises a dummy guide RNA sequence that directs a CRISPR-Cas nuclease to the integrated non-homologous guide sequence.

In some embodiments, the cell further comprises a plurality of exogenous DNA fragments, each comprising nucleotide sequences homologous to a native genomic sequence in the cell and to the integrated CRISPR/Cas dummy guide RNA construct. In some embodiments, the exogenous DNA fragments comprise nucleotide sequence from a regulatory region upstream or downstream of a coding sequence of interest. The coding sequence of interest may be coding sequence for a reporter protein or a fusion protein comprising a reporter protein.

Also provided is a cell comprising a CRISPR/Cas functional guide RNA construct, integrated into the cell genome at a defined location, wherein the functional guide RNA construct comprises a guide sequence that is homologous to native genomic sequence in the cell. In some embodiments, the cell comprises more than one CRISPR/Cas functional guide RNA constructs, each integrated into the cell genome at a defined location. In some embodiments, the more than one CRISPR/Cas guide RNA constructs within a single cell comprise different variable guide sequences.

Also provided is a host cell having integrated into its genome a single functional guide RNA construct, in a virus-independent manner.

Also provided is a host cell comprising a plurality of linear, amplified non-integrated DNA fragments, each fragment comprising a CRISPR/Cas variable guide sequence that is homologous to an endogenous (or native) genomic sequence in the host cell and an invariant hairpin sequence that when transcribed is capable of binding a CRISPR/Cas nuclease, wherein the amplified non-integrated DNA fragments are not in a viral vector.

In some embodiments, the host cell has integrated into its genome a coding sequence for a reporter protein or a fusion protein comprising a reporter protein.

Also provided is a method comprising (1) introducing, into a host cell comprising a dummy guide RNA construct, a pool of linear, amplified DNA fragments each comprising a CRISPR/Cas variable guide sequence homologous to a genomic sequence in the cell, and (2) allowing a single linear, amplified DNA fragments to homologously recombine with the dummy guide RNA construct in the presence of a CRISPR/Cas nuclease to form a genomically integrated functional guide RNA construct, wherein the host cell comprises a reporter protein coding sequence integrated into its genome and the linear, amplified DNA fragments are derived from the regulatory region of the reporter protein coding sequence.

In some embodiments, the method further comprises expressing the functional guide RNA that targets a genomic sequence in the host cell, introducing a mutation in the targeted genomic sequence in the presence of a CRISPR/Cas nuclease, and determining the effect of the mutation on the expression of a reporter protein coding sequence.

In some embodiments, the reporter protein coding sequence is a coding sequence of a fusion protein comprising a reporter protein.

In some embodiments, the effect of the mutation is an increase or a decrease in the expression of the reporter protein coding sequence.

In some embodiments, the host cell is in a host cell population and each host cell independently forms a unique functional guide RNA construct.

In some embodiments, each host cell expresses a unique functional guide RNA and is mutated in a different genomic sequence relative to other host cells in the population.

These and other aspects and embodiments of the invention will be described in greater detail herein.

BRIEF DESCRIPTION OF DRAWINGS

FIG. 1A. In MERA, a genomically integrated dummy gRNA is replaced with a pooled library of gRNAs through CRISPR/Cas9-based homologous recombination such that each cell receives a single gRNA. gRNAs are tiled across the cis-regulatory regions of a GFP-tagged gene locus, and cells are flow cytometrically sorted according to their GFP expression levels. Deep sequencing on each population is used to identify gRNAs preferentially associated with partial or complete loss of gene expression. FIG. 1B. $Zfp42^{GFP}$ mESCs express uniformly strong GFP. After bulk gRNA integration, a subpopulation of cells lose partial or complete GFP expression. These cells are flow cytometrically isolated for deep sequencing. FIGS. 1C and 1D. Bulk reads for gRNAs are highly correlated between replicates of Tdfg1 (FIG. 1C) or Zfp42 (FIG. 1D), indicating consistent and replicable integration rates.

FIG. 2A. A genomic view the Tdgf1 proximal regulatory region showing in track order (i) the location of gRNAs that did not result in GFP loss, (i) enriched gRNAs in $GFP^{neg}$ cells (dark grey), (iii) enriched gRNAs in $GFP^{medium}$ cells (light grey), (iv) annotated genes, (v) predicted enhancers (light grey=weak, dark grey=strong), (vi) DNase-I hotspot regions, (vii) transcription factor binding density based on ChIP-seq data, (vii) H3K4me3 ChIP-seq data. Several active regulatory elements coincide with dense clusters of overlapping gRNAs. A large number of gRNA significantly enriched in $GFP^{neg}$ population are also observed in regions devoid of regulatory element features (UREs). FIG. 2B.

Individual validation of specific gRNAs detected as enriched in the GFP$^{neg}$ population in the MERA assay using the self-cloning CRISPR system. The proportion of cells undergoing GFP loss upon incorporation of a particular gRNA divided by the proportion of cells undergoing GFP loss upon incorporation of GFP-targeting positive control gRNA are plotted against the actual genomic location of the gRNA. Negative controls or gRNA showing no reads in either GFP$^{neg}$ and GFP$^{medium}$ populations are highlighted. FIG. 2C. Correlation of gRNAs significantly enriched in the GFP$^{neg}$ population in fixed size bins varying from 100 bp to 1 kb for biological replicates in Tdgf1. FIG. 2D. Fraction of GFP$^{neg}$ enriched gRNA among the different functional genomic categories surrounding the Tdgf1 gene.

FIG. 3A. A genomic view the Zfp42 proximal regulatory region showing in track order (i) the location of gRNAs that did not result in GFP loss, (i) enriched gRNAs in GFP$^{neg}$ cells (dark grey), (iii) enriched gRNAs in GFP$^{medium}$ cells (light grey), (iv) annotated genes, (v) predicted enhancers (light grey=weak, dark grey=strong), (vi) DNase-I hotspot regions, (vii) transcription factor binding density based on ChIP-seq data, (vii) H3K4me3 ChIP-seq data. Several active regulatory elements coincide with dense clusters of overlapping gRNAs. FIG. 3B. Correlation of gRNAs significantly enriched in the GFP$^{neg}$ population in fixed size bins varying from 100 bp to 1 kb for biological replicates in Tdgf1. FIG. 3C. Fraction of GFP$^{neg}$ enriched gRNA among the different functional genomic categories surrounding the Tdgf1 gene.

FIG. 4A. A schematic of the procedure involved in finding mutations induced by a particular gRNA. FIG. 4B. Two gRNAs at a proximal Tdgf1 enhancer region in the genomic context showing its overlap with DNAse-I hotspot and predicted enhancer regions, and transcription factor binding sites Stat3, Tcfcp2l1 and Sox2. FIG. 4C. ROC curve for 5-fold classification of GFP$^{neg}$ and GFP$^{pos}$ genotypes using mutations within −20 to +20 bp of the gRNA along left and right paired end reads as features. FIG. 4D. Motif logo for region mutated by gRNAs with base scores computed as log-ratios of the Hellinger distance of the GFP$^{neg}$ genotypes at a base to the reference base to the Hellinger distance of the GFP$^{pos}$ genotypes at a base to the reference base, caused by Tdgf_gRNA_1 and Tdgf_gRNA_2 along the left paired end read.

FIG. 5A. Two gRNAs in the genomic context showing their absence of active histone modifications, known transcription factor binding, predicted enhancers or DNAse-I hotspots. FIG. 5B. ROC curve for 5-fold classification of GFP$^{neg}$ and GFP$^{pos}$ genotypes using mutations on the right paired end read within −20 to +20 bp of Tdgf_URE_ gRNA2. Unweighted classification (dark grey) counts each unique genotype in the test-set only once while weighted classification (light grey) counts each unique genotype in the test-set as many times as the number of reads assigned to it, for calculating sensitivity and specificity. FIG. 5C. Fraction of unique genotypes in GFP$^{neg}$ (black plot) and GFP$^{pos}$ (grey plot) populations with mutations at bases along the right paired end read reveals pattern of cleavage around Tdgf_URE_gRNA2. FIG. 5D. Motif logo for the region mutated by Tdgf_URE_gRNA2 along the right paired end read with base scores computed as log-ratios of the hellinger distance of the GFP$^{neg}$ genotypes at a base to the reference base to the Hellinger distance of the GFP$^{pos}$ genotypes at a base to the reference base.

FIG. 6A. Tdgf1 MERA screen ratio of GFP$^{medium/neg}$/bulk reads for each gRNA at an upstream enhancer (left) and a downstream URE (right) region. FIG. 6B. Flow cytometric measurement of Tdgf1-GFP expression in clonal cell lines following CRISPR-induced deletion of the shaded regions from (FIG. 6A) show loss of GFP (plots on top panel). CRISPR-mediated homology-directed repair (HDR) back to the wildtype genotype induced robust GFP recovery at both loci (plots on bottom panel). FIG. 6C. Tdgf1 RNA expression in wildtype mESCs (left), clonal mESC lines with deletions of the enhancer and URE shaded in (FIG. 6A) (top panel in FIG. 6B), and bulk mESC lines following HDR back to the wildtype genotype (bottom panel in FIG. 6B), all normalized to wildtype expression level.

DETAILED DESCRIPTION

Figure 1A:
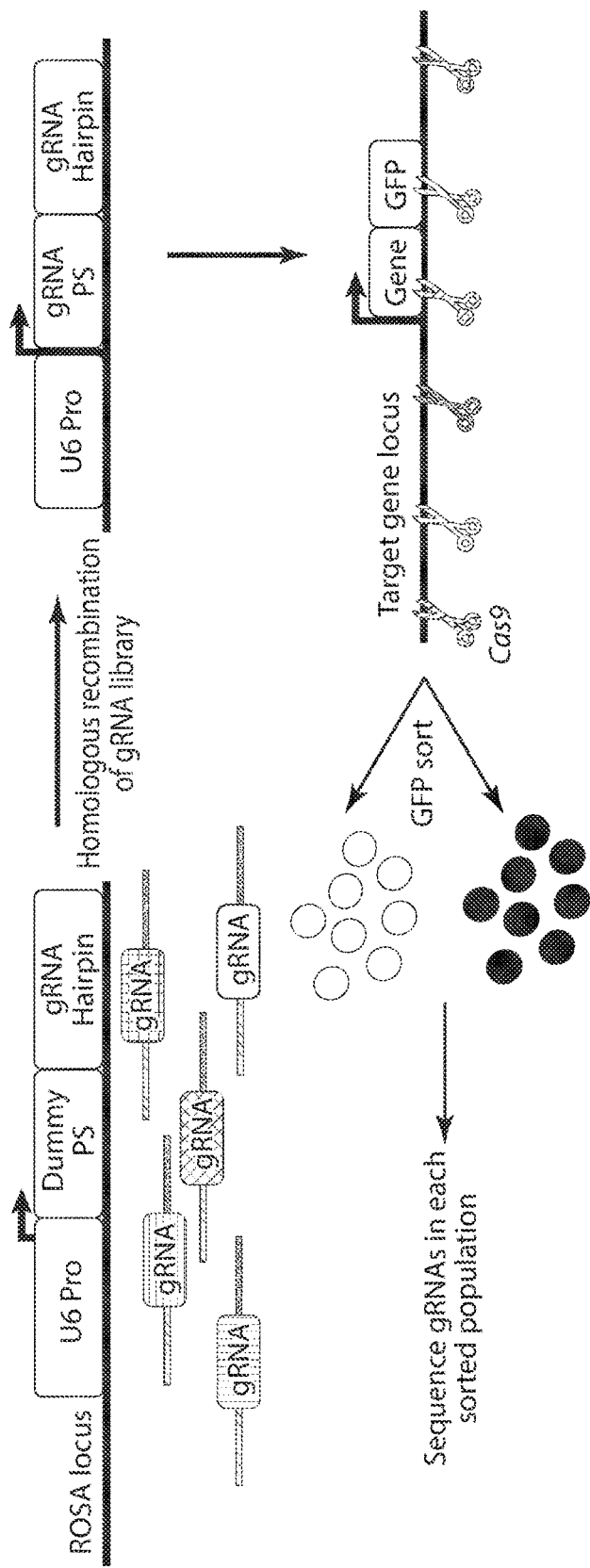
FIGS. 1A-1D. Multiplexed Editing Regulatory Assay (MERA).

The invention provides an improved CRISPR/Cas based library screening method. The method does not rely on cloning of guide RNAs into host cells, as is common in prior art methods. Rather, the methods provided herein employ a host cell that harbors one or more dummy guide RNA constructs integrated in its genome. These dummy guide RNA constructs serve as "landing pads" for exogenous variable/spacer/guide sequences introduced into the cell. In the presence of a CRISP/Cas nuclease, such as Cas9, and a dummy guide RNA (having homology to the dummy guide RNA construct), the dummy guide RNA construct is cleaved. In the process of repairing the cleaved site, a single exogenous variable/spacer/guide sequence is introduced into the site through homologous recombination.

The dummy guide RNA construct also serves as a gate keeper. It does so because there will be a 1:1 ratio of dummy to functional guide RNA constructs in the cell following the homologous recombination event. Thus, if the cell harbors one dummy guide RNA construct, it will harbor one functional guide RNA construct; if it harbors two dummy guide RNA constructs, it will harbor two functional guide RNA constructs, and so on.

The screening method has been used to analyze regulatory regions within the genome (i.e., the regulatory genome). Its utility however is not so limited and it can be used to study coding as well as non-coding regions of the genome. The readouts may include a reduction (or an elimination) or an enhancement of gene expression. Moreover, by combining the screening methodology with deep sequencing methods, the regulatory genome can be analyzed at single base resolution.

The method can be used to screen a plurality (e.g., thousands) of sequences in the genome, thereby elucidating the function of such sequences. The method may be used to target mutations in a region of interest (e.g., a region of a chromosome, or region around a gene of interest) or it may be used more broadly. If the mutations are targeted to a gene of interest, then the mutation may be studied by its effect on a coding region of interest or by its effect on a reporter gene that is introduced at or near the site of the coding region of interest. The Examples illustrate methods in which the gene of interest is replaced by or fused to a reporter gene in the form of a fluorescent protein. It should be apparent however that the screening method is not so limited and can be used to introduce mutation in virtually any region of a genome and study the effect of such mutation, thereby elucidating the function of that region of the genome.

If the screen is intended to identify regulatory elements of a particular gene of interest, then this may be accomplished, for example, by creating a library of guide sequences that map to and cover the region of interest. If the guide sequences are contiguous or overlapping, then they may be referred to as "tiled" sequences. The screen can identify regulatory regions of a gene of interest through changes in the expression of the gene (or of a reporter gene inserted at that site, or of a fusion protein of the gene of interest and the reporter gene) as a function of the particular guide RNA harbored and expressed by the cell.

CRISPR/Cas9 Mechanism of Action and Library Screening Rationale

The screening method utilizes the CRISPR/Cas system. Cas9 is a nuclease from the microbial type II CRISPR (clustered regularly interspaced short palindromic repeats) system, which has been shown to cleave DNA when paired with a single-guide RNA (gRNA)[13-16]. The gRNA contains a 17-21 bp sequence that directs Cas9 to complementary regions in the genome, thus enabling site-specific creation of double-strand breaks (DSBs) that are repaired in an error-prone fashion by cellular non-homologous end joining (NHEJ) machinery[14, 15, 17]. Cas9 primarily cleaves genomic sites at which the gRNA sequence is followed by a PAM sequence (–NGG)[18-20], which means that on average ⅛ of all genomic bases can be targeted for Cas9 cleavage, although recent reports have identified Cas9 variants that target distinct PAM sequences which would expand the number of available sites for targeting[21]. NHEJ-mediated repair of Cas9-induced DSBs induces a wide range of mutations initiated at the cleavage site which are typically small (<10 bp) insertion/deletions (indels) but can include larger (>100 bp) indels[14, 15, 22] and altered individual bases.

Multiplexed Editing Regulatory Assay (MERA)

The screening method described herein may be extended further. An example of such a further extension of this method, referred to as Multiplexed Editing Regulatory Assay (MERA), is described below and in the Examples. The MERA assay has three phases. The first phase is a high-throughput screen that maps necessary genomic elements. This phase is the screening method described above. The second phase functional motif discovery which characterizes regulatory elements identified in the screen. This is accomplished using deep sequencing in and around the region comprising the guide RNA induced mutation in cells or clones having or lacking a phenotype of interest. The third phase is validation of regulatory elements of interest for example by the replacement of selected genomic elements by homologous recombination.

CRISPR/Cas9 has been used in genome-wide mutation screens to identify genes required for survival, drug resistance, and tumor metastasis[23-27] In these screens, gRNAs targeting tens of thousands of sites within genes are cloned into lentiviral vectors and delivered as a pool into target cells along with Cas9. By identifying gRNAs that are enriched or depleted in the cells after selection for the desired phenotype, genes that are required for this phenotype can be systematically identified.

There are at least two distinctions between MERA and previous gene mutation screening approaches. One distinction relates to the observation that the targeted sites are often close together, so cells receiving more than one gRNA may delete a region instead of mutate that region, a phenomenon that would complicate downstream analysis. This issue can be addressed for lentiviral libraries of the prior art by lowering the multiplicity of infection (MOI). The methods provided herein avoid this by limiting the number of guide RNAs in a single cell, typically having only a single guide RNA per cell. Another distinction relates to the fact that a different guide RNA library is required for each gene of interest. All high-throughput CRISPR/Cas9-based approaches to date required cloning of the gRNA libraries into lentiviral vectors and production of library-specific virus. The methods provided herein do not involve cloning and virus production. Instead, the library of the present methods is a library of DNA fragments generated from a region of interest, and optionally amplified and end-modified to facilitate homologous recombination with the dummy RNA locus. The library can be generated and modified more rapidly and used with greater ease as compared to the cloning-based libraries of the prior art.

To enable the efficient targeting of precisely one regulatory element per cell, a strategy was devised to ensure only one (or in some instances a defined or known number of) gRNA can be expressed per cell and that allows gRNA libraries to be used without any molecular cloning into a delivery vector. The Examples demonstrate a system designed with a single copy of a gRNA expression construct integrated into the universally accessible ROSA locus of mESCs using CRISPR/Cas-mediated homologous recombination (FIG. 1A). The construct comprises a U6 promoter driving expression of a dummy guide RNA. CRISPR/Cas-mediated homologous recombination is then used to replace the dummy guide RNA with a functional guide RNA from a library. In the working examples provided herein, an amplification reaction such as PCR was used to add 79-90 bp homology arms to the guide RNA library, since it was found that longer homology arms increase background cutting of unintegrated guide RNA amplified fragments (data not shown) thereby eliminating such unintegrated fragments. The pool of amplified gRNA fragments was then introduced into cells along with a CRISP/Cas system nuclease such as Cas9 and a guide RNA plasmid that induces a DSB in the dummy guide RNA construct. In a substantial fraction of cells (~30%), the dummy guide RNA construct is repaired by homologous recombination, creating a functional gRNA expression construct targeting a single genomic site from the library (data not shown). It is random which gRNA is integrated in each cell, allowing a pooled screen in which each cell expresses only one gRNA. Of note, the genomic integration-based gRNA screening platform used in MERA could also be applied to other CRISPR-based high-throughput screens as long as the cell line undergoes homologous recombination at appreciable frequency, and it can be modified to achieve expression of any set number of gRNAs per cell for combinatorial screening. While the integration-based approach is thus ill-suited to in vivo screens or screens in cells with limited homologous recombination, it provides an alternative to lentiviral screening that substantially reduces the time, effort, and cost involved in CRISPR-based library screening for applicable cell lines such as ESCs.

Embodiments in which the cell comprises more than one dummy gRNA can be used for a number of applications, including but not limited to combinatorial screening. In some instances, this approach could be used to determine the effect of two or more mutations, either within the same locus or at different genomic loci (e.g., in the same coding sequence, in regulatory regions that control expression of the same coding sequence, etc.), thereby providing insight into how genes or regulatory elements contribute to the phenotype of interest, alone or in combination. As an example, the effect of various combinations of disease-causing SNPs on disease phenotype may be determined. As used herein, a gene refers to coding sequence of a protein and the regulatory regions that control the expression of such coding sequence. The regulatory regions may exist within kilobases or megabases of the coding sequence, and may occur in intronic regions as well.

Figure 1B:
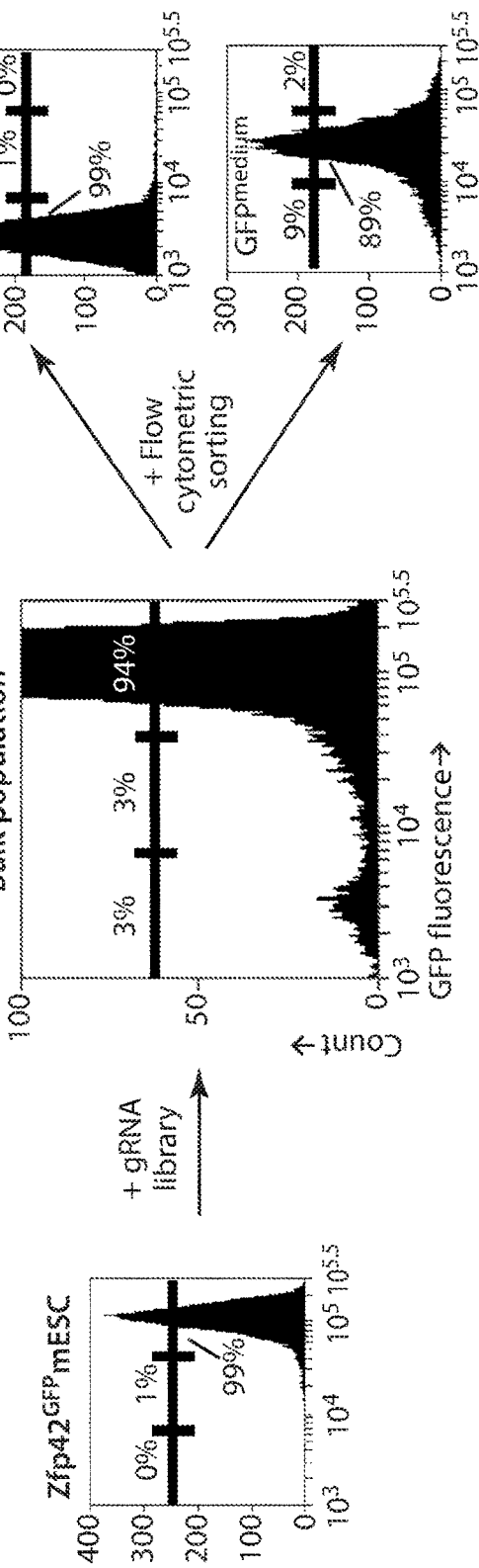

The host cell may be further modified to express a reporter protein, for example under the control of a regulatory region that is being analyzed using the methods described herein. The coding sequence for the reporter protein can be introduced through a CRISPR-mediated knock-in transgene insertion that uses PCR-amplified homology arms. (Arbab et al. Stem Cell Reports, 2015.) This process avoids the time-consuming step of cloning homology arm vectors as is required in prior art methods. As described in the Examples, this procedure was used to construct GFP knock-in alleles at four genes with mESC-specific expression, Nanog, Rpp25, Tdgf1, and Zfp42. As a proof of principle, mESC-specific genes were chosen because the networks of mESC gene regulation and the epigenetic state of mESC regulatory elements are among the best understood of any cell type[29, 30]. Two of the genes (Nanog and Rpp25) were constructed as C-terminal GFP fusion proteins, and two (Tdgf1 and Zfp42) had their open reading frames replaced with GFP to compare these two approaches. All knock-in lines, upon clonal selection, had robust GFP expression, although GFP levels were highest in Tdgf1$^{GFP}$ and Zfp42$^{GFP}$ lines (FIG. 1B, data not shown). The Nanog$^{GFP}$ line always contained ~20% GFP$^{neg}$ cells, presumably due to known heterogeneous Nanog expression in mESCs (data not shown)[31].

Four gRNA libraries were constructed, each with 3908 gRNAs tiling cis-regulatory regions of Nanog, Rpp25, Tdgf1, and Zfp42. In the case of Tdgf1, the library targeted the 40 kb region proximal to the gene (coding sequence) in an unbiased manner. In other cases, the regions selected were regions proximal to the gene most likely to be involved in regulation based on enhancer-like features that are a maximum of ~150 kb away from the coding sequence. Additionally, distal regions up to 92 mB away from the gene were added when ChIA-PET distal interaction data[9] suggested a possible interaction with the target gene promoter using the Sprout algorithm[35]. In FIGS. 2A-D and 3A-C, the bulk density panel shows the distribution of integrated guide RNAs along the region probed. Among the 3621 gRNAs found to be integrated in at least 1 replicate of Tdgf1, 99% were within 140 bp of the nearest adjacent gRNA and 95% were within 32 bp of the adjacent gRNA. Distances were measured between the mid-points of adjacent gRNAs. The mean distance between adjacent gRNAs was 11 bp, and the standard deviation of this distance was 32 bp. Of note, repetitive and unmappable genomic regions cannot be tiled with gRNAs, and gRNAs targeting regions whose sequence differs from that of the reference genome cannot be appropriately tiled without genome sequence data of the cell line. Each library also contained 10 positive control gRNAs targeting the GFP open reading frame that we expected would cause GFP loss.

Screening Method Generally

The screening methods described herein utilize a population of genetically modified host cells, and a library (or pool) of linear DNA fragments that comprise a guide sequence homologous to a region of interest in the genome of the host cell. In some instances, the guide sequence is at least 90% or at least 95% homologous to a region of interest. In other instances, the guide sequence is 100% homologous to the region of interest. The starting host cell population is homogeneous: all the cells have one or a controlled and/or defined number of dummy (or defective) guide RNA (gRNA) loci integrated into their genome. As will be understood in the context of this disclosure, a gRNA locus integrated into a cell genome is a DNA that encodes for the gRNA, whether that gRNA is a dummy (or defective) gRNA or a functional gRNA. Cells in a homogenous population will comprise the same gRNA locus or loci. In some instances, all the cells also carry a coding sequence for a reporter protein (reporter gene) or a coding sequence for a fusion of a reporter protein and a protein native to the cell. In addition to their guide sequences, the DNA fragments also comprise sequence homologous to the dummy guide RNA locus. These homologous sequences facilitate homologous recombination of the DNA fragment and the dummy guide RNA locus.

The library of linear DNA fragments is introduced into individual cells in the population. The fragments may be introduced in any number of ways including but not limited to electroporation. Importantly the DNA fragments are not introduced via viral vectors and nor are the DNA fragments provided in the context of viral vectors. Accordingly, the length of such fragments may be 500 nucleotides or less, 400 nucleotides or less, 300 nucleotides or less, 200 nucleotides or less, 100 nucleotides or less, or 50 nucleotides or less in length. The cells then integrate into their genomes one or a controlled (and typically known) number of the fragments. The number of fragments integrated is dictated by the number of dummy guide RNA loci in the genome. Each cell will integrate a fragment independently of other cells.

Also introduced into the cells are a CRISPR/Cas nuclease or a construct that encodes such nuclease and a guide RNA or a construct that encodes such a guide RNA that binds to the dummy guide RNA construct and thereby facilitates cleavage of the construct by the CRISPR/Cas nuclease. The cell is therefore able to produce the nuclease and also to express a guide RNA that targets the dummy guide RNA locus. This results in cleavage of the dummy guide RNA locus by the nuclease, an event that initiates homologous recombination of the dummy guide RNA locus and the DNA fragment via their regions of homology. The resultant locus encodes a functional guide RNA that targets a genomic region, in contrast to the parent dummy guide RNA locus.

The library of DNA fragments is therefore used to generate a library of cells. In some embodiments, each cell is capable of expressing a single CRISPR/Cas guide RNA. In some embodiments, each cell is capable of expressing a controlled number of different CRISPR/Cas guide RNA.

The screening process is then initiated by separating cells that differ in the phenotype of interest, for example by flow cytometric separation of GFP+ and GFP– cells. Alternately, single cell RNA-seq can be performed on all cells without prior selection.

Deletion of Genomic DNA Regions

In another embodiment, defined regions (or blocks) of DNA can be deleted from a genome in each cell and the resulting cells tested for the effect of the deletion as described herein. In this embodiment, a cell expresses two guide RNAs that target genomic locations that define the proximal cut points that flank a block to be deleted. When the guide RNAs are simultaneously expressed, two cuts will be made in the genome, and these cuts will be repaired with the cell's existing machinery for non-homologous end joining. Such blocks can range in size from a few to hundreds of base pairs or more. Block deletion permits more genomic sequence to be tested for function in a single experiment when compared with the embodiment that uses a single guide RNA.

At least two methods can be used to express two guide RNAs in a single cell. A first method uses lentiviral plasmid cloning of paired gRNA libraries that are each expressed off of their own U6 promoter. This method has been described by Vidigal and Ventura (Nature Comm. 2015; 6:8083). These paired guide RNAs can be expressed by lentiviral delivery, or the resulting vector with the guide RNA pair can be PCR amplified with tails that are compatible for homologous recombination into the dummy guide RNA sites that are integrated into the genome as described herein. In the second method, a single RNA construct is expressed from a single U6 promoter and then cleaved by Csy4 into two guide RNAs as described by Tasi et al. (Nature Biotech. 2014; 32(6):569-76). This permits a smaller template to be used that is directly synthesized, and the template can be PCR amplified with tails for homologous recombination into the dummy guide RNA sites that are integrated into the genome as described herein. Alternatively in the second method the paired guide RNAs can be delivered to a cell by lentivirus or other means. Similar approaches may be used to integrate more than two guide RNAs into a single cell.

Guide RNAs

A guide sequence is selected or designed based on the contemplated target sequence. In some embodiments, the target sequence is a sequence within a genome of a cell. Exemplary target sequences include those that are unique in the target genome.

For example, for the S. pyogenes Cas9, a unique target sequence in a genome may include a Cas9 target site of the form $M_8N_{12}XGG$ where $N_{12}XGG$ (N is A, G, T, or C; and X can be anything) has a single occurrence in the genome. A unique target sequence in a genome may include an S. pyogenes Cas9 target site of the form $M_9N_{11}XGG$ where $N_{11}XGG$ (N is A, G, T, or C; and X can be anything) has a single occurrence in the genome.

For the S. thermophilus CRISPR1 Cas9, a unique target sequence in a genome may include a Cas9 target site of the form $M_8N_{12}XXAGAAW$ where $N_{12}XXAGAAW$ (SEQ ID NO: 173) (N is A, G, T, or C; X can be anything; and W is A or T) has a single occurrence in the genome. A unique target sequence in a genome may include an S. thermophilus CRISPR1 Cas9 target site of the form $M_9N_{11}XXAGAAW$ where $N_{11}XXAGAAW$ (SEQ ID NO: 174) (N is A, G, T, or C; X can be anything; and W is A or T) has a single occurrence in the genome.

For the S. pyogenes Cas9, a unique target sequence in a genome may include a Cas9 target site of the form $M_8N_{12}XGGXG$ where $N_{12}XGGXG$ (N is A, G, T, or C; and X can be anything) has a single occurrence in the genome. A unique target sequence in a genome may include an S. pyogenes Cas9 target site of the form $M_9N_{11}XGGXG$ where $N_{11}AGGXG$ (N is A, G, T, or C; and X can be anything) has a single occurrence in the genome. In each of these sequences "M" may be A, G, T, or C, and need not be considered in identifying a sequence as unique.

Further examples of suitable sequences can be found in Chen et al. Cell 2013, 155(7):1479-1491. An example of a suitable sequence is as follows:

This sequence provides a guide sequence of N20 followed by GUUUAAGAGCUAUGCUGGAAACAG-CAUAGCAAGUUUAAAU (SEQ ID NO: 2) which as shown above forms one or more hairpins.

It is to be understood that any hairpin sequence can be used provided it can be recognized and bound by a CRISPR/Cas nuclease.

Dummy Guide RNA Constructs

The dummy guide RNA construct is so named because it is unable to target a CRISPR/Cas nuclease to the genome of the host cell, having no variable/guide sequence sufficiently homologous to any region of the host cell genome and thus not capable of effecting a CRISPR//Cas mutation event. Such variable/guide sequence may be referred to herein as being "non-homologous" or defective, intending that it is not able to target a nucleic acid in the host cell using the CRISPR/Cas system. Similarly, the dummy guide RNA construct and the RNA it encodes may be referred to herein as being non-homologous or defective for the same reason.

The dummy guide RNA construct comprises (1) a non-homologous variable/guide sequence and (2) a guide RNA hairpin sequence, and optionally (3) a promoter sequence capable of initiating guide RNA transcription. A non-limiting example of a guide RNA hairpin sequence is the FE hairpin sequence described in Chen et al. Cell. 2013 Dec. 19; 155(7):1479-91. An example of a promoter is the human U6 promoter.

The non-homologous variable/guide sequence may be about 19-21 nucleotides in length. Similarly the variable/guide sequence in each DNA fragment is also about 19-21 nucleotides in length. An example of a non-homologous variable/guide RNA sequence and an invariant guide RNA hairpin sequence are provided in the Examples. It is to be understood that the invention is not so limited and that other non-homologous variant/guide sequences and invariant hairpin sequences may be used.

The dummy guide RNA construct is integrated into the cell at an accessible locus. An example of such a locus is the ROSA26 locus in mouse embryonic stem cells (mESCs). The dummy guide RNA construct may be integrated into the cell through the use of homologous recombination. For example, the construct may comprise sequences that flank the variable/guide sequence and invariant hairpin sequence and that have homology to the desired integration locus.

CRISPR/Cas System Nucleases

In some embodiments, the CRISPR/Cas nuclease is a type II CRISPR/Cas nuclease. In some embodiments, the CRISPR/Cas nuclease is Cas9 nuclease. In some embodiments, the Cas9 nuclease is S. pneumoniae, S. pyogenes, or S. thermophilus Cas9, and may include mutated Cas9 derived from these organisms. The nuclease may be a functionally equivalent variant of Cas9. In some embodiments, the CRISPR/Cas nuclease is codon-optimized for expression in a eukaryotic cell. In some embodiments, the CRISPR/Cas nuclease directs cleavage of one or two strands sgRNA<sup>(F+E)</sup>combined

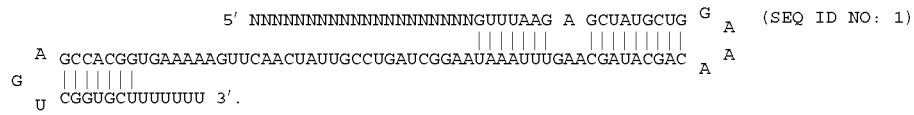

(SEQ ID NO: 1)

at the location of the target sequence. The CRISPR/Cas system nucleases include but are not limited to Cas9 and Cpf1.

Host Cells

Virtually any eukaryotic cell type can be used as a host cell provided it can be cultured in vitro and modified as described herein. Preferably, the host cells are an pre-established cell line. The Examples use mESC lines as host cells but the methods of the invention are not so limited. The cells and cell lines may be human cells or cell lines, or they may be non-human, mammalian cells or cell lines.

Amplified DNA Fragments Comprising Guide Sequences

The pool of amplified DNA fragments introduced into the host cell and intended to homologously recombine with the dummy guide RNA construct comprise sequence derived from the host cell genome. In some embodiments, the sequence derived from the host cell genome is intended to act as the guide sequence. When used with CRISPR/Cas nuclease, such guide sequence will target the nuclease to the homologous sequence in the host cell genome.

The guide sequences can be derived from any region of the genome and can be tested for their effect on virtually any function of the cell. Alternatively and as described in greater detail herein, the guide sequence can be derived from a particular region and can be tested for their effect on proximal nucleic acids such as coding sequences including knock-in reporter sequences. In the Examples, the method was used to generate a pool of DNA fragments from the regulatory domains of four transcription factors. The totality of the fragments blanket the regulatory region of interest, whether upstream or downstream of a gene of interest, or both. The totality of the fragments may span+/−10 kb, or +/−20 kb, or +/−50 kb, or +/−100 kb, or more of regulatory sequence (upstream and downstream) of the gene of interest. The variable/guide sequences are typically about 19-20 nucleotides in length.

Reporter Genes and Proteins, and Readouts

The reporter gene may be integrated into the cells using a CRISPR/Cas mechanism, in some embodiments. For example, to generate a "knock-in" of a reporter construct, a similar approach to that used to integrate a DNA fragment into a dummy guide RNA construct locus. For example, an expression vector, such as a plasmid, may be used that comprises a promoter (e.g., U6 promoter), a guide RNA hairpin sequence, and a guide sequence that targets the desired genomic locus where the reporter construct is to be integrated. Such an expression vector may be generated by cloning the guide sequence into an expression construct comprising the remaining elements. A DNA fragment comprising the coding sequence for the reporter protein can be generated and subsequently modified to include homology arms that flank the coding sequence of the reporter protein. The guide RNA expression vector, the amplified DNA fragments comprising the reporter protein coding sequence, and a CRISPR/Cas nuclease (or an expression vector encoding the nuclease) are introduced into the host cell (e.g., via electroporation). The expression vectors may further comprise additionally selection markers such as antibiotic resistance markers to enrich for cells successfully transfected with the expression vectors. Cells that express the reporter protein can be further selected. Exemplary sequences for the guide RNAs, homology arms and genomic integration sites for particular mESC loci are provided in the Examples.

Reporter genes are used for identifying potentially transfected cells and for evaluating the functionality of regulatory sequences. In general, a reporter gene is a gene that is not endogenous or native to the host cells and that encodes a protein that can be readily assayed. Reporter genes that encode for easily assayable proteins are known in the art and are typically preferred.

The reporter proteins may be selected from a variety of reporter systems available in the art. The Examples use green fluorescent protein (GFP) as the reporter protein but the invention is not so limited. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, HcRed, DsRed, cyan fluorescent protein (CFP), yellow fluorescent protein (YFP), and autofluorescent proteins including blue fluorescent protein (BFP), cell surface markers, antibiotic resistance genes such as neo, and the like.

It is to be understood that reporter genes or other selectable marker genes can be used in the methods described herein to identify and/or select cells from the transfected population. In some instances, the selectable marker or reporter genes may be flanked with appropriate regulatory sequences to enable expression in the host cells. In some instances, the selectable marker or reporter gene is flanked by a native regulatory region that will be targeted using the CRISPR/Cas mutation strategy described herein.

Expression Vectors

The term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Expression vectors in recombinant DNA techniques often take the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

"Complementarity" refers to the ability of a nucleic acid to form hydrogen bond(s) with another nucleic acid sequence by either traditional Watson-Crick or other non-traditional types.

A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The term "homologous" as used herein refers to a nucleic acid sequence that has complementarity to another nucleic acid sequence or to the complement of such sequence. Two sequences can have a degree of homology that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides. Two sequences that are homologous are able to hybridize to each other under stringent conditions.

The following Examples are included for purposes of illustration and are not intended to limit the scope of the invention.

EXAMPLES

Introduction

We introduce the Multiplexed Editing Regulatory Assay (MERA), a high-throughput CRISPR/Cas9-based approach that analyzes the regulatory genome for function in its native context. By tiling thousands of mutations across ~40 kb of cis-regulatory genomic space and using knock-in GFP reporters to read out gene activity, we obtain quantitative information on the contribution of cis-regulatory regions to gene expression. We identify proximal and distal regulatory elements necessary for gene expression of four embryonic stem cell-specific genes. We show a consistent contribution of neighboring gene promoters to gene expression, and we identify a novel class of unmarked regulatory elements (UREs) that control gene expression but do not have typical enhancer epigenetic or chromatin features. Comparing thousands of functional and non-functional genotypes at a genomic location, we find the base pair-resolution functional motifs of regulatory elements.

Experimental Design and Overview

Library Design for MERA Assay

In addition to 10 GFP-targeting gRNAs we designed 3908 gRNAs specific to each of the four libraries for TDGF, Nanog, Zfp42 and Rpp25. For TDGF we selected a −20 kb to +20 kb proximal region around the TDGF promoter to profile 3908 gRNAs that were designed for this region. For Nanog, Rpp25, and Zfp42 we prioritized the design of 3908 gRNAs based on regions of strong DNAse-I enrichment going up to 100 kb on either side of the gene promoter. Further, we used PolII Chia-Pet data to find distal regions that are predicted to interact with the promoter. In case of a large number of Chia-pet regions, we filtered interactions based on other enhancer features such as p300 binding, DNASE-I enrichment, active histone modifications etc. overlapping distal Chia-pet regions.

Libraries were ordered as 98-100 bp sequences containing a 19-20 bp protospacer targeting the genomic sequence of interest (i.e., variable or guide sequence), an optional G if the protospacer does not already begin with one, and surrounding sequences homologous to the U6 promoter and gRNA hairpin. The format was as follows: TTATATATCTTGTGGAAAGGACGAAACACC[GN$_{18-20}$] GTTTAAGAGCTATGCTGGAAA CAGCATAGCAAGTT- TAAATAAGGCTAGT (SEQ ID NO:3) Libraries were ordered from LC Sciences.

Mapping of MERA Reads

We mapped the sequence composing of sample barcode, primer and exact matches of the designed gRNA sequence to the sequenced reads. Counts for each gRNA for either GFP$^{neg}$, GFP$^{medium}$ or bulk populations were obtained by counting the number of sequenced reads that showed exact matches to the gRNA.

The gRNA integration rate into cellular genomic DNA was found to be 93% for Tdgf1 but appeared to be only 43% for Zfp42. In order to determine if this was caused by inefficient integration or due to synthesis errors, we sequenced the gRNA library for Zfp42 and found that only 1723 of the 3919 guide RNAs in the Zfp42 library were synthesized accurately. Among these, 1718/1723 were detected in the bulk library of at least one replicate. Hence, we estimate that the integration rate of gRNAs is >90% of those that are synthesized. Oligonucleotide library synthesis quality is unaffected by whether a gRNA integration approach such as MERA or a lentiviral cloning approach is taken, and thus MERA enables integration of the vast majority of available gRNAs.

Identification of gRNAs that are Significantly Enriched in GFP$^{neg}$ and GFP$^{medium}$ Populations In order to detect gRNAs with statistically significant overrepresentation in GFP$^{neg}$ and GFP$^{medium}$ populations, we perform a step-wise procedure.

Step 1. We normalize the gRNA sequence read counts, which can vary between sequencing runs of bulk, GFP$^{medium}$ and GFP$^{neg}$ populations due to differences in cell number and diversity of the respective populations (data not shown). In order to normalize these read ranges, we assume that the positive control gRNAs targeting the GFP coding region always induce loss of GFP expression, which is consistent with our previous results showing that over 99% of cells receiving a GFP-targeting gRNA lose GFP expression (Arbab et al. Stem Cell Reports, 2015). In addition, GFP$^{neg}$, and to a lesser extent GFP$^{med}$ reads are always observed to be proportional to the bulk reads for the =targeting guide RNAs, to a much greater extent than for all guide RNAs (data not shown). Hence, we predict the number of GFP$^{neg}$ reads we would see for each gRNA given its bulk and GFP$^{med}$ count if it always caused GFP loss. In order to do this, we build two different kinds of linear models depending on the data available I. In case of Tdgf1$^{GFP}$ and Zfp42$^{GFP}$, we have a GFP$^{medium}$ as well as GFP$^{neg}$ population, along with 3 to 4 biological replicates per cell-line. We assume that for any GFP-targeting gRNA, the majority of bulk reads are derived from the GFP$^{neg}$ population. However, each gRNA may also cause some intermediate loss of GFP due to variable mutations or imperfect sorting. In addition, there is a low gRNA-dependant intercept or GFP$^{pos}$ population, which may be a small fraction of mutations induced by a particular gRNA that do not cause GFP-loss.

In order to transform the bulk reads to the GFP$^{neg}$ scale, we model GFP$^{neg}$ as the dependant variable, and GFP$^{medium}$ and bulk reads as independent variables using a generalized linear model (Nelder and Wedderbu, J R Stat Soc Ser a-G 135:370 (1972)). The intercept is modeled as being dependent on the gRNA but independent across replicates, while the slopes are considered as having a replicate-dependent component also.

The model is of the form $$y \sim x1 + x2 + (z11|g1) + (x1|g2) + (x2|g2)$$

where,
y=GFP$^{neg}$
x1=Bulk
x2=GFP$^{medium}$
z11=Intercept
g1=grouping by gRNA
g2=grouping by replicate In order to transform the bulk reads to the GFP$^{medium}$ scale, we use the same model but with
y=GFP$^{medium}$
x2=GFP$^{neg}$ II. In case of Nanog$^{GFP}$ and Rpp25$^{GFP}$, we have only a GFP$^{neg}$ population and at most 2 replicates. In this case we build an independent linear regression model for each replicate of the form:

$$y \sim x1 + z11,$$

where
y=GFP$^{neg}$
x1=Bulk
z11=Intercept

Using the linear regression models, we now transform all bulk reads to either GFP$^{neg}$ or GFP$^{medium}$ populations, depending on if we are interested in finding gRNAs enriched in GFP$^{neg}$ or GFP$^{medium}$ populations respectively.

Step 2. We now use the fact that since the dummy gRNA (negative control) should not occur in GFP$^{neg}$/GFP$^{medium}$ cells any reads corresponding to this gRNA in the GFP$^{neg}$/GFP$^{medium}$ population are due to random chance. Hence, we can obtain the null probability of observing reads in the GFP$^{neg}$/GFP$^{medium}$ population by dividing the GFP$^{neg}$/GFP$^{medium}$ reads for the dummy gRNA by the number of bulk reads for the dummy gRNA transformed to the GFP$^{neg}$/GFP$^{medium}$ scale. We then use a binomial distribution to calculate significance for a gRNA based on this null probability, with the gRNA's observed number of GFP$^{neg}$/GFP$^{medium}$ reads as the number of successes, and the number of bulk-transformed reads for the gRNA as the number of trials.

Datasets for Comparison and Visualization with Enriched gRNA

The UCSC genome browser (Kent et al. Genome research 12: 996-1006 (2002)) was used to visualize the data and create genomic view snapshots for regulatory regions of various genes.

Enhancer Predictions

The enhancer predictions were made using the RFECS method (Rajagopal et al. PLoS computational biology 9: e1002968 (2013)) using 6 histone modifications from ENCODE (Nature 489:57-74 (2012)) trained on p300 binding site data from mouse embryonic stem cells. Enhancers were separated into "strong" and "weak" categories based on presence of H3K27ac at levels greater than input. Further boundaries of enhancers were called using a Sobel edge-detection algorithm implemented in MATLAB. Edges were identified for an input subtracted RPKM (reads per kilobase per million)-normalized H3K27ac reads (Rajagopal et al. PLoS computational biology 9: e1002968 (2013)) in the case of strong enhancers and RPKM-normalized H3K4me1 reads for weak enhancers.

DNase-I hotspot: We used the DNase-seq dataset previously generated (Sherwood et al. Nature biotechnology 32: 171-178 (2014)) and called hotspots using a standard hotspot algorithm (John et al. Nature genetics 43:264-268 (2011)).

TF density: The GEM algorithm (Guo et al. PLoS computational biology 8: e1002638 (2012)) was applied to transcription factor Chip-seq datasets for the following transcription factors: Nanog, Oct4, Sox2, TCF3, p300, CTCF, Smc1, Smad3, c-Myc, Med12, Med1, CTCF, E2F1, Esrrb, Klf4, n-Myc, Nr5a2, Tcfcp2l1, Stat3, Zfx.

Analysis of Deep Sequencing Datasets

Figure 4A:
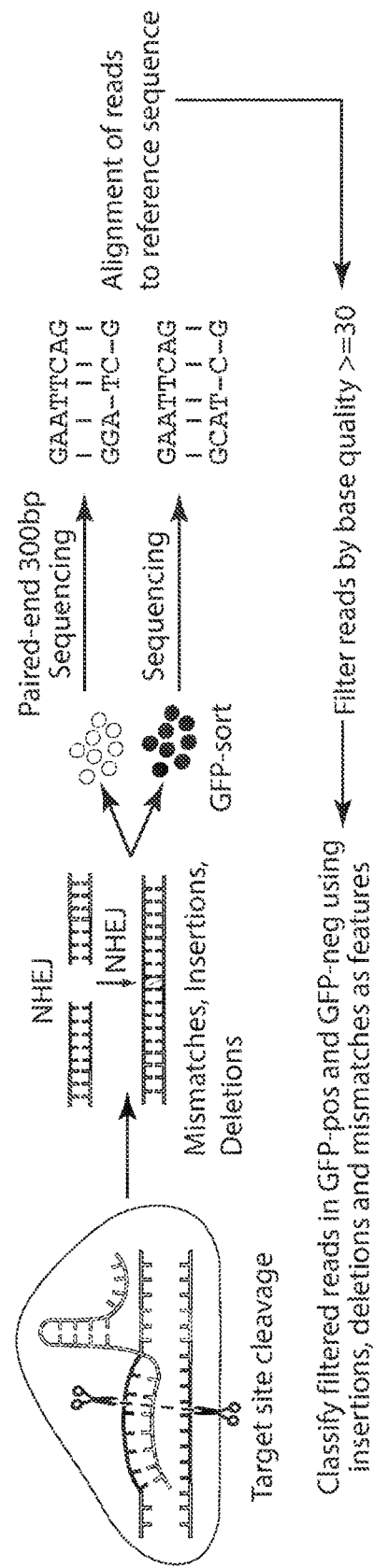
FIGS. 4A-4D. Functional motif discovery analysis of region-specific mutant genotypes at enhancers reveals required regulatory motifs.
Figure 4B:
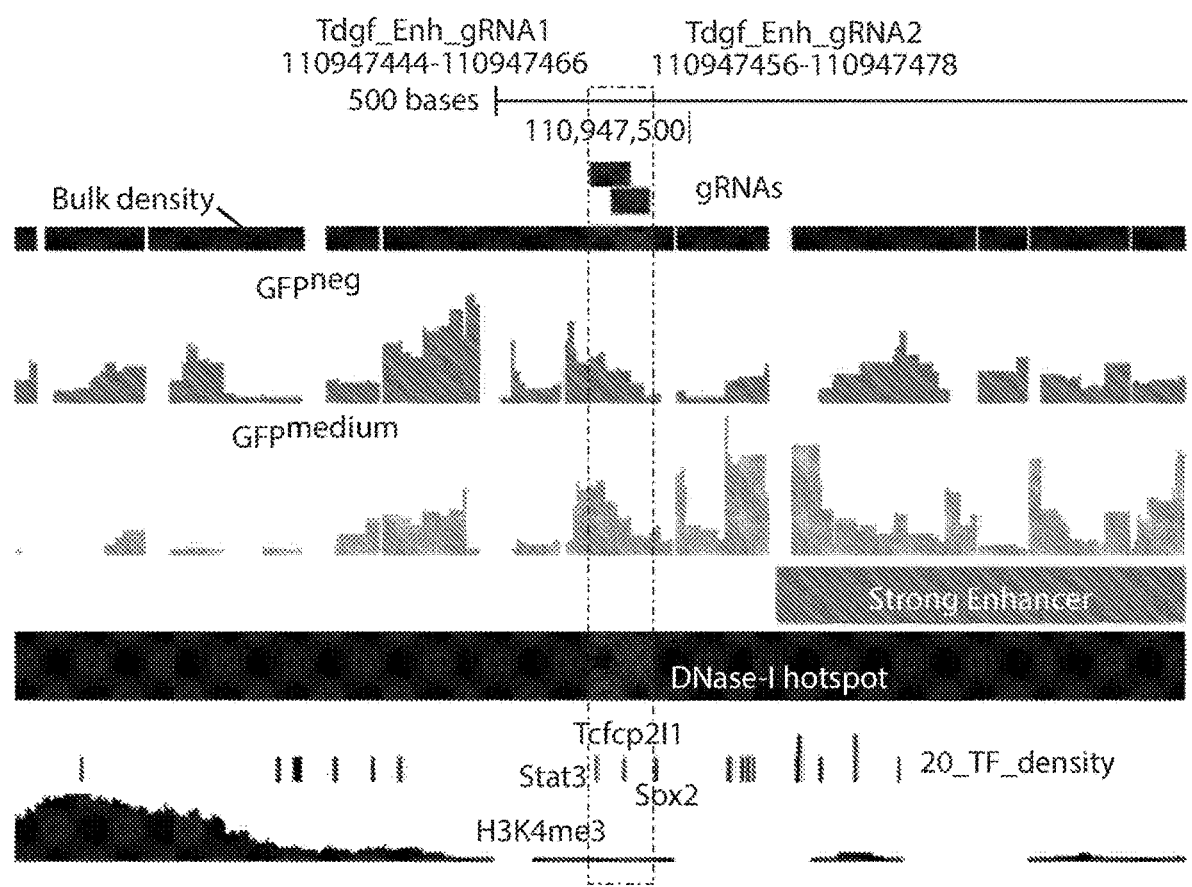
Figure 4C:
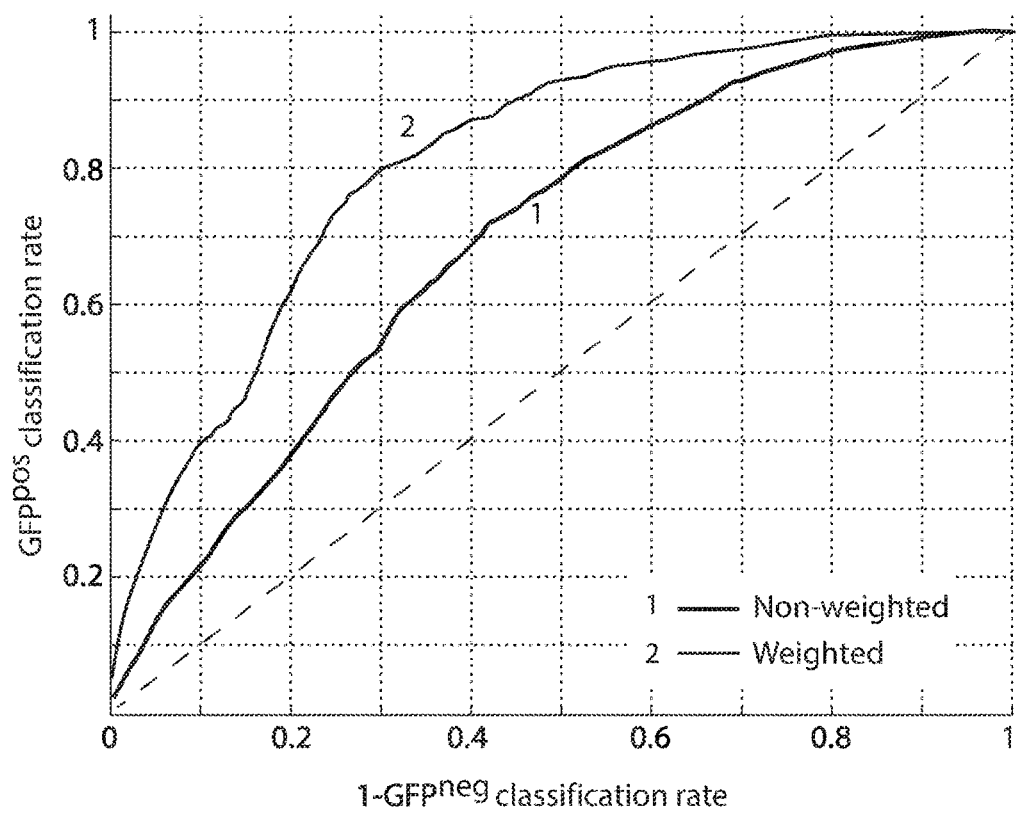

Individual scCRISPR-mediated mutation by a selected gRNA was performed in a large pool of cells to create tens of thousands of unique mutated genotypes at the site. We then flow cytometrically sorted GFP$^{pos}$ and GFP$^{medium/neg}$ populations and performed 150 bp paired-end sequencing on regions surrounding each targeted site to obtain genotypic data on thousands of mutated regions that did and did not induce loss of GFP expression (FIG. 4A). Deep-sequencing datasets were filtered for sequence quality by using a minimum base quality filter of 30. After stripping barcodes, the length of each paired end read was 145 bp. We aligned these 145 bp long genotypes to the reference genotype extended by 30 bp downstream (total of 175 bp). Alignment of sequenced reads to the reference genome was performed using the semi-global version of the Needleman Wunsch algorithm with a gap opening penalty of 8 and gap extension penalty of 4. The command in MATLAB used was:
nwalign(Reference_Seq,
Genotype_seq,'alphabet','NT','gapopen',8,'ExtendGap',4, 'glocal','true');

Functional Motif Discovery

After globally aligning and filtering reads for sequence quality (per base quality >=30), mismatches, deletions and insertions were counted with respect to the base position in the reference. We observed long stretches of mutations with combinations of mismatches and deletions. Hence, we defined a "length of disruption" as a continuous series of mutations with maximum intervening matches of <5 bases. We plotted the left and right ends of these disruptions and observed the majority of disruptions originated within the gRNA as expected with very few short mutations lying outside that could be assumed to be one or two base sequencing errors (data not shown). While a majority of disruptions extending beyond the ends of the guide RNA were enriched for GFP$^{neg}$ (data not shown), we also observed a mixed population of GFP$^{neg}$ as well as GFP$^{pos}$ deletions lying within −20/+20 bp of the gRNA. Since we wish to assess the local effect of the gRNA on GFP-loss, we limited further analysis to genotypes with disruptions that originate within the gRNA and do not go beyond 20 bp of the gRNA.

Restricting our analysis to these genotypes, we observed increased mutation around the gRNA cleavage site in both GFP$^{pos}$ and GFP$^{medium/neg}$ populations (data not shown). Mismatch, deletion, and insertion mutations were all observed, with deletions predominating in the GFP$^{medium/neg}$ genotypes (data not shown).

In order to develop a base-level motif logo, we defined a base-level score representing the deviation of GFP$^{neg}$ population from reference as compared to the deviation of the GFP$^{pos}$ population from reference. In order to find the distance of a base from reference, we used the Hellinger measure (Liese and Miescke, Statistical Decision Theory: Estimation, Testing, and Selection. Springer Ser Stat, 1-677 (2008)) for finding the distance between two discrete distributions:

$$H(P, Q) = \frac{1}{\sqrt{2}} \sqrt{\sum_{i=1}^{k} \left(\sqrt{p_i} - \sqrt{q_i}\right)^2},$$

Here, we had five possible values per base which were the frequency of occurrence of each base type (A,C,T,G) and a fifth deletion (D). The motif score at any base was defined as:

Base score=log 10 (H(GFP$^{neg}$, Reference)/H(GFP$^{pos}$, Reference)) These base scores were plotted as a motif logo along −20/+20 bp of the gRNA to indicate relative importance of each base, independent of the cutting biases of the gRNA. It should be noted that since all mutations for GFP$^{pos}$ as well as GFP$^{neg}$ arise within the seed region of the gRNA, it is sometimes difficult to obtain a base-level importance score for these bases surrounding the cleavage site. However, due to the random lengths of stretches of mutations originating from the cleavage site we can observe distinct sequence profiles emerging upstream and downstream of these bases.

Classification of GFP$^{pos}$ and GFP$^{neg}$ Populations

We represented mismatches, insertions and deletions within −20/+20 bp of the gRNA as features. For all of the bases within the gRNA we represented 5 possibilities—A, C, T, G, and deletion. The feature for a base was one of four values for a particular base or the integer number of deleted bases starting at that base. Converting this categorical representation to a numeric format, we obtained 5×(length of gRNA+40) features. Insertions were represented as the integer number of bases inserted immediately after each base of the gRNA and flanking boundaries. Hence, the total features were=6×(length of gRNA+40)

We performed 5-fold classification of unique genotypes in GFP$^{pos}$ and GFP$^{neg}$ populations using a parallelized random forest implemented in MATLAB. We used 100 trees and ascertained that the out-of-bag classification error had reached convergence at this parameter value. Classification rate for a test-set genotype, was computed in an unweighted manner by counting each test-set genotype only once. In case of weighted accuracy measures, we weighted the accuracy of classification for each test-set genotype, by the number of reads assigned to it.

Conservation of Bases

We examined the vertebrate phastcons score for every base in the gRNA at the URE to see if there was a correspondence with the importance of the base for regulation as determined above (data not shown).

Materials and Methods

Cell Culture

Mouse embryonic stem cell (mESC) culture was performed according to previously published protocols (Nature 489:57-74 (2012)). All experiments were performed with 129P2/OlaHsd mESCs. mESCs were maintained on gelatin-coated plates feeder-free in mESC media composed of Knockout DMEM (Life Technologies) supplemented with 15% defined fetal bovine serum (FBS) (HyClone), 0.1 mM nonessential amino acids (NEAA) (Life Technologies), Glutamax (GM) (Life Technologies), 0.55 mM 2-mercaptoethanol (b-ME) (Sigma), 1×ESGRO LIF (Millipore), 5 nM GSK-3 inhibitor XV and 500 nM U0126. Cells were regularly tested for mycoplasma.

ROSA26 gRNA Cassette Knock-In

Our first step was to derive a mESC line with a dummy gRNA in the universally accessible ROSA26 locus (Sherwood et al. Nature biotechnology 32: 171-178 (2014)). We did so using the following protocol, which involves amplification of the desired dummy gRNA knock-in construct with short PCR-amplified homology arms using a protocol we have recently developed (Arbab et al. Stem Cell Reports, 2015):

1. PCR amplify homology arm-flanked dummy gRNA in two successive PCR steps.

PCR a plasmid containing the dummy gRNA downstream of the U6 promoter and including the "FE" modified gRNA hairpin (John et al. Nature genetics 43:264-268 (2011)) with primers that amplify the entire expression cassette with ROSA26 homology arms:

1. 091514_U6gRNA_ROSAHDR_fw
(SEQ ID NO: 4)
CCAGGTTAGCCTTTAAGCCTGCCCAGAAGA CTCCCGCCCA GCATGTGA

GGGCCTATTTCC 2. 091514_U6gRNA_ROSAHDR_rv
(SEQ ID NO: 5)
GGAGAATCCCTTCCCCCTCTTCCCTCGTGAT CTGCA TCGCGATTTTAC

CACATTTGTAGA

Use 2× Phusion PCR Mastermix (NEB), 25 uL reaction, 35 cycles of 2-step PCR (98 for 10s, 72 for 45s) using 3% DMSO Test ~2 uL, expecting 750 bp band.

Use 10 uL unpurified product in a new reaction with the following primers that extend the ROSA26 homology arm to enable high-efficiency genomic knock-in of the dummy gRNA expression cassette:

3. 091514_ROSAHDR_Ext_fw
(SEQ ID NO: 6)
ACACCTGTTCAATTCCCCTGCAGGACAACGCCCA CACACCAGGTTAGCC

TTTAAGCCTGC 4. 091514_ROSAHDR_40bpext_rv
(SEQ ID NO: 7)
TCTGCTGCCTCCTGGCTTCTGAGGACCGCCCT GGGCCTGGGAGAATCCC

TTCCCCCTCTT

Use a 200 uL Phusion reaction, 35 cycles of 2-step PCR (98 for 10s, 72 for 45s) using 3% DMSO Test ~2 uL, expecting 800 bp band.

Minelute PCR purify the product in 10 uL elution buffer.

2. Co-electroporate mESC with Cas9, gRNA, and PCR-amplified homology arm construct to generate ROSA26 locus dummy gRNA a. Co-electroporate 1 well of a 6-well plate of mESC with:
5 ug p2T CBh Cas9 BlastR
5 ug p2T U6sgROSA26-FE HygroR (p2T sg82 HygR)
MinElute-purified ROSA-HDR U6sgIhhPro-FE from 200 uL PCR reaction Vacuum concentrate to <20 uL volume of DNA, use 120 uL EmbryoMax Electroporation Buffer (ES-003-D, Millipore). DNA mixture and mESC suspension were mixed and electroporated in a 0.4 cm electroporation cuvette using a Bio-Rad electroporator at 230 V, 0.500 uF, and maximum resistance. Transiently select with Blasticidin and Hygromycin from 24-72 hours after electroporation (total of 48 hours of selection).

We identified clonal knock-in lines through mESC colony genomic DNA PCR with the following primers, identifying a 134-bp knock-in band:

```
5. 080814_U6gRNA_late_fw
                                    (SEQ ID NO: 8)
   TCTACAAATGTGGTAAAATCGCGA 091514_ROSA_downstream_rv
                                    (SEQ ID NO: 9)
   GGGAGGGGAGTGTTGCAATA
```

We sequence verified the knock-in lines using the following primers, isolating and sequencing the 913 bp knock-in band:

```
6. 091514_ROSA_upstream_fw
                                    (SEQ ID NO: 10)
   TGGGAAGTCTTGTCCCTCCA 7. 091514_ROSA_downstream_rv
                                    (SEQ ID NO: 9)
   GGGAGGGGAGTGTTGCAATA
```

We thus obtained a heterozygous knock-in cell line which guarantees that only one gRNA construct can be integrated and expressed per cell in the context of pooled screening. Sequences of the ROSA26 locus are below:

```
Wildtype ROSA26 locus
                                    (SEQ ID NO: 11)
TCCCATTTTCCTTATTTGCCCCTATTAAAAAACTTCCCGACAAAACCGAA

AATCTGTGGGAAGTCTTGTCCCTCCAATTTTACACCTGTTCAATTCCCCT

GCAGGACAACGCCCACACACCAGGTTAGCCTTTAAGCCTGCCCAGAAGAC

TCCCGCCCATCTTCTAGAAAGACTGGAGTTGCAGATCACGAGGGAAGAGG

GGGAAGGGATTCTCCCAGGCCCAGGGCGGTCCTCAGAAGCCAGGAGGCAG

CAGAGAACTCCCAGAAAGGTATTGCAACACTCCCCTCCCCCCTCCGGAGA

AGGGTGCGGCCTTCTCCCCGCCTACTCCAC

ROSA26 with U6 sgdummygRNA-FE knock-in
                                    (SEQ ID NO: 12)
TCCCATTTTCCTTATTTGCCCCTATTAAAAAACTTCCCGACAAAACCGAA

AATCTGTGGGAAGTCTTGTCCCTCCAATTTTACACCTGTTCAATTCCCCT

GCAGGACAACGCCCACACACCAGGTTAGCCTTTAAGCCTGCCCAGAAGAC

TCCCGCCCAGCATGTGAGGGCCTATTTCCCATGATTCCTTCATATTTGCA

TATACGATACAAGGCTGTTAGAGAGATAATTGGAATTAATTTGACTGTAA

ACACAAAGATATTAGTACAAAATACGTGACGTAGAAAGTAATAATTTCTT

GGGTAGTTTGCAGTTTTAAAATTATGTTTTAAAATGGACTATCATATGCT

TACCGTAACTTGAAAGTATTTCGATTTCTTGGCTTTATATATCTTGTGGA

AAGGACGAAACACCGAGGCGTCTGGGTGGCTCTTGGTTTAAGAGCTATGC

TGGAAACAGCATAGCAAGTTTAAATAAGGCTAGTCCGTTATCAACTTGAA

AAAGTGGCACCGAGTCGGTGCTTTTTTGTTTAGAGCTAGAAATAGCAAG

TTAAAATAAGGCTAGTCCGTTTTTAGCGCGTGCGCCAATTCTGCAGACAA

ATGGCTCTAGAGGTACGGCCGCTTCGAGCAGACATGATAAGATACATTGA

TGAGTTTGGACAAACCACAACTAGAATGCAGTGAAAAAAATGCTTTATTT

GTGAAATTTGTGATGCTATTGCTTTATTTGTAACCATTATAAGCTGCAAT

AAACAAGTTAACAACAACAATTGCATTCATTTTATGTTTCAGGTTCAGGG

GGAGATGTGGGAGGTTTTTTAAAGCAAGTAAAACCTCTACAAATGTGGTA

AAATCGCGATGCAGATCACGAGGGAAGAGGGGGAAGGGATTCTCCCAGGC

CCAGGGCGGTCCTCAGAAGCCAGGAGGCAGCAGAGAACTCCCAGAAAGGT

ATTGCAACACTCCCCTCCCCCCTCCGGAGAAGGGTGCGGCCTTCTCCCCG

CCTACTCCAC
```

We then proceeded to gRNA screening. We use homologous recombination inside target cells to replace the dummy gRNA with a pool of amplified gRNAs that contain homology tails matching the dummy gRNA and thus will seamlessly integrate as functional gRNAs. To do so, we co-electroporated Cas9, a gRNA plasmid that cuts the dummy gRNA, and a library of replacement gRNA PCR fragments. The sequence of the gRNA that cuts the dummy gRNA is

```
                                    (SEQ ID NO: 13)
GAAACACCGAGGCGTCTGGG
```

GFP Fusion/Knock-in Line Generation

We generated gene knock-in constructs with short PCR-amplified homology arms using a protocol we have recently developed (Arbab et al. Stem Cell Reports, 2015). For each knock-in, we used mESCs with an integrated ROSA26 gRNA cassette, constructed as described above.

For Zfp42 and Tdgf1, we constructed GFP replacement alleles in which we added GFP at the translational start site of the genes. This approach should disrupt endogenous gene activity in a single allele of that gene. For Nanog and Rpp25, we constructed C-terminal GFP fusion proteins in which the full-length protein is fused to GFP. This approach should maintain protein functionality.

To perform knock-in, an gRNA targeting the desired genomic insertion site was cloned into a plasmid containing a U6 promoter, gRNA hairpin, and Hygromycin resistance cassette. GFP was amplified in two successive steps with homology arm primers adding 70-80 bp of homologous sequence surrounding the desired insertion site to GFP. Then mESCs were co-electroporated with the gRNA plasmid, the GFP homology arm amplicon, and a plasmid expressing Cas9 and a Blasticidin resistance cassette. Transient Blasticidin and Hygromycin selection was performed from 24-72 hours after electroporation, then GFP-expressing mESCs were flow cytometrically sorted and then clonally purified. Genomic DNA PCRs confirmed site-specific genomic integration of GFP. An expanded protocol for this procedure is contained in Arbab et al. Stem Cell Reports, 2015, and the sequences of gRNAs, homology arms, and genomic integration sites are shown below.

```
Tdgf1
Tdgf1 gRNA:
                                    (SEQ ID NO: 14)
GAGATGGGGTACTTCTCATCC Tdgf1 genomic region:
                                    (SEQ ID NO: 15)
TTGGGTGTTTCGAGAATGGCTTTATGAACTAAAGCCATCTGCTAATATTG

TGTTTCTTGTCTTTTCCTCCAACGTTTTTACGAGCCGTCGAAGATGGGGT

ACTTCTCATCCAGGTATGAGCTAACCTTGACTTTTTGGTTGCTGGAGATA

GCCACTTCGGAAAATCACGTTCTATGACGCTCTGATTTTTGTCTTGCTTG

AACCTTGTCAGTAAC

GFP in Tdgf1 locus
```

-continued (SEQ ID NO: 16)
CTCTCTCATTTGGCATATCTTTCTTTTTAATCTACTGTTTTCATTTTGTG

AAATTAGCCTTTGGGTGTTTCGAGAATGGCTTTATGAACTAAAGCCATCT

GCTAATATTGTGTTTCTTGTCTTTTCCTCCAACGTTTTTACGAGCCGTCG

AAGATGGTGAGCAAGGGCGAGGAGCTGTTCACCGGGGTGGTGCCCATCCT

GGTCGAGCTGGACGGCGACGTAAACGGCCACAAGTTCAGCGTGTCCGGCG

AGGGCGAGGGCGATGCCACCTACGGCAAGCTGACCCTGAAGTTCATCTGC

ACCACCGGCAAGCTGCCCGTGCCCTGGCCCACCCTCGTGACCACCCTGAC

CTACGGCGTGCAGTGCTTCAGCCGCTACCCCGACCACATGAAGCAGCACG

ACTTCTTCAAGTCCGCCATGCCCGAAGGCTACGTCCAGGAGCGCACCATC

TTCTTCAAGGACGACGGCAACTACAAGACCCGCGCCGAGGTGAAGTTCGA

GGGCGACACCCTGGTGAACCGCATCGAGCTGAAGGGCATCGACTTCAAGG

AGGACGGCAACATCCTGGGGCACAAGCTGGAGTACAACTACAACAGCCAC

AACGTCTATATCATGGCCGACAAGCAGAAGAACGGCATCAAGGTGAACTT

CAAGATCCGCCACAACATCGAGGACGGCAGCGTGCAGCTCGCCGACCACT

ACCAGCAGAACACCCCCATCGGCGACGGCCCCGTGCTGCTGCCCGACAAC

CACTACCTGAGCACCCAGTCCGCCCTGAGCAAAGACCCCAACGAGAAGCG

CGATCACATGGTCCTGCTGGAGTTCGTGACCGCCGCCGGGATCACTCTCG

GCATGGACGAGCTGTACAAGTAAAGCGGCCGCAATTCACTCCTCAGGTGC

AGGCTGCCTATCAGAAGGTGGTGGCTGGTGTGGCCAATGCCCTTGCTCAC

CATGGTGAAGGGTGGGCGCGCCGACCCAGCTTTCTTGTACAAAGTGGTTG

ATCTAGAGGGCCCGCGGTTCGAAGGTAAGCCTATCCCTAACCCTCTCCTC

GGTCTCGATTCTACGCGTACCGGTCATCATCACCATCACCATTGAGTTTA

TCCATCACACTGGCGGCCGCTCGAGGGGGATCCACTAGTTCTAGAGCGGC

CGCTTCGAGCAGACATGATAAGATACATTGATGAGTTTGGACAAACCACA

ACTAGAATGCAGTGAAAAAAATGCTTTATTTGTGAAATTTGTGATGCTAT

TGCTTTATTTGTAACCATTATAAGCTGCAATAAACAAGTTAACAACAACA

ATTGCATTCATTTTATGTTTCAGGTTCAGGGGGAGATGTGGGAGGTTTTT

TAAAGCAAGTAAAACCTCTACAAATGTGGTAAAATCGCGAGAGCTAACCT

TGACTTTTTGGTTGCTGGAGATAGCCACTTCGGAAAATCACGTTCTATGA

CGCTCTGATTTTGTCTTGCTTGAACCTTGTCAGTAACATTGCTGCTTTT

CCTGAAGAACCTGGAACTT

Zfp42
Zfp42 gRNA:

(SEQ ID NO: 17)
GAATGAACAAATGAAGAAAA

Zfp42 genomic region:

(SEQ ID NO: 18)
TGGGTTATTATCTAAGGCAGGTGTTTGCGGATCAGTGCCCCCTGGAAGTG

AGTCATAGGCATTGTTCAAGAAGGAAGCAGCTAAGACAACATGAATGAAC

AAAAAATGAATGAACAAATGAAGAAAACGGCAAAGACAAGTGGCCAGAAA

GGGCCGGGCGGAAGAGCCCTCGACAGACTGACCCTAAAGCAAGACGAGGC

AAGGCCAGTCCAGAATACCAGAGTGG

GFP in Zfp42 locus:

(SEQ ID NO: 19)
TGGGTTATTATCTAAGGCAGGTGTTTGCGGATCAGTGCCCCCTGGAAGTG

AGTCATAGGCATTGTTCAAGAAGGAAGCAGCTAAGACAACATGAATGAAC

AAAAAATGAATGTGAGCAAGGGCGAGGAGCTGTTCACCGGGGTGGTGCCC

ATCCTGGTCGAGCTGGACGGCGACGTAAACGGCCACAAGTTCAGCGTGTC

CGGCGAGGGCGAGGGCGATGCCACCTACGGCAAGCTGACCCTGAAGTTCA

TCTGCACCACCGGCAAGCTGCCCGTGCCCTGGCCCACCCTCGTGACCACC

CTGACCTACGGCGTGCAGTGCTTCAGCCGCTACCCCGACCACATGAAGCA

GCACGACTTCTTCAAGTCCGCCATGCCCGAAGGCTACGTCCAGGAGCGCA

CCATCTTCTTCAAGGACGACGGCAACTACAAGACCCGCGCCGAGGTGAAG

TTCGAGGGCGACACCCTGGTGAACCGCATCGAGCTGAAGGGCATCGACTT

CAAGGAGGACGGCAACATCCTGGGGCACAAGCTGGAGTACAACTACAACA

GCCACAACGTCTATATCATGGCCGACAAGCAGAAGAACGGCATCAAGGTG

AACTTCAAGATCCGCCACAACATCGAGGACGGCAGCGTGCAGCTCGCCGA

CCACTACCAGCAGAACACCCCCATCGGCGACGGCCCCGTGCTGCTGCCCG

ACAACCACTACCTGAGCACCCAGTCCGCCCTGAGCAAAGACCCCAACGAG

AAGCGCGATCACATGGTCCTGCTGGAGTTCGTGACCGCCGCCGGGATCAC

TCTCGGCATGGACGAGCTGTACAAGTAAAGCGGCCGCAATTCACTCCTCA

GGTGCAGGCTGCCTATCAGAAGGTGGTGGCTGGTGTGGCCAATGCCCTTG

CTCACCATGGTGAAGGGTGGGCGCGCCGACCCAGCTTTCTTGTACAAAGT

GGTTGATCTAGAGGGCCCGCGGTTCGAAGGTAAGCCTATCCCTAACCCTC

TCCTCGGTCTCGATTCTACGCGTACCGGTCATCATCACCATCACCATTGA

GTTTATCCATCACACTGGCGGCCGCTCGAGGGGGATCCACTAGTTCTAGA

GCGGCCGCTTCGAGCAGACATGATAAGATACATTGATGAGTTTGGACAAA

CCACAACTAGAATGCAGTGAAAAAAATGCTTTATTTGTGAAATTTGTGAT

GCTATTGCTTTATTTGTAACCATTATAAGCTGCAATAAACAAGTTAACAA

CAACAATTGCATTCATTTTATGTTTCAGGTTCAGGGGGAGATGTGGGAGG

TTTTTTAAAGCAAGTAAAACCTCTACAAATGTGGTAAAATCGCGAAGACA

AGTGGCCAGAAAGGGCCGGGCGGAAGAGCCCTCGACAGACTGACCCTAAA

GCAAGACGAGGCAAGGCCAGTCCAGAATACCAGAGTGG

Nanog
Nanog gRNA:

(SEQ ID NO: 20)
GTATGAGACTTACGCAACATC

Nanog genomic region:

(SEQ ID NO: 21)
GCAGCCTTACGTACAGTTGCAGCAAAACTTCTCTGCCAGTGATTTGGAGG

TGAATTTGGAAGCCACTAGGGAAAGCCATGCGCATTTTAGCACCCCACAA

GCCTTGGAATTATTCCTGAACTACTCTGTGACTCCACCAGGTGAAATATG

AGACTTACGCAACATCTGGGCTTAAAGTCAGGGCAAAGCCAGGTTCCTTC

CTTCTTCCAAATATTTTCATAttttttttaaagatttatttattcattat atgtaagtacactgtagctgtcttca

Nanog GFP fusion:
(SEQ ID NO: 22)
GCAGCCTTACGTACAGTTGCAGCAAAACTTCTCTGCCAGTGATTTGGAGG

TGAATTTGGAAGCCACTAGGGAAAGCCATGCGCATTTTAGCACCCCACAA

GCCTTGGAATTATTCCTGAACTACTCTGTGACTCCACCAGGTGAAATAGT

GAGCAAGGGCGAGGAGCTGTTCACCGGGGTGGTGCCCATCCTGGTCGAGC

TGGACGGCGACGTAAACGGCCACAAGTTCAGCGTGTCCGGCGAGGGCGAG

GGCGATGCCACCTACGGCAAGCTGACCCTGAAGTTCATCTGCACCACCGG

CAAGCTGCCCGTGCCCTGGCCCACCCTCGTGACCACCCTGACCTACGGCG

TGCAGTGCTTCAGCCGCTACCCCGACCACATGAAGCAGCACGACTTCTTC

AAGTCCGCCATGCCCGAAGGCTACGTCCAGGAGCGCACCATCTTCTTCAA

GGACGACGGCAACTACAAGACCCGCGCCGAGGTGAAGTTCGAGGGCGACA

CCCTGGTGAACCGCATCGAGCTGAAGGGCATCGACTTCAAGGAGGACGGC

AACATCCTGGGGCACAAGCTGGAGTACAACTACAACAGCCACAACGTCTA

TATCATGGCCGACAAGCAGAAGAACGGCATCAAGGTGAACTTCAAGATCC

GCCACAACATCGAGGACGGCAGCGTGCAGCTCGCCGACCACTACCAGCAG

AACACCCCCATCGGCGACGGCCCCGTGCTGCTGCCCGACAACCACTACCT

GAGCACCCAGTCCGCCCTGAGCAAAGACCCCAACGAGAAGCGCGATCACA

TGGTCCTGCTGGAGTTCGTGACCGCCGCCGGGATCACTCTCGGCATGGAC

GAGCTGTACAAGTAAAGCGGCCGCAATTCACTCCTCAAACATCTGGGCTT

AAAGTCAGGGCAAAGCCAGGTTCCTTCCTTCTTCCAAATATTTTCATAtt tttttaaagatttatttattcattatatgtaagtacactgtagctgtct tca Rpp25
Rpp25 gRNA:
(SEQ ID NO: 23)
GCTCAGAGGCGAGAATTCTC Rpp25 genomic region:
(SEQ ID NO: 24)
CTCAGTCCTGGTCCTTCGTCCCCTCCTACGGTGTCGACGTCCAAGAGGAG

CCTGGGGGAATCTGCTGCTGAAGAAGGCACCGCTAAGCGGTCTCAGCCTG

AGCCAGAGGCTGAGAATGAGGACAGGACCGCCTGAGAATTCTCGCCTCTG

AGCCACCCAGACCGACTGAATCATATATCTTCAACACTCCTGCATACCTT

TCAACACACGCACCTTTCATACCTGGGTTTTAAGGGGCCCATGTTCCTG

Rpp25 GFP fusion:
(SEQ ID NO: 25)
CTCAGTCCTGGTCCTTCGTCCCCTCCTACGGTGTCGACGTCCAAGAGGAG

CCTGGGGGAATCTGCTGCTGAAGAAGGCACCGCTAAGCGGTCTCAGCCTG

AGCCAGAGGCTGAGAATGAGGACAGGACCGCCGTGAGCAAGGGCGAGGAG

CTGTTCACCGGGGTGGTGCCCATCCTGGTCGAGCTGGACGGCGACGTAAA

CGGCCACAAGTTCAGCGTGTCCGGCGAGGGCGAGGGCGATGCCACCTACG

GCAAGCTGACCCTGAAGTTCATCTGCACCACCGGCAAGCTGCCCGTGCCC

TGGCCCACCCTCGTGACCACCCTGACCTACGGCGTGCAGTGCTTCAGCCG

CTACCCCGACCACATGAAGCAGCACGACTTCTTCAAGTCCGCCATGCCCG

AAGGCTACGTCCAGGAGCGCACCATCTTCTTCAAGGACGACGGCAACTAC

AAGACCCGCGCCGAGGTGAAGTTCGAGGGCGACACCCTGGTGAACCGCAT

CGAGCTGAAGGGCATCGACTTCAAGGAGGACGGCAACATCCTGGGGCACA

AGCTGGAGTACAACTACAACAGCCACAACGTCTATATCATGGCCGACAAG

CAGAAGAACGGCATCAAGGTGAACTTCAAGATCCGCCACAACATCGAGGA

CGGCAGCGTGCAGCTCGCCGACCACTACCAGCAGAACACCCCCATCGGCG

ACGGCCCCGTGCTGCTGCCCGACAACCACTACCTGAGCACCCAGTCCGCC

CTGAGCAAAGACCCCAACGAGAAGCGCGATCACATGGTCCTGCTGGAGTT

CGTGACCGCCGCCGGGATCACTCTCGGCATGGACGAGCTGTACAAGTAAA

GCGGCCGCAATTCACTCCTCACTGAGCCACCCAGACCGACTGAATCATAT

ATCTTCAACACTCCTGCATACCTTTCAACACACGCACCTTTCATACCTGG

GTTTTAAGGGGCCCATGTTCCTG

MERA gRNA Library Design

We used the following algorithm to design gRNAs:
1. Determine region of interest for guide RNA design
2. Find all GG sequences on both the forward and reverse strand
3. Design guide RNA in the following format. Guide RNAs should have 19-20 bp of homology to the genome immediately preceding the NGG "PAM" sequence:
   a. If the genome sequence is GNNNNNNNNNNNNNNNNNNN NGG ($GN_{19}NGG$), the guide RNA sequence should be GNNNNNNNNNNNNNNNNNNN ($GN_{19}$)
   b. If a is not satisfied but GNNNNNNNNNNNNNNNNNN NGG ($GN_{18}NGG$) is satisfied, the guide RNA sequence should be GNNNNNNNNNNNNNNNNNN ($GN_{18}$)
   c. If a and b are not satisfied, the guide RNA sequence should be GNNNNNNNNNNNNNNNNNNN ($GN_{20}$) where the genomic sequence is NNNNNNNNNNNNNNNNNNNN NGG ($N_{20}NGG$)—it does not matter if the first G is in the genome.
4. For guide RNA library design, each guide RNA sequence should be placed in the following template, which will be 98-100 bp depending on guide RNA class a-c. We ordered gRNA libraries of 3918 members from LC Sciences. TTATATATCTTGTGGAAAGGACGAAACACC[$GN_{18-20}$] GTTTAAGAGCTATGCTGGAA ACAGCATAGCAAGTT-TAAATAAGGCTAGT (SEQ ID NO: 26)

All libraries contained 10 gRNAs targeting the GFP open reading frame to serve as positive controls:

10 Positive Control gRNAs Targeting GFP:

1.
(SEQ ID NO: 27)
TTATATATCTTGTGGAAAGGACGAAACACCGGGCGAGGAGCTGTTCACCG

GTTTAAGAGCTATGCTGGAAACAGCATAGCAAGTTTAAATAAGGCTAGT 2.
(SEQ ID NO: 28)
TTATATATCTTGTGGAAAGGACGAAACACCGACCAGGATGGGCACCACCC

GTTTAAGAGCTATGCTGGAAACAGCATAGCAAGTTTAAATAAGGCTAGT 3.
(SEQ ID NO: 29)
TTATATATCTTGTGGAAAGGACGAAACACCGAGCTGGACGGCGACGTAAA

GTTTAAGAGCTATGCTGGAAACAGCATAGCAAGTTTAAATAAGGCTAGT 4.
(SEQ ID NO: 30)
TTATATATCTTGTGGAAAGGACGAAACACCGGCATCGCCCTCGCCCTCGC

GTTTAAGAGCTATGCTGGAAACAGCATAGCAAGTTTAAATAAGGCTAGT 5.
(SEQ ID NO: 31)
TTATATATCTTGTGGAAAGGACGAAACACCGCTTCAGGGTCAGCTTGCCG

TGTTTAAGAGCTATGCTGGAAACAGCATAGCAAGTTTAAATAAGGCTAGT 6.
(SEQ ID NO: 32)
TTATATATCTTGTGGAAAGGACGAAACACCGGGCACGGGCAGCTTGCCGG

GTTTAAGAGCTATGCTGGAAACAGCATAGCAAGTTTAAATAAGGCTAGT 7.
(SEQ ID NO: 33)
TTATATATCTTGTGGAAAGGACGAAACACCGGTCAGGGTGGTCACGAGGG

GTTTAAGAGCTATGCTGGAAACAGCATAGCAAGTTTAAATAAGGCTAGT 8.
(SEQ ID NO: 34)
TTATATATCTTGTGGAAAGGACGAAACACCGCTTCATGTGGTCGGGGTAG

GTTTAAGAGCTATGCTGGAAACAGCATAGCAAGTTTAAATAAGGCTAGT 9.
(SEQ ID NO: 35)
TTATATATCTTGTGGAAAGGACGAAACACCGACGTAGCCTTCGGGCATGG

GTTTAAGAGCTATGCTGGAAACAGCATAGCAAGTTTAAATAAGGCTAGT 10.
(SEQ ID NO: 36)
TTATATATCTTGTGGAAAGGACGAAACACCGGAGCGCACCATCTTCTTCA

GTTTAAGAGCTATGCTGGAAACAGCATAGCAAGTTTAAATAAGGCTAGT

MERA Screening

To amplify the gRNA pool for electroporation into target cells, we use NEBNext 2× MasterMix, as it is optimized for maintaining diversity in pooled PCRs. We use a single PCR to add HDRs on each side of the gRNA library:

0.25 uL gRNA library (1% of the library) in a 500 uL NEBNext reaction (250 uL 2×NEBNext MasterMix, 1.25 uL of each primer or 25 of 10 uM primer mix)

gRNALib_HDR_fw
(SEQ ID NO: 37)
TGTTTTAAAATGGACTATCATATGCTTACCGTAACTTGAAAGTATTTCGA

TTTCTTGGCTTTATATATCTTGTGGAAAGGACGAAACACC gRNALib_HDR_rv
(SEQ ID NO: 38)
CTCGGTGCCACTTTTTCAAGTTGATAACGGACTAGCCTTATTTAAACTTG

CTATGCTGTT 35 cycles of 3-step PCR (98 for 10s, 62 for 30s, 72 for 30s).

We test ~2 uL, expecting 189 bp band.

We MinElute PCR purify the product using 2 columns (250 uL of PCR product per column).

The expected gRNA with HDR sequence is:

(SEQ ID NO: 39)
TGTTTTAAAATGGACTATCATATGCTTACCGTAACTTGAAAGTATTTCGA

TTTCTTGGCTTTATATATCTTGTGGAAAGGACGAAACACCGGGCGAGGAG

CTGTTCACCGGTTTAAGAGCTATGCTGGAAACAGCATAGCAAGTTTAAAT

AAGGCTAGTCCGTTATCAACTTGAAAAAGTGGCACCGAG

We then co-electroporate mESC that have ROSA dummy gRNA and locus-specific GFP with Cas9, guide RNA that cleaves the dummy gRNA, and purified homology arm-containing gRNA library. Library diversity is important here—we aim to have >10^6 cells survive selection to have adequate diversity and thus we start with a ~80% confluent 15 cm plate of mESC with:

25 ug p2T CBh Cas9 BlastR 25 ug p2T U6sgU6sgIhh-FE HygR (p2T sg60 HygR)

MinElute-purified gRNA library PCR product from 500 uL PCR reaction

Vacuum concentrate mix to <40 uL total volume and use 200 uL electroporation buffer We plated electroporated cells onto a 15-cm plate adding 7.5 uM Y-27632 to media for the 24 hours after electroporation to boost survival, which helps since library diversity is key. We transiently select with 10 ug/mL Blasticidin from 24-72 hours after electroporation (total of 48 hours of selection).

We expanded these cells, making sure to freeze down aliquots (usually passage beginning 4-6 days after electroporation) but maintain library diversity by not splitting at less than 1/10.

We then flow cytometrically isolated GFP(low) and GFP-$^{neg}$ cells using a FACSAria (BD Biosciences). We sorted between 1-2 weeks after electroporation. During the trypsinization that will be used for flow cytometry, we performed genomic DNA isolation on ~1/3-1/5 of the cells to serve as the bulk genomic DNA control for gRNA incorporation. We performed a first sort where we collected one combined GFP(low)/neg population, grew these cells for 3-4 additional days in culture, then re-sorted, this time separating GFP(low) and GFP$^{neg}$ cells when possible (for Tdgf1 and Zfp42 screens). After the second sort, we expanded the GFP(low) and GFP$^{neg}$ pools for 3-4 additional days before collecting genomic DNA. If populations were still impure, they were sorted a third time, grown for 3-4 days, and then split for genomic DNA isolation.

We collected genomic DNA from bulk and sorted populations using Purelink Genomic DNA isolation kit (Life Technologies)

We then proceeded to a homemade, PCR-based library prep on all populations.

We use a 3-step PCR-based library prep.

PCR1 exclusively amplifies gRNAs in the ROSA locus in the population (bulk or sorted). This is important because even weeks after electroporation, unincorporated gRNA homology constructs can still be found in cells. We perform 15 cycles of PCR1 to enrich ROSA-locus gRNAs away from unincorporated ones. PCR2 and PCR3 add first half and then the entire Illumina paired-end sequencing primers. In PCR2, a sample barcode is introduced between the gRNA and the PE1 primer, which allows sample multiplexing in a MiSeq lane.

PCR1: We used up to 16 ug of genomic DNA in up to an 800 uL NEBNext reaction, keeping a ratio of <20 ng genomic DNA per uL of PCR reaction to avoid template "poisoning". We typically used ½ of the genomic DNA isolated from cells We used the following primers at 500 nM:

```
        082214_gRNA_upstream_fw
                                  (SEQ ID NO: 40)
        TTGTGGAAAGGACGAAACACC 8. 091514_ROSA_downstream_rv
                                  (SEQ ID NO: 9)
        GGGAGGGGAGTGTTGCAATA
```

We performed 15 cycles of 3-step PCR (98 for 10s, 60 for 30s, 72 for 30s).
The product is 576 bp (and a mix of gRNAs):

```
                                                      (SEQ ID NO: 41)
TTGTGGAAAGGACGAAACACC[GN18-20]

GTTTAAGAGCTATGCTGGAAACAGCATA

GCAAGTTTAAATAAGGCTAGTCCGTTATCAACTTGAAAAAGTGGCACCGA

GTCGGTGCTTTTTTGTTTTAGAGCTAGAAATAGCAAGTTAAAATAAGGCT

AGTCCGTTTTTAGCGCGTGCGCCAATTCTGCAGACAAATGGCTCTAGAGG

TACGGCCGCTTCGAGCAGACATGATAAGATACATTGATGAGTTTGGACAA

ACCACAACTAGAATGCAGTGAAAAAAATGCTTTATTTGTGAAATTTGTGA

TGCTATTGCTTTATTTGTAACCATTATAAGCTGCAATAAACAAGTTAACA

ACAACAATTGCATTCATTTTATGTTTCAGGTTCAGGGGGAGATGTGGGAG

GTTTTTTAAAGCAAGTAAAACCTCTACAAATGTGGTAAAATCGCGATGCA

GATCACGAGGGAAGAGGGGAAGGGATTCTCCCAGGCCCAGGGCGGTCCT

CAGAAGCCAGGAGGCAGCAGAGAACTCCCAGAAAGGTATTGCAACACTCC

CCTCCC
```

We performed PCR purification in a single column per sample, eluting in 45 uL of dH2O. We used 0.1 uL of this purified product in a 20 uL qPCR with:

```
        082214_gRNA_upstream_fw
                                  (SEQ ID NO: 42)
        TTGTGGAAAGGACGAAACACC 020515_gRNA_qPCR_rv
                                  (SEQ ID NO: 43)
        GCCTTATTTAAACTTGCTATGCTGT
```

To determine cycle count for PCR2, we divided the Ct by 2. Typical Ct values are 9-14.
PCR 2:
We used 23 uL of sample in a 50 uL NEBNext reaction. We used the following primers at 500 nM and different barcoded PE1 primer for each sample to be multiplexed:

```
        101714_gRNAPE1_BcO
                                  (SEQ ID NO: 44)
        CTCTTTCCCTACACGACGCTCTTCCGATCTaactc

TTGTGGAAAGGACGAAACACC

101714_gRNAPE1_BcP
                                  (SEQ ID NO: 45)
        CTCTTTCCCTACACGACGCTCTTCCGATCTctgga

TTGTGGAAAGGACGAAACACC

101714_gRNAPE1_BcQ
                                  (SEQ ID NO: 46)
        CTCTTTCCCTACACGACGCTCTTCCGATCTggact

TTGTGGAAAGGACGAAACACC

101714_gRNAPE1_BcR
                                  (SEQ ID NO: 47)
        CTCTTTCCCTACACGACGCTCTTCCGATCTtctgc

TTGTGGAAAGGACGAAACACC

101714_gRNAPE1_BcS
                                  (SEQ ID NO: 48)
        CTCTTTCCCTACACGACGCTCTTCCGATCTaaccg

TTGTGGAAAGGACGAAACACC

101714_gRNAPE1_BcT
                                  (SEQ ID NO: 49)
        CTCTTTCCCTACACGACGCTCTTCCGATCTctctg

TTGTGGAAAGGACGAAACACC

101714_gRNAPE1_BcU
                                  (SEQ ID NO: 50)
        CTCTTTCCCTACACGACGCTCTTCCGATCTggtaa

TTGTGGAAAGGACGAAACACC

101714_gRNAPE1_BcV
                                  (SEQ ID NO: 51)
        CTCTTTCCCTACACGACGCTCTTCCGATCTaagct

TTGTGGAAAGGACGAAACACC

101714_gRNAPE1_BcW
                                  (SEQ ID NO: 52)
        CTCTTTCCCTACACGACGCTCTTCCGATCTtcgtc

TTGTGGAAAGGACGAAACACC

101714_gRNAPE1_BcX
                                  (SEQ ID NO: 53)
        CTCTTTCCCTACACGACGCTCTTCCGATCTccaat

TTGTGGAAAGGACGAAACACC

101714_gRNAPE1_BcY
                                  (SEQ ID NO: 54)
        CTCTTTCCCTACACGACGCTCTTCCGATCTgcgta

TTGTGGAAAGGACGAAACACC

101714_gRNAPE1_BcZ
                                  (SEQ ID NO: 55)
        CTCTTTCCCTACACGACGCTCTTCCGATCTgagc

TTGTGGAAAGGACGAAACACC 9. 010715_LibrarygRNA_PE2
                                  (SEQ ID NO: 56)
        CATTCCTGCTGAACCGCTCTTCCGATCTGCCTTATT

TAAACTTGCTATGCTGT
```

We performed 3-step PCR (98 for 10s, 60 for 30s, 72 for 30s) using the number of cycles determined from the qPCR.
An example product with Barcode 0 is 150 bp:

```
                                                      (SEQ ID NO: 57)
CTCTTTCCCTACACGACGCTCTTCCGATCTaactcTTGTGGAAAGGACGN 18-20GTTTAAGAGCTATGCTGGAAACAGCATAGCAAGTTTAAATAAGGC

AGATCGGAAGAGCGGTTCAGCAGGAATG
```

We performed PCR purification in a single column per sample, eluting in 45 uL of dH2O. We used 0.1 uL of this purified product in a 20 uL qPCR with:

```
082214_gRNA_upstream_fw
                                          (SEQ ID NO: 42)
TTGTGGAAAGGACGAAACACC 020515_gRNA_qPCR_rv
                                          (SEQ ID NO: 43)
GCCTTATTTAAACTTGCTATGCTGT
```

We used an equivalent number of cycles of PCR3 as the Ct count.

PCR 3:

Use 23 uL of sample in a 50 uL NEBNext reaction. Use the following primers at 500 nM:

```
061813_PE1
                                          (SEQ ID NO: 58)
AATGATACGGCGACCACCGAGATCTACACTCTTTCCCTACACGACGCTCT

TCCGATCT

061813_PE2
                                          (SEQ ID NO: 59)
CAAGCAGAAGACGGCATACGAGATCGGTCTCGGCATTCCTGCTGAACCGC

TCTTCCGATCT
```

We performed 3-step PCR (98 for 10s, 65 for 30s, 72 for 30s) using the number of cycles determined from the qPCR.

We performed PCR purification in a single column per sample, eluting in 30 uL of Elution buffer. The expected product is: PE BcO (211 bp)

```
                                          (SEQ ID NO: 60)
AATGATACGGCGACCACCGAGATCTACACTCTTTCCCTACACGACGCTCT

TCCGATCTaactcTTGTGGAAAGGACGAAACACCGN18-20

GTTTAAGAGCTATGCTGGAAACAG

CATAGCAAGTTTAAATAAGGCAGATCGGAAGAGCGGTTCAGCAGGAATGC

CGAGACCGATCTCGTATGCCGTCTTCTGCTTG
```

Validation of MERA Hit gRNAs

We validated hit gRNAs from the MERA screens using the Self-Cloning CRISPRCas9 (scCRISPR) protocol we have recently developed (Arbab et al. Stem Cell Reports, 2015). The scCRISPR protocol enables testing of gRNAs simply by ordering a single oligonucleotide and PCR amplifying it to form a homology fragment. As a result, testing of gRNAs can be performed at <⅙ of the cost of constructing a conventional plasmid gRNA with only two hours of preparation from when oligonucleotides arrive to when they can be tested in mESCs.

Briefly, mESCs were co-transfected using Lipofectamine 3000 with a Cas9 plasmid, a self-cleaving gRNA plasmid, and a homology fragment to replace the cleaved gRNA plasmid with an gRNA sequence of interest. After transient drug selection and growth for 6-9 days after transfection, mESCs were analyzed for fluorescence using a BD Accuri C6 flow cytometer. The oligonucleotides to test Tdgf1 hit gRNAs, control gRNAs, as well as the scCRISPR stock primers are listed below:

```
gRNA_60bp_fw
                                          (SEQ ID NO: 61)
TAACTTGAAAGTATTTCGATTTCTTGGCTTTATATATCTTGTGGAAAGGA

CGAAACACCG gRNA_60bp_rv
                                          (SEQ ID NO: 62)
GTTGATAACGGACTAGCCTTATTTAAACTTGCTATGCTGTTTCCAGCATA

GCTCTTAAAC gRNAHDR_Ext_fw
                                          (SEQ ID NO: 63)
ATTTCTTGGGTAGTTTGCAGTTTTAAAATTATGTTTTAAAATGGACTATC

ATATGCTTACCGTAACTTGAAAGTATTTCGATTTCTTGGC gRNAHDR_Ext_rv
                                          (SEQ ID NO: 64)
ATTTTAACTTGCTATTTCTAGCTCTAAAACAAAAAAGCACCGACTCGGTG

CCACTTTTTCAAGTTGATAACGGACTAGCCTTATTTAAAC gRNALib_HDRstep3_fw
                                          (SEQ ID NO: 65)
CGATACAAGGCTGTTAGAGAGATAATTAGAATTAATTTGACTGTAAACAC

AAAGATATTAGTACAAAATACGTGACGTAGAAAGTAATAA gRNAHDR_step3_rv
                                          (SEQ ID NO: 66)
TCAATGTATCTTATCATGTCTGCTCGATTTTAACTTGCTATTTCTAGCTC

TAAAACAAAA sgGFP4_60bp (positive control in GFP ORF)
                                          (SEQ ID NO: 67)
TGGAAAGGACGAAACACCGGCATCGCCCTCGCCCTCGC

GTTTAAGAGCTATGCTGGAAAC sgTdgfFU1_60bp
                                          (SEQ ID NO: 68)
TGGAAAGGACGAAACACCGAGTGAGATCCAGGTGATCC

GTTTAAGAGCTATGCTGGAAAC sgTdgfFU2_60bp
                                          (SEQ ID NO: 69)
GGAAAGGACGAAACACCGCAAACAGCTCCATACCCAAG

GTTTAAGAGCTATGCTGGAAAC sgTdgfFU3_60bp
                                          (SEQ ID NO: 70)
TGGAAAGGACGAAACACCGCAAGCACCACCCTACTTGG

GTTTAAGAGCTATGCTGGAAAC sgTdgfFU4_60bp
                                          (SEQ ID NO: 71)
GGAAAGGACGAAACACCGCCATCCCCTGCCGGTCTACA

GTTTAAGAGCTATGCTGGAAAC sgTdgfFU5_60bp
                                          (SEQ ID NO: 72)
TGGAAAGGACGAAACACCGGGGGTGAGGGCAATTGG

GTTTAAGAGCTATGCTGGAAACA sgTdgfFU6_60bp
                                          (SEQ ID NO: 73)
GGAAAGGACGAAACACCGAATTCCTGCTTCTTACCACG

GTTTAAGAGCTATGCTGGAAAC sgTdgfFU8_60bp
                                          (SEQ ID NO: 74)
TGGAAAGGACGAAACACC
```

```
GAAACAAAAGCCACAAACA GTTTAAGAGCTATGCTGGAAACA sgTdgfFU9_60bp
                                        (SEQ ID NO: 75)
GGAAAGGACGAAACACC

GATGGTTAGCATTCCGGGTGC GTTTAAGAGCTATGCTGGAAAC sgTdgfFU10_60bp
                                        (SEQ ID NO: 76)
GGAAAGGACGAAACACC

GTTATGGGCAAGCTGTGTCCC GTTTAAGAGCTATGCTGGAAAC sgTdgfFU11_60bp
                                        (SEQ ID NO: 77)
TGGAAAGGACGAAACACC GGGGAAGTGACTAAGACTG

GTTTAAGAGCTATGCTGGAAACA sgTdgfFU12_60bp
                                        (SEQ ID NO: 78)
TGGAAAGGACGAAACACC GCCATAGTTTTCCAGAAAG

GTTTAAGAGCTATGCTGGAAACA sgTdgfFU13_60bp
                                        (SEQ ID NO: 79)
GGAAAGGACGAAACACC

GTCTGAAGGAGACAATGACAA GTTTAAGAGCTATGCTGGAAAC sgTdgfFU14_60bp
                                        (SEQ ID NO: 80)
GGAAAGGACGAAACACC GCCCATCCCCTGTCACTCT

GAGTTCGTTTAAGAGCTATGCTGGAAAC sgTdgfFU15_60bp
                                        (SEQ ID NO: 81)
GGAAAGGACGAAACACC

GATAATTCCTTTAGTCTACAT GTTTAAGAGCTATGCTGGAAAC sgTdgfFU16_60bp
                                        (SEQ ID NO: 82)
TGGAAAGGACGAAACACC

GGGATTCTGGGAAACATTG GTTTAAGAGCTATGCTGGAAAC sgTdgfFU17_60bp
                                        (SEQ ID NO: 83)
GGAAAGGACGAAACACC

GCTCTCAGGACTTGTCCACAC GTTTAAGAGCTATGCTGGAAAC sgTdgfFU18_60bp
                                        (SEQ ID NO: 84)
GGAAAGGACGAAACACC

GTTTCCTAAGCCCTAGCTGGA GTTTAAGAGCTATGCTGGAAAC sgTdgfFU19_60bp
                                        (SEQ ID NO: 85)
GGAAAGGACGAAACACC

GTTAGAAATTAGTGCAGTGTT GTTTAAGAGCTATGCTGGAAAC sgTdgfFU20_60bp
                                        (SEQ ID NO: 86)
GGAAAGGACGAAACACC GAATCTTCCCAATTGTCTCCT

GTTTAAGAGCTATGCTGGAAAC sgTdgfFU21_60bp
                                        (SEQ ID NO: 87)
TGGAAAGGACGAAACACC

GTCAACTAAACCAACACTTA GTTTAAGAGCTATGCTGGAAAC

TdgfFU25_60bp
                                        (SEQ ID NO: 88)
GGAAAGGACGAAACACC

GTCTTTCAAAACAAGACCCAA GTTTAAGAGCTATGCTGGAAAC

TdgfFU26_60bp
                                        (SEQ ID NO: 89)
GGAAAGGACGAAACACC

GTTTCTGTCCAGGACACTGAT GTTTAAGAGCTATGCTGGAAAC

TdgfFU27_60bp
                                        (SEQ ID NO: 90)
GGAAAGGACGAAACACC

GAAAAACTAGTCAACATTCC GTTTAAGAGCTATGCTGGAAAC

TdgfFU28_60bp
                                        (SEQ ID NO: 91)
GGAAAGGACGAAACACC

GCTGTGAGCCCTTTGTAAGGA GTTTAAGAGCTATGCTGGAAAC

TdgfFU29_60bp
                                        (SEQ ID NO: 92)
GGAAAGGACGAAACACC

GACTGCATCCACAGACTGGGC GTTTAAGAGCTATGCTGGAAAC

TdgfFU30_60bp
                                        (SEQ ID NO: 93)
GGAAAGGACGAAACACC

GCCCTCACCCCTAGGGTTTC GTTTAAGAGCTATGCTGGAAAC sgTdgfCt1FU1_60bp
                                        (SEQ ID NO: 94)
TGGAAAGGACGAAACACC GTTTCTTCATTGTCAGAGA

GTTTAAGAGCTATGCTGGAAACA sgTdgfCt1FU2_60bp
                                        (SEQ ID NO: 95)
GGAAAGGACGAAACACC GTTCTTCCTTGCTTTCTTTTG

GTTTAAGAGCTATGCTGGAAAC

TdgfFU43_60bp
                                        (SEQ ID NO: 96)
TGGAAAGGACGAAACACC GAATTTTCCTTCATCATTTT

GTTTAAGAGCTATGCTGGAAAC

TdgfFU44_60bp
                                        (SEQ ID NO: 97)
GGAAAGGACGAAACACC

GTTCAGCACAGCAGATGCTCT GTTTAAGAGCTATGCTGGAAAC

TdgfFU45_60bp
                                        (SEQ ID NO: 98)
TGGAAAGGACGAAACACC

GAACAGCTTTTTAGATGTGA GTTTAAGAGCTATGCTGGAAAC

TdgfFU47_60bp
                                        (SEQ ID NO: 99)
TGGAAAGGACGAAACACC

GATTTAGAATCCCCTAAGGA GTTTAAGAGCTATGCTGGAAAC

TdgfFU49_60bp
                                        (SEQ ID NO: 100)
GGAAAGGACGAAACACC
```

```
GTCCGAGACTGCGGCTCTTAC GTTTAAGAGCTATGCTGGAAAC

TdgfFU50_60bp
                                    (SEQ ID NO: 101)
GGAAAGGACGAAACACC

GTCGGATGACCTGAGTAGAGC GTTTAAGAGCTATGCTGGAAAC
```

Deep Sequencing of MERA Hotspots

We used the scCRISPR method to induce mutations at eight individual gRNA sites in separate batches of mESCs. We then pooled batches with gRNAs in each of four hotspots. GFP$^{pos}$ and GFP$^{medium/-}$ populations were flow cytometrically sorted from these five pools, all giving >90% purity. Genomic DNA was isolated from these populations using the Purelink Genomic DNA mini kit. PCR-based library prep was performed using four successive PCRs to amplify and add paired-end Illumina sequencing primers and multiplexing barcodes to desired genomic regions. Paired-end MiSeq was performed on the prepared libraries using 150+150 nt paired-end reads. Sequenced regions with Illumina paired-end primers and n's to denote multiplexing barcodes along with all primers used for this protocol are shown below:

```
Tdgf1 enhancer region
                                    (SEQ ID NO: 102)
AATGATACGGCGACCACCGAGATCTACACTCTTTCCCTACACGACGCTCT TCCGATCTnnnnn GCCGAAAGGATGGGAGTACTAAGC 10.
                                    (SEQ ID NO: 103)
ACGCCCAGTCTCTCTACTCCCCCCCACCCCCATCCCCTGTCACTCTGAGT

TTCCAGCCACTTTTCCAGTTCCTGAAACCCTAGGGGGTGAGGGGCAATTG

GTGGTGGTGGTGGGGGGGGGGAATCTGCTATTTCCGAGAAGGCTGGGCCT

CCTTCATTAACAAGCTAATGGCTGATTTCACTGAGACCTTGACA

TGGATGCAGGTCGAAAGGCCTnnnnnAGATCGGAAGAGCGGTTCAGCAGG

AATGCCGAGACCGATCTCGTATGCCGTCTTCTGCTTG sgTdgfFU5_60bp
                                    (SEQ ID NO: 104)
TGGAAAGGACGAAACACCGGGGGTGAGGGGCAATTGGGTTTAAGAGCTAT

GCTGGAAACA

11. TdgfFU30_60bp
                                    (SEQ ID NO: 105)
GGAAAGGACGAAACACC

GCCCTCACCCCCTAGGGTTTC GTTTAAGAGCTATGCTGGAAAC 12. 042115_TdgfFU30_up_fw
                                    (SEQ ID NO: 106)
ACGCCCAGTCTCTCTACTCCCC 13. 060915_TdgfFU30_dwn_rv
                                    (SEQ ID NO: 107)
TGTCAAGGTCTCAGTGAAATCAGCCA 14. 042915_TdgfFU30_ScaRO_fw
                                    (SEQ ID NO: 108)
CGAAAGGATGGGAGTACTAAGCT

ACGCCCAGTCTCTCTACTCCCC 15. 060915_TdgfFU30_IntPri_rv
                                    (SEQ ID NO: 109)
GGCCTTTCGACCTGCATCCA

TGTCAAGGTCTCAGTGAAATCAGCCA

16. Tdgf1 URE region
                                    (SEQ ID NO: 110)
AATGATACGGCGACCACCGAGATCTACACTCTTTCCCTACACGACGCTCT TCCGATCTnnnnn GCCGAAAGGATGGGAGTACTAAGCT 17.
                                    (SEQ ID NO: 111)
CCAAATGGGCCAAGCAAAACACAGCCAGTGAGACAGGCCTGCACCCGGAA

TGCTAACCATCAAGAGTGGATTCCGGGAGAGGGGCAACCTGGTTCAACCA

GCGACTCACAGATGAGACTGTGAGCCCTTTGTAAGGAAGGACTGTCTGTA

GACTGAATGCGAGCTGAGCTCACGTGTCACTGGCCACAGAGGTCCAGCCC

AGTCTGTGGATGCAGTGGAGTCCAGGAAGGGCTTTCTCTGGCTTTTGTAG

TGGGACCG

TGGATGCAGGTCGAAAGGCCTnnnnnAGATCGGAAGAGCGGTTCAGCAGG

AATGCCGAGACCGATCTCGTATGCCGTCTTCTGCTTG sgTdgfFU9_60bp
                                    (SEQ ID NO: 112)
GGAAAGGACGAAACACC

GATGGTTAGCATTCCGGGTGC GTTTAAGAGCTATGCTGGAAAC

TdgfFU29_60bp
                                    (SEQ ID NO: 113)
GGAAAGGACGAAACACC

GACTGCATCCACAGACTGGGC GTTTAAGAGCTATGCTGGAAAC

060915_TdgfFU9_up_fw
                                    (SEQ ID NO: 114)
CCAAATGGGCCAAGCAAAACACAG 021915_TdgfFU9_dwn_rv
                                    (SEQ ID NO: 115)
CGGTCCCACTACAAAAGCCAGAGAA 060915_TdgfFU9_ScaRO_fw
                                    (SEQ ID NO: 116)
CGAAAGGATGGGAGTACTAAGCT

CCAAATGGGCCAAGCAAAACACAG

030715_TdgfFU9_IntPri_rv
                                    (SEQ ID NO: 117)
GGCCTTTCGACCTGCATCCACGGTCCCACTACAAAAGCCAGAGAA Zfp42 Enhancer region
                                    (SEQ ID NO: 118)
AATGATACGGCGACCACCGAGATCTACACTCTTTCCCTACACGACGCTCT TCCGATCTnnnnn GCCGAAAGGATGGGAGTACTAAGC

AGCGGGGTGGTAGCTCACAAGACCAGGTAGGACGGATATGGCTTTGCGCA

GGCAATTAGTTTCTAAGAGCTCTCATTCAGTGAATGTGAACAGTGCCTTT

TACAAAAGATGCTTGGGTGAAAGGACAGAGGAAGGTCGAGGGGGTGTGGC

TTTGAGCAGGCAATTGCTCCCCAGAGCTCAGATTTTATGAATGTGAACA

GTACCCTTTTAAAAAGAGGCTAGGGTGTAGGCA

TGGATGCAGGTCGAAAGGCCTnnnnnAGATCGGAAGAGCGGTTCAGCAGG

AATGCCGAGACCGATCTCGTATGCCGTCTTCTGCTTG
```

18. sgZfpFU11_60bp
(SEQ ID NO: 119)
TGGAAAGGACGAAACACC GTGGCTTTGAGCAGGCAAT GTTTAAGAGCTATGCTGGAAACA 19. sgZfpFU36_60bp
(SEQ ID NO: 120)
TGGAAAGGACGAAACACC GGACGGATATGGCTTTGCGC GTTTAAGAGCTATGCTGGAAAC 20. 060915_ZfpFU11_dwn_rv
(SEQ ID NO: 121)
TGCCTACACCCTAGCCTCTTTT 21. 060915_ZfpFU11_IntPri_rv
(SEQ ID NO: 122)
GGCCTTTCGACCTGCATCCATGCCTACACCCTAGCCTCTTTT 22. 061815_ZfpFU11_up_fw
(SEQ ID NO: 175)
TGGTAGCTCACAAGACCAGGT 23. 061815_ZfpFU11_ScaRO_fw
(SEQ ID NO: 123)
CGAAAGGATGGGAGTACTAAGCTTGGTAGCTCACAAGACCAGGT Zfp42 URE region
(SEQ ID NO: 124)
AATGATACGGCGACCACCGAGATCTACACTCTTTCCCTACACGACGCTCT TCCGATCTnnnnn GCCGAAAGGATGGGAGTACTAAGC tggtgctcagacatacatgaaggcaaaatgtcatatacttaaaaaaaaaa AAtgaagacatagctcagtggctactcctccagaggaccctggtacccac atggcagctctaaacaccagttccaggggatccaatacccTCACATGCAG ACAAAACCAATGCACATAAAATAAAAACTAAAACACTAGAAAGTATTCCA AGTGTGACCCCTCAATACCTAGCCTCTTTTCCATGTCCTCTACCTTTGCT ATTCCACCTACATCTTCGGGGAGAAGAGACAGAAGGGCCACGCTAGACAC ATAAAATCCCATTTTCTAGGCCTCAAAATCCAGATAGGAACATCTTGTAA CTTCTAGAGACTTTTTCTCGTGAAAGGAGCTCAGAGCAGACCCACCTTTA CAAGGAGAGCCAACCTTACCCTTCTGAGTGCTCTGAGGCTCCAGTCTGAA GAGCCTGCTCCCTAATCTCTGCATCTTCTGGTTGGATGCAGGTCGAAAGG CCTnnnnnAGATCGGAAGAGCGGTTCAGCAGGAATGCCGAGACCGATCTC GTATGCCGTCTTCTGCTTG 24. sgZfpFU4_60bp
(SEQ ID NO: 125)
TGGAAAGGACGAAACACC GCACTCAGAAGGGTAAGGT GTTTAAGAGCTATGCTGGAAACA 25. sgZfpFU34_60bp
(SEQ ID NO: 126)
TGGAAAGGACGAAACACC GGGTACCAGGGTCCTCTGG GTTTAAGAGCTATGCTGGAAACA 26. 042115_ZfpFU4_up_fw
(SEQ ID NO: 127)
tggtgctcagacatacatgaaggca 27. 042115_ZfpFU4_dwn_rv
(SEQ ID NO: 128)
ACCAGAAGATGCAGAGATTAGGGAGC 28. 042915_ZfpFU4_ScaRO_fw
(SEQ ID NO: 129)
CGAAAGGATGGGAGTACTAAGCTggtgctcagacatacatgaaggca 29. 042915_ZfpFU4_IntPri_rv
(SEQ ID NO: _)
GGCCTTTCGACCTGCATCCACCAGAAGATGCAGAGATTAGGGAGC 032014_PhrPE1_BcO
(SEQ ID NO: 130)
CTCTTTCCCTACACGACGCTCTTCCGATCTaactc GCCGAAAGGATGGGAGTACTAAGCT 032014_PhrPE1_BcP
(SEQ ID NO: 131)
CTCTTTCCCTACACGACGCTCTTCCGATCTctggaGCCGAAAGGATGGGA GTACTAAGCT 032014_PhrPE1_BcQ
(SEQ ID NO: 132)
CTCTTTCCCTACACGACGCTCTTCCGATCTggactGCCGAAAGGATGGGA GTACTAAGCT 032014_PhrPE1_BcR
(SEQ ID NO: 133)
CTCTTTCCCTACACGACGCTCTTCCGATCTtctgc GCCGAAAGGATGGGAGTACTAAGCT 061813_PhrPE1_BcS
(SEQ ID NO: 134)
CTCTTTCCCTACACGACGCTCTTCCGATCTaaccgGCCGAAAGGATGGGA GTACTAAGCT 061813_PhrPE1_BcT
(SEQ ID NO: 135)
CTCTTTCCCTACACGACGCTCTTCCGATCTctctg GCCGAAAGGATGGGAGTACTAAGCT 061813_PhrPE1_BcU
(SEQ ID NO: 136)
CTCTTTCCCTACACGACGCTCTTCCGATCTggtaaGCCGAAAGGATGGGA GTACTAAGCT 061813_PhrPE1_BcV
(SEQ ID NO: 137)
CTCTTTCCCTACACGACGCTCTTCCGATCTaagct GCCGAAAGGATGGGAGTACTAAGCT 021314_PhrPE1_BcW
(SEQ ID NO: 138)
CTCTTTCCCTACACGACGCTCTTCCGATCTtcgtc GCCGAAAGGATGGGAGTACTAAGCT 021314_PhrPE1_BcX
(SEQ ID NO: 139)
CTCTTTCCCTACACGACGCTCTTCCGATCTccaat GCCGAAAGGATGGGAGTACTAAGCT 021314_PhrPE1_BcY
(SEQ ID NO: 140)
CTCTTTCCCTACACGACGCTCTTCCGATCTgcgtaGCCGAAAGGATGGGA GTACTAAGCT 021314_PhrPE1_BcZ
(SEQ ID NO: 141)
CTCTTTCCCTACACGACGCTCTTCCGATCTtgagcGCCGAAAGGATGGGA GTACTAAGCT -continued 040914_IntPriPE2_BcA
(SEQ ID NO: 142)
CATTCCTGCTGAACCGCTCTTCCGATCT ACATCAGGCCTTTCGACCTGC

ATCCA

040914_IntPriPE2_BcB
(SEQ ID NO: 143)
CATTCCTGCTGAACCGCTCTTCCGATCT GCCTAAGGCCTTTCGACCTGC

ATCCA

040914_IntPriPE2_BcC
(SEQ ID NO: 144)
CATTCCTGCTGAACCGCTCTTCCGATCT TGGTCAGGCCTTTCGACCTGC

ATCCA

040914_IntPriPE2_BcD
(SEQ ID NO: 145)
CATTCCTGCTGAACCGCTCTTCCGATCT CACTGAGGCCTTTCGACCTGC

ATCCA

PE1
(SEQ ID NO: 58)
AATGATACGGCGACCACCGAGATCTACACTCTTTCCCTACACGACGCTCT

TCCGATCT

PE2
(SEQ ID NO: 59)
CAAGCAGAAGACGGCATACGAGATCGGTCTCGGCATTCCTGCTGAACCGC

TCTTCCG ATCT

Deletion and Repair of Tdgf1 Enhancer and URE Regions

Deletion and repair experiments were performed using scCRISPR. Clonal mESC lines with noted deletions and repair to wildtype were picked and sequence verified by Sanger sequencing. Repair was performed by cutting with a gRNA that will only cut in the deletion genotype and by co-electroporating a PCR-amplified repair template including the region to be replaced with 100-300 bp of homology on either end. Deletion and repair were performed both in Tdgf1-GFP mESCs as well as wildtype mESCs. In wildtype mESCs, RT-qPCR was performed using NEB M-MuLV Reverse Transcriptase and qPCR comparison with Actb and Gapdh as cDNA controls.

Tdgf1 enhancer deletion and repair:

chr9: 110,947,795-110,948,285 (wildtype genotype)
30.
(SEQ ID NO: 146)
TCCTGGTAAATAACTGAGCCCTGAAATTGCTTGCTTACTCTGTGAATGCT

TCCACAATGTTTTCCCAGAATCCCACCCCTGAACCTTCGTGTGTACTGAG

CCCCTCTCTCAGGACTTGTCCACACTGGCTGCAGCAAACATCTGTAGCTT

GGCGTCTGCTGACTCCTGATGTGAGAAATTCGTATTTGGTTGTTTGGATT

TGCATGTTTCGCTGTGTTACTGGTATCTGTATTCAGTTTCCTAAGCCCTA

GCTGGAGGGTCTGACTGTGCCCTAGAACTGGCTTCTTTGGTCCTTTGCTC

TGGAAAGTCCTTCCGGGCACCTTTCCTCCCAAAGCTGGCTTCCAGCTGTG

GCCTTGAACTGGAAAGCGCAGAGAGATAACGACTGCTCCACCCCAGAGTT

GATCTTTACTAACACTGGATTGTAAACTGCTTATTTTTTGTCTTTCACC

CCACTCCCCCTGGTTCCCAATGGGAGGTCTAAGCCTGCTCT

Deletion genotype:

31.
(SEQ ID NO: 147)
TCCTGGTAAATAACTGAGCCCTGAAATTGCTTGCTTACTCTGTGAATGCT

TCCACAACACTGGCTGCAGCAAACATCTGTAGCTTGGCGTCTGCTGACTC

CTGATGTGAGAAATTCGTATTTGGTTGTTTGGATTTGCATGTTTCGCTGT

GTTACTGGTATCTGTATTCAGTTTCCTAAGCCCTAGCTGGAGGGTCTGAC

TGTGCCCTAGAACTGGCTTCTTTGGTCCTTTGCTCTGGAAAGTCCTTCCG

GGCACCTTTCCTCCCAAAGCTGGCTTCCAGCTGTGGCCTTGAACTGGAAA

GCGCAGAGAGATAACGACTGCTCCACCCCAGAGTTGATCTTTACTAACAC

TGGATTGTAAACTGCTTATTTTTTGTCTTTCACCCCACTCCCCCTGGTT

CCCAATGGGAGGTCTAAGCCTGCTCT gRNAs used for deletion:

sgTdgfFU16_60bp
(SEQ ID NO: 82)
TGGAAAGGACGAAACACC

GGGATTCTGGGAAAACATTG GTTTAAGAGCTATGCTGGAAAC sgTdgfFU17_60bp
(SEQ ID NO: 83)
GGAAAGGACGAAACACC

GCTCTCAGGACTTGTCCACAC GTTTAAGAGCTATGCTGGAAAC gRNA used for repair to wildtype:

(SEQ ID NO: 148)
GGAAAGGACGAAACACCGTTTGCTGCAGCCAGTGTTG GTTTAAGAGCT

ATGCTGGAAACA

Primers used for homology-directed repair template and sequencing:

TdgfFU16_up_fw
(SEQ ID NO: 149)
TCCTGGTAAATAACTGAGCCCTGAAAT

TdgfFU16_dwn_rv
(SEQ ID NO: 150)
AGAGCAGGCTTAGACCTCCCA

32. Tdgf1 URE deletion and repair:

33. chr9: 110,933,942-110,934,053 (wildtype region)
34.
(SEQ ID NO: 151)
CCCCTTGGATGTGAGAACCTCAGGGTTCCAAGGACTCTCTTCTGGGAGTC

TGCCCAACTGCAAAAGGCTAGGTGGCTGACACTTGGAGATGGGGGTGGGA

GCAGATGCCACAGTCTTTTGACATGCCCACCAAAAGGCCATTTGGAAATA

AAGCTGCTTTGGTTGCCAGCAGAGCTCTTGTCTCAGAGGGGACCCTGGCA

GATGGCGGCGCGCCTGTTATCACGGGCATATCCCTGCTGATGTTCTTCCT

TCTTCGAAATAGAGCGTTTATTCAGCTCCAATTTGTTACCATGGGTTGTC

CCAAAATGATGAAGGAAAATTCAAGAGACTGCCAGGGGCCAGTTGGATTT

-continued

GAAACATTTGTATTCAGCACAGCAGATGCTCTCGGCTACAGAGAACAGCT
TTT 35.
36. Deletion genotype:

(SEQ ID NO: 152)
CCCCTTGGATGTGAGAACCTCAGGGTTCCAAGGACTCTCTTCTGGGAGTC

TGCCCAACTGCAAAAGGCTAGGTGGCTGACACTTGGAGATGGGGGTGGGA

GCAGATGCCACAGTCTTTTGACATGCCCACCAAAAGGCCATTTGGAAATA

AAGCTGCTTTGGTTGCCAGCAGAGCTCTTGTCTCAGAGGGGACCCTGGCA

GATGGCGGCGCGCCTGTTATTGAAGGAAAATTCAAGAGACTGCCAGGGGC

CAGTTGGATTTGAAACATTTGTATTCAGCACAGCAGATGCTCTCGGCTAC

AGAGAACAGCTTTT gRNAs used for deletion:

TdgfFU39_60bp
(SEQ ID NO: 153)
TGGAAAGGACGAAACACCGGCGGCGCGCCTGTTATCAC

GTTTAAGAGCTATGCTGGAAAC

TdgfFU40_60bp
(SEQ ID NO: 154)
TGGAAAGGACGAAACACC

GGGTTGTCCCAAAATGATGA GTTTAAGAGCTATGCTGGAAAC gRNA used for repair to wildtype:

(SEQ ID NO: 155)
GGAAAGGACGAAACACC GTTGAATTTTCCTTCAATAAC

GTTTAAGAGCTATGCTGGAAAC

Primers used for homology-directed repair and sequencing:

TdgfFU37_up_fw
(SEQ ID NO: 156)
CCCCTTGGATGTGAGAACCTC

TdgfFU37_dwn_rv
(SEQ ID NO: 157)
AAAAGCTGTTCTCTGTAGCCGAGAG

RT-qPCR primers:

Gapdh_qPCRfw
(SEQ ID NO: 158)
TTGATGGCAACAATCTCCAC

Gapdh_qPCRrv
(SEQ ID NO: 159)
CGTCCCGTAGACAAAATGGT

Actb_qPCRfw
(SEQ ID NO: 160)
ATGGAGGGGAATACAGCCC

Actb_qPCRrv
(SEQ ID NO: 161)
TTCTTTGCAGCTCCTTCGTT

Tdgf1_qPCR1_fw
(SEQ ID NO: 162)
CCTCCAACGTTTTTACGAGC

Tdgf1_qPCR1_rv
(SEQ ID NO: 163)
GGTCCAAATTCAAACGCACT

Tdgf1_qPCR2_fw
(SEQ ID NO: 164)
TTTTACGAGCCGTCGAAGAT

Tdgf1_qPCR2_rv
(SEQ ID NO: 165)
TCTGATGGCAAGGTCTCTCC

Analysis of Mutation and Deletion Efficiency in the Tdgf1-Adjacent Lrrc2 Promoter Region scCRISPR was used to perform mutation and deletion as noted in the text.

Lrrc2 promoter region:

(SEQ ID NO: 166)
atgtgggtcccagtagtcatattccacctggtgcctctggcctccgagtc atctgactggcccTTAGTGAACTTTgtggttagtcatgttgtgtgcacag tcaggaactagagagaaggctagtattcctagtgacttagtgtccgggat gttgccactgccactcacagtcagaatagggcttttctactcagttaaac actctcacagatacccagcagagccttccttaggggattctaaatccag tcaaattcacagtgaagatgaaccctcCAGTGCTCCGTAGCTGGGGCTGC

TGCGTAGCACATTTGCACACCGTGAGGACCATCAGTAGCCCAGGTTGGCC

GGAGTTTTAGCCTGCAGATGTGAGGCCACAAGCCAGGAGCCCTTGCCGCT

TGCTCTCCCACCAGCGAGAACCATTTAGTAATGTCCATGGAGATGGAAGG

CGGTGTTTATAACATTCATTCTTCTCTACATACATCGTGAAGGGAGGGAG

GTCAGGTGAGGGACATCAGGGATTTTCCTGGAAGAAAGCTTTGCTGGGCG

TTCATGTGACTCATGTTCCAGTAAGAGCCGCAGTCTCGGATGACCTGAGT

AGAGCAGGGTTATCTGGATGTGCTTGTGGGTGGAACCCCTTTGGAAGGGA

GGTAGGTAAGGGTGGGTGTATCCTCGCAGAGACGTAGAACTTCTGTGTGT

GGATGATGTTTCATCAGAGACTGTGAGCCGAGCCGGATGCTAAACAcagt agttctcaaccttcctaatgctacaaccctcatgctgtggtgacccccag ccataca gRNAs:

TdgfFU46_60bp
(SEQ ID NO: 167)
GGAAAGGACGAAACACC

GCTCTGCTGGGGTATCTGTGA GTTTAAGAGCTATGCTGGAAAC

Negative in MERA whose PAM sequence is actually NAG in the Tdgf1-GFP mESC line.

TdgfFU47_60bp
(SEQ ID NO: 168)
TGGAAAGGACGAAACACC

GATTTAGAATCCCCTAAGGA GTTTAAGAGCTATGCTGGAAAC

Positive in MERA

TdgfFU49_60bp
(SEQ ID NO: 169)
GGAAAGGACGAAACACC

GTCCGAGACTGCGGCTCTTAC GTTTAAGAGCTATGCTGGAAAC

Positive in MERA

TdgfFU50_60bp
(SEQ ID NO: 170)
GGAAAGGACGAAACACC

GTCGGATGACCTGAGTAGAGC GTTTAAGAGCTATGCTGGAAAC

Negative in MERA
PCR primers:

TdgfFU46_up_fw
(SEQ ID NO: 171)
cctctggcctccgagtcatctga

TdgfFU50_dwn_rv
(SEQ ID NO: 172)
TCATCCACACACAGAAGTTCTACGT

Results and Conclusions

To enable the efficient targeting of precisely one regulatory element per cell, we devised a strategy that ensures that only one gRNA can be expressed per cell and that allows gRNA libraries to be used without any molecular cloning into a delivery vector. We integrated a single copy of integrated a single copy of the gRNA expression construct (a U6 promoter driving expression of a dummy gRNA hairpin) into the universally accessible ROSA locus of mESCs using CRISPR/Cas9-mediated homologous recombination (FIG. 1A). We then use CRISPR/Cas9-mediated homologous recombination to replace the dummy gRNA with a gRNA from our library. We use PCR to add 79-90 bp homology arms to our gRNA library, as we found that longer homology arms increase background cutting of unintegrated gRNA PCR fragments (data not shown). We then introduce the pool of gRNA homology fragments into cells along with Cas9 and a gRNA plasmid that induces a DSB at the dummy gRNA site. In a substantial fraction of cells (~30%), the dummy gRNA is repaired by homologous recombination, creating a functional gRNA expression construct targeting a single genomic site from the library (data not shown). It is random chance which gRNA is integrated in each cell, allowing a pooled screen in which each cell expresses only one gRNA. Of note, the genomic integration-based gRNA screening platform used in MERA could also be applied to other CRISPR-based high-throughput screens as long as the cell line undergoes homologous recombination at appreciable frequency, and it could be modified to achieve expression of any set number of gRNAs per cell for combinatorial screening. While the integration-based approach is thus ill-suited to in vivo screens or screens in cells with limited homologous recombination, it provides an alternative to lentiviral screening that substantially reduces the time, effort, and cost involved in CRISPR library screening for applicable cell lines such as ESCs.

We have recently reported a method enabling efficient CRISPR-mediated knock-in transgene insertion that uses PCR-amplified homology arms, removing the time-consuming step of cloning homology arm vectors (Arbab et al. Stem Cell Reports, 2015). We used this procedure to construct GFP knock-in alleles at four genes with mESC-specific expression, Nanog, Rpp25, Tdgf1, and Zfp42. We chose to focus on mESC-specific genes because the networks of mESC gene regulation and epigenetic state of mESC regulatory elements are among the best understood of any cell type[29, 30]. Two of the genes (Nanog and Rpp25) were constructed as C-terminal GFP fusion proteins, and two (Tdgf1 and Zfp42) had their open reading frames replaced with GFP to compare these two approaches. All knock-in lines, upon clonal selection, had robust GFP expression, although GFP levels were highest in Tdgf1$^{GFP}$ and Zfp42$^{GFP}$ lines (FIG. 1B, data not shown). The Nanog$^{GFP}$ line always contained ~20% GFP⁺ cells, presumably due to known heterogeneous Nanog expression in mESCs (data not shown)[31].

We synthesized four gRNA libraries, each with 3908 gRNAs tiling cis-regulatory regions of Nanog, Rpp25, Tdgf1, and Zfp42. In case of Tdgf1, the library targeted the 40 kb region proximal to the gene in an unbiased manner. In other cases, we selected proximal regions to the gene most likely to be involved in regulation based on enhancer-like features that are a maximum of ~150 kb away from the gene. Additionally, distal regions up to 92 mB away from the gene were added when ChIA-PET distal interaction data[9] suggested a possible interaction with the target gene promoter using the Sprout algorithm[35]. In FIGS. 2A-D and 3A-C, the bulk density panel shows the distribution of integrated guide RNAs along the region probed. Among the 3621 gRNAs found to be integrated in at least 1 replicate of Tdgf1, 99% were within 140 bp of the nearest adjacent gRNA and 95% were within 32 bp of the adjacent gRNA. Distances were measured between the mid-points of adjacent gRNAs. The mean distance between adjacent gRNAs was 11 bp, and the standard deviation of this distance was 32 bp. Of note, repetitive and unmappable genomic regions cannot be tiled with gRNAs, and gRNAs targeting regions whose sequence differs from that of the reference genome cannot be appropriately tiled without genome sequence data of the cell line. Each library also contained 10 positive control gRNAs targeting the GFP open reading frame that we expected would cause GFP loss.

Figure 1C:
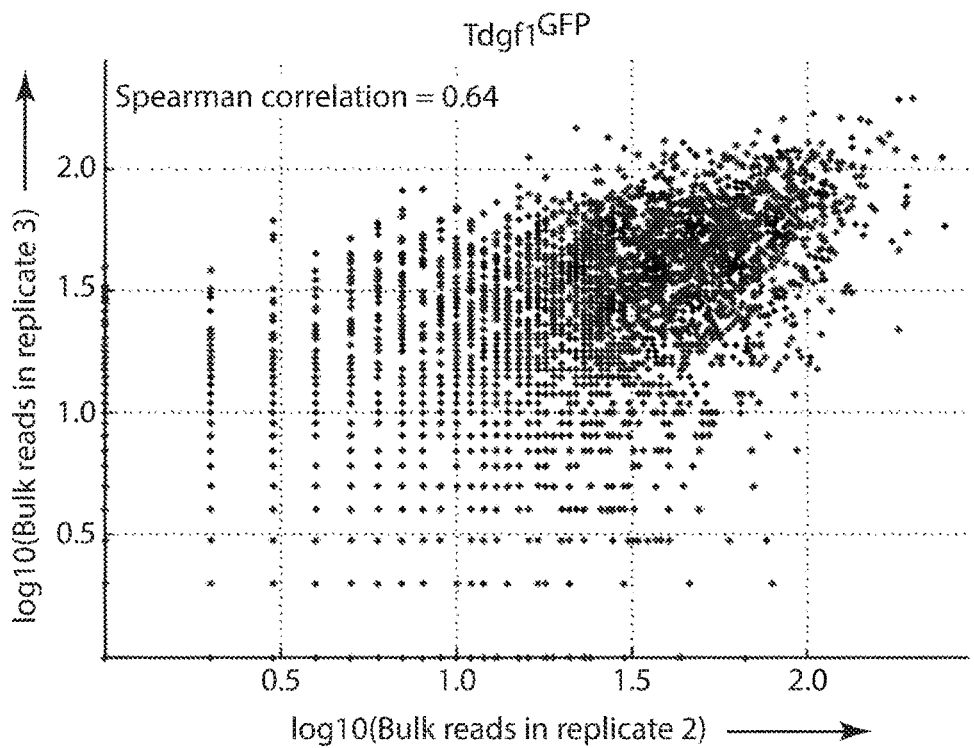
Figure 1D:
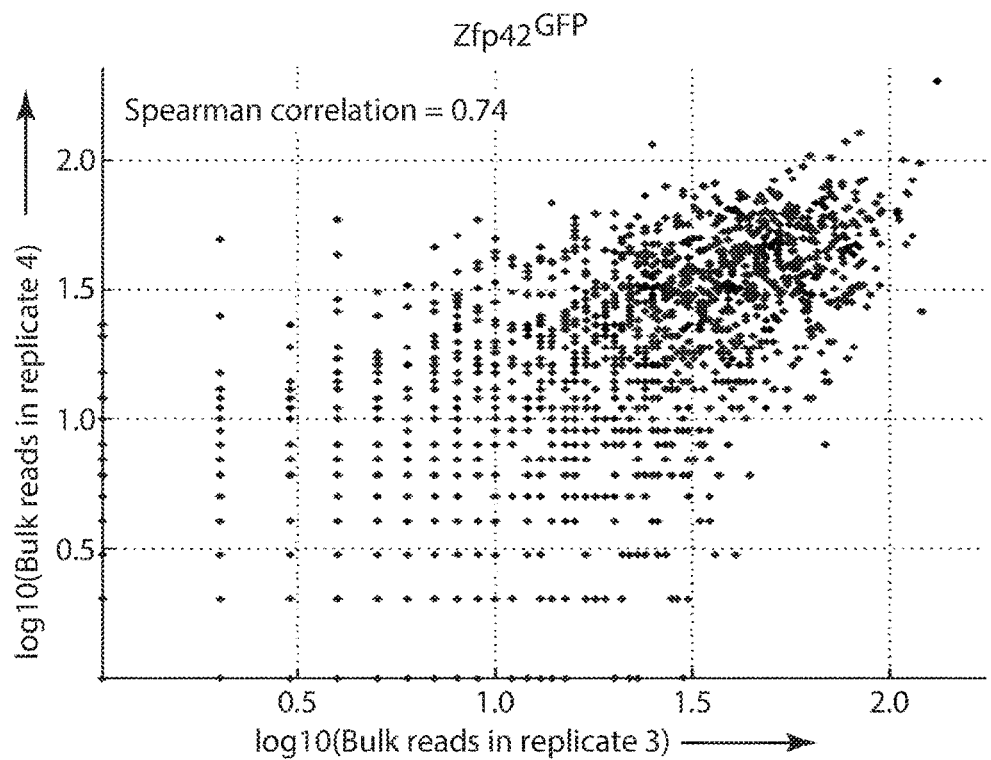

We performed four biological replicate screens for Zfp42 and Tdgf1, two replicates for Nanog and a single replicate for Rpp25. Selected screen hits were independently confirmed as described below. Starting one week after electroporation, we collected genomic DNA of the unsorted library-integrated cells to examine differences in gRNA integration. Over 90% of correctly synthesized gRNAs were detected in the genomic DNA for both Tdgf1 and Zfp42 libraries. In addition, gRNA integration rates in biological replicates showed concordance (FIGS. 1C-1D, and data not shown). All of the regulatory regions that we surveyed had adequate coverage of gRNAs to assay their detailed function (Bulk density track, FIGS. 2A-D, 3A-C, data not shown).

Library-integrated mESCs were then flow cytometrically sorted to identify gRNAs inducing loss of GFP expression. Separate GFP$^{neg}$ and GFP$^{medium}$ populations were sorted in the Tdgf1$^{GFP}$ and Zfp42$^{GFP}$ experiments, while GFP$^{neg}$ and GFP$^{medium}$ populations were combined in the Nanog$^{GFP}$ and Rpp25$^{GFP}$ experiments because of incomplete population separation (FIG. 1B, data not shown). All sorted populations were >90% pure except the Tdgf1$^{GFP}$ GFP$^{medium}$ population, which showed a subpopulation of GFP$^{neg}$ cells even after multiple sorts, indicating intrinsic fluctuation in GFP expression in this population (data not shown). Integrated gRNAs in the genomic DNA from bulk unsorted as well as sorted populations were deep sequenced to reveal the relative importance of each gRNA-targeted cis-regulatory sequence in governing gene expression (FIGS. 4A-4D, 5A-5D).

The distribution of gRNA abundance in GFP$^{neg}$ and GFP$^{medium}$ populations in all screens clearly indicates that a subset of cis-regulatory genomic space is required for gene expression at all four gene loci (FIGS. 2A-2B, FIGS. 3A-C). Importantly, we detected significant overrepresentation of nearly all integrated positive control GFP coding region targeting gRNAs in all replicates (FIG. 2D, FIG. 3C, data not shown) suggesting that MERA robustly identifies gRNAs inducing loss of gene expression. Using the relative abundances of GFP ORF-targeting positive control gRNAs and the dummy gRNA as a negative control, we devised a method to detect gRNAs with statistically significant over-representation in GFP$^{neg}$ and GFP$^{medium}$ populations (data not shown).

Figure 2A:
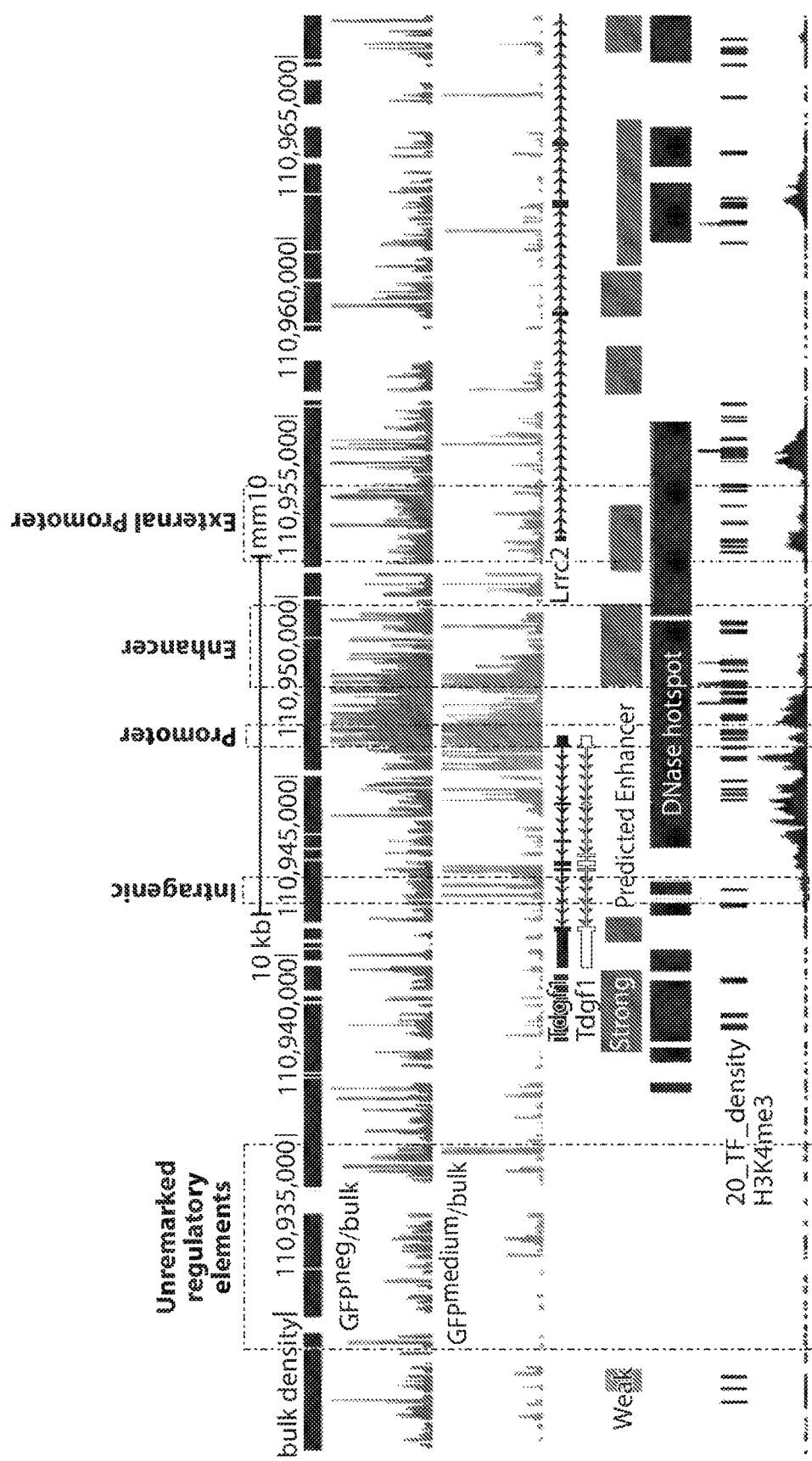
FIGS. 2A-2D. MERA enables systematic identification of required cis-regulatory elements for Tdgf1.
Figure 2B:
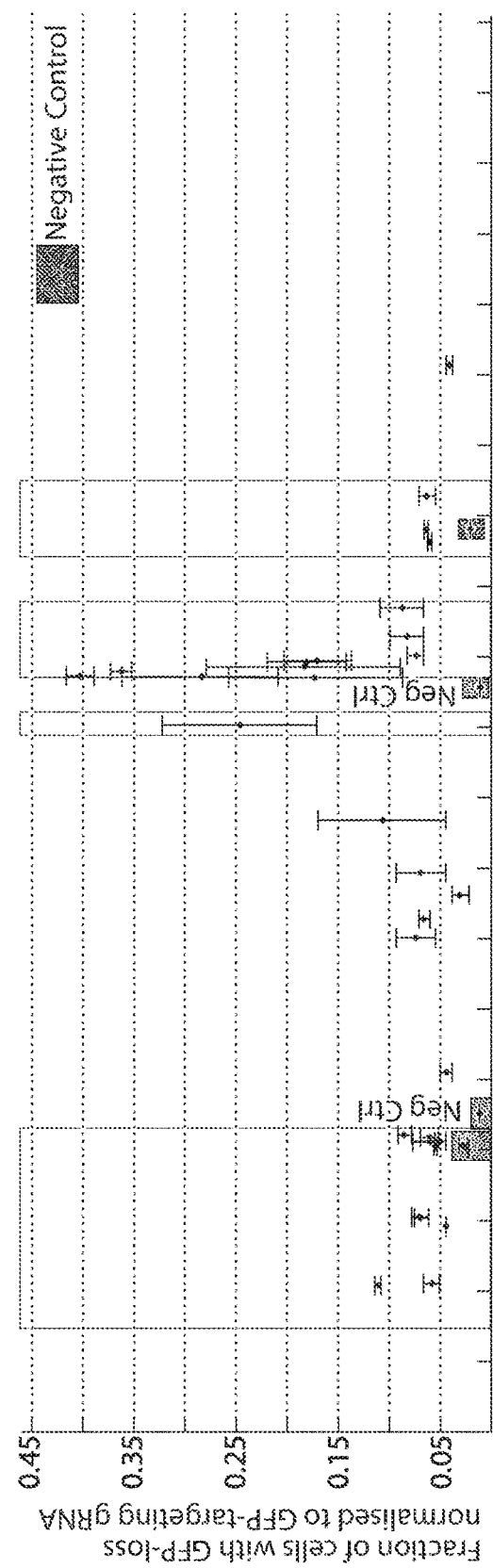
Figure 2C:
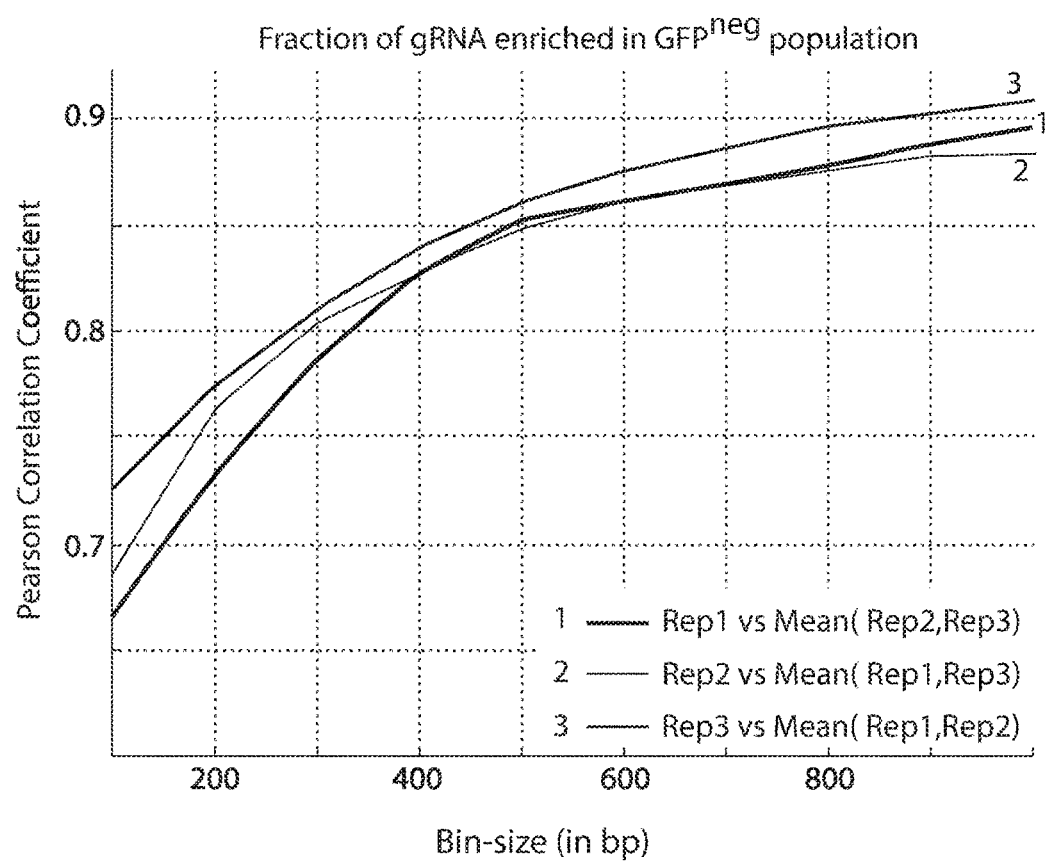
Figure 2D:
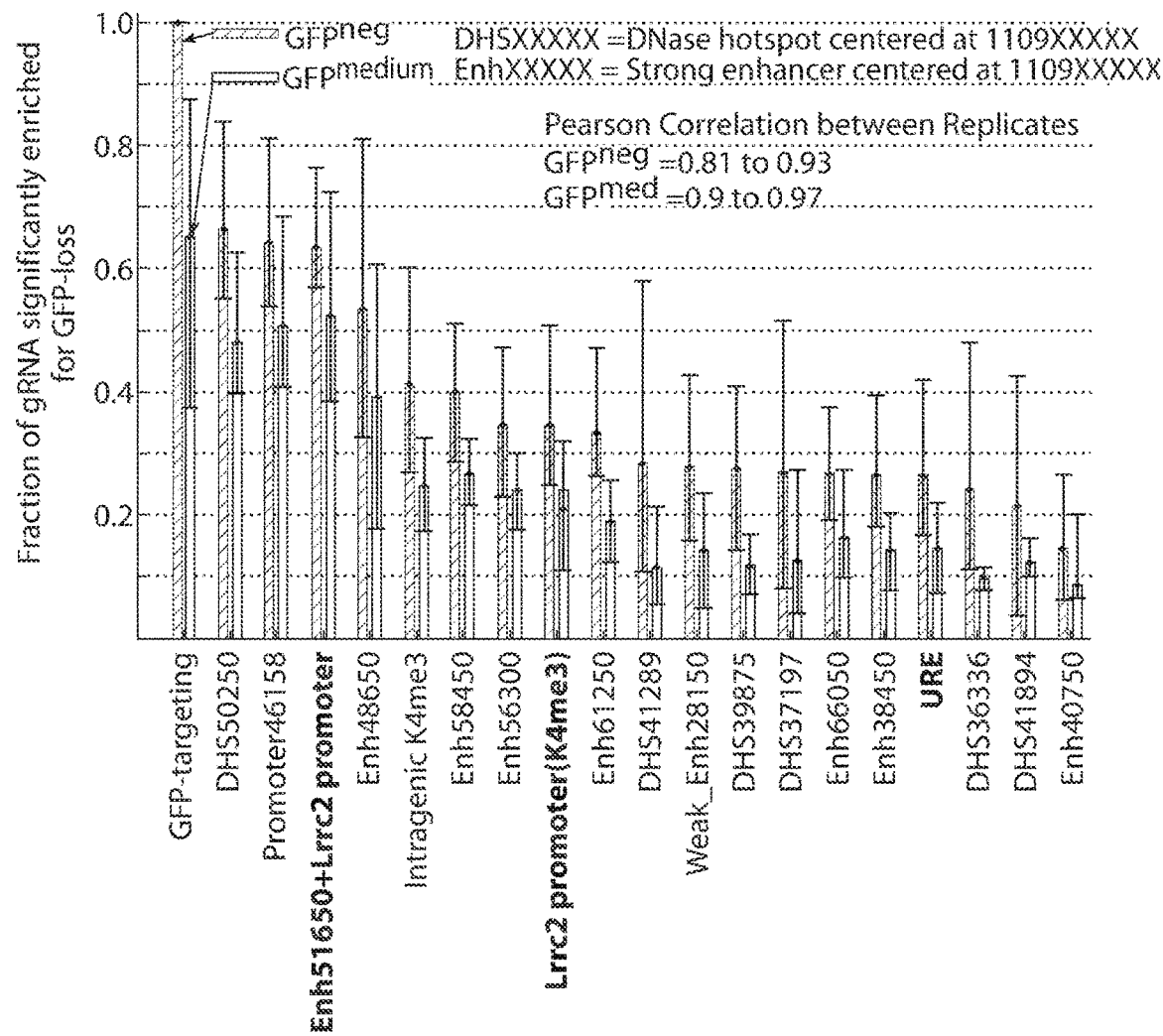

In our MERA screen of Tdgf1 we observed differential enrichment of gRNAs in established functional categories of genomic elements associated with gene regulation (FIGS. 2A, 2D, data not shown). Among these categories were enhancers predicted using chromatin modifications[32, 33] and classified as strong or weak based on the enrichment of H3K27ac, DNase-I hotspots[34] predicted from DNase-seq data[35] and transcription factor binding sites predicted from ChIP-seq data[36] for 20 transcription factors known to be important in ES cell biology. The highest density of significant gRNAs in the genomic regions were observed at the promoter region for Tdgf1, the neighboring DNase-I hotspot 4 kb upstream adjacent to the Lrrc2 promoter, and the strong enhancer overlapping the Lrrc2 promoter (FIGS. 2A, 2D). We observed other expected trends such as greater enrichment of significant gRNA at predicted strong enhancers proximal to the gene as compared to weak enhancers or enhancers further away.

Surprisingly we observed a novel class of genomic elements downstream of Tdgf1 (FIG. 2A, highlighted in grey) which did not coincide with any known markers of regulatory activity such as H3K27ac, H3K4me1, H3K4me3, known TF binding sites, DNase-I hypersensitivity, predicted DNase-I hotspots, or enhancers predicted from chromatin modifications. We designated such elements that do not contain these markers as Unmarked Regulatory Elements (UREs). Unmarked regulatory regions produced comparable loss of GFP as some distant enhancers (FIG. 2D).

Figure 3A:
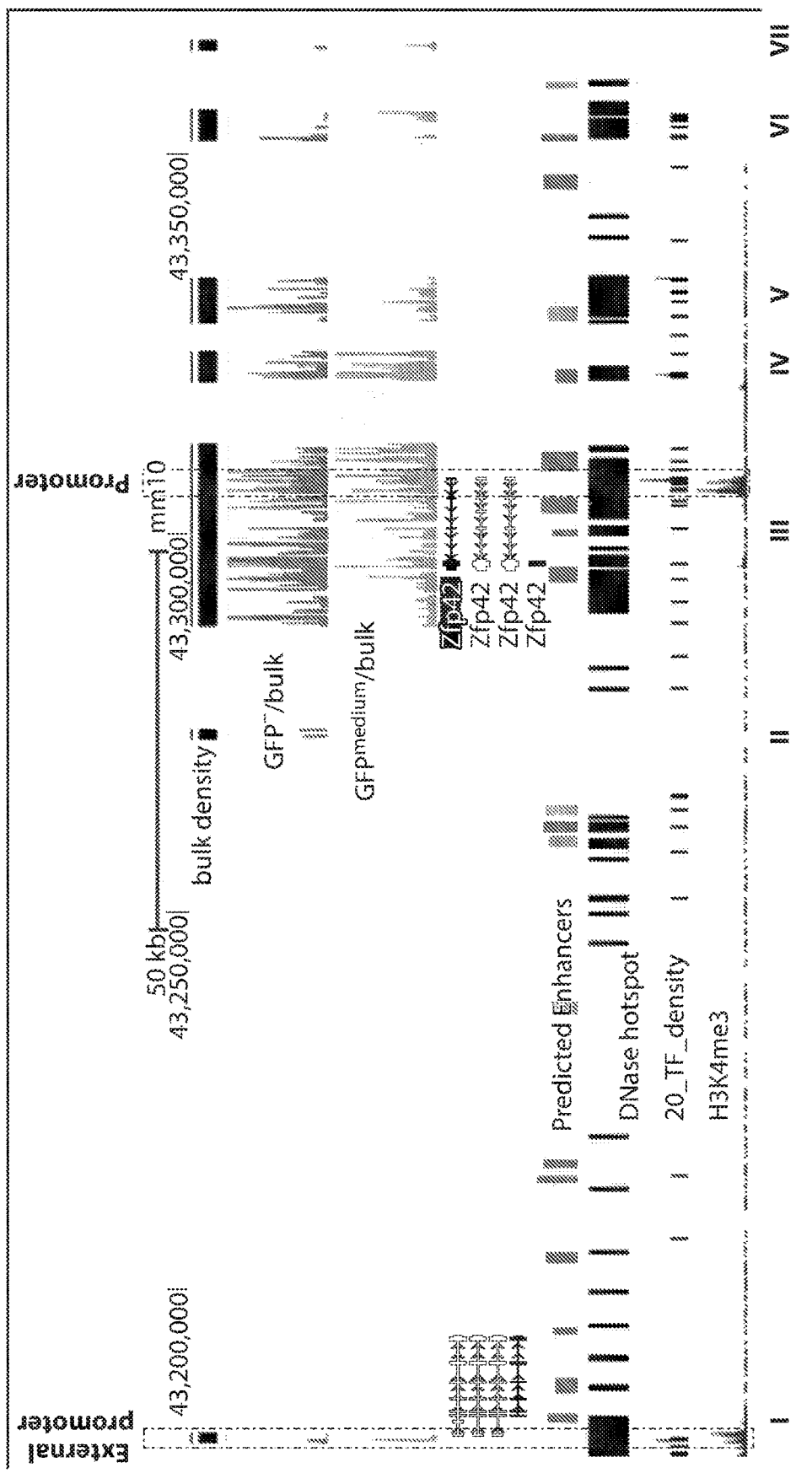
FIGS. 3A-3C. MERA enables systematic identification of required cis-regulatory elements for Zfp42.
Figure 3B:
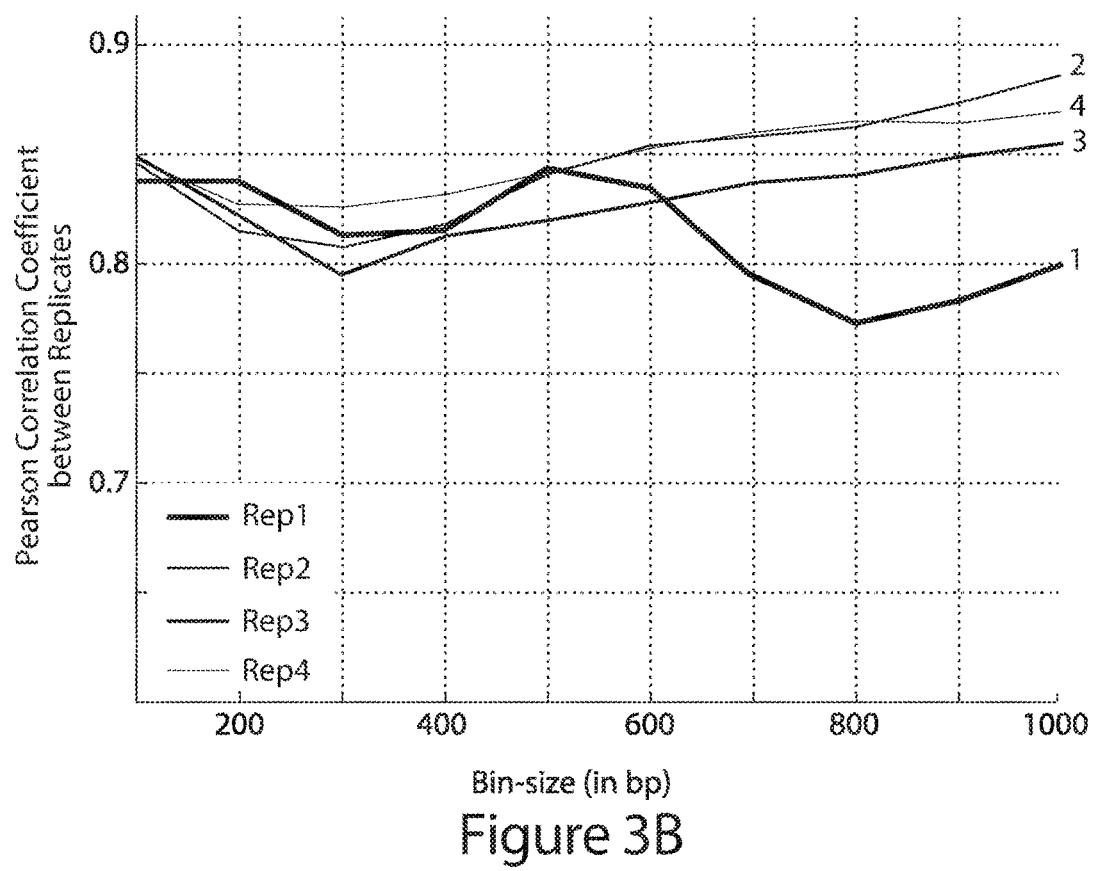
Figure 3C:
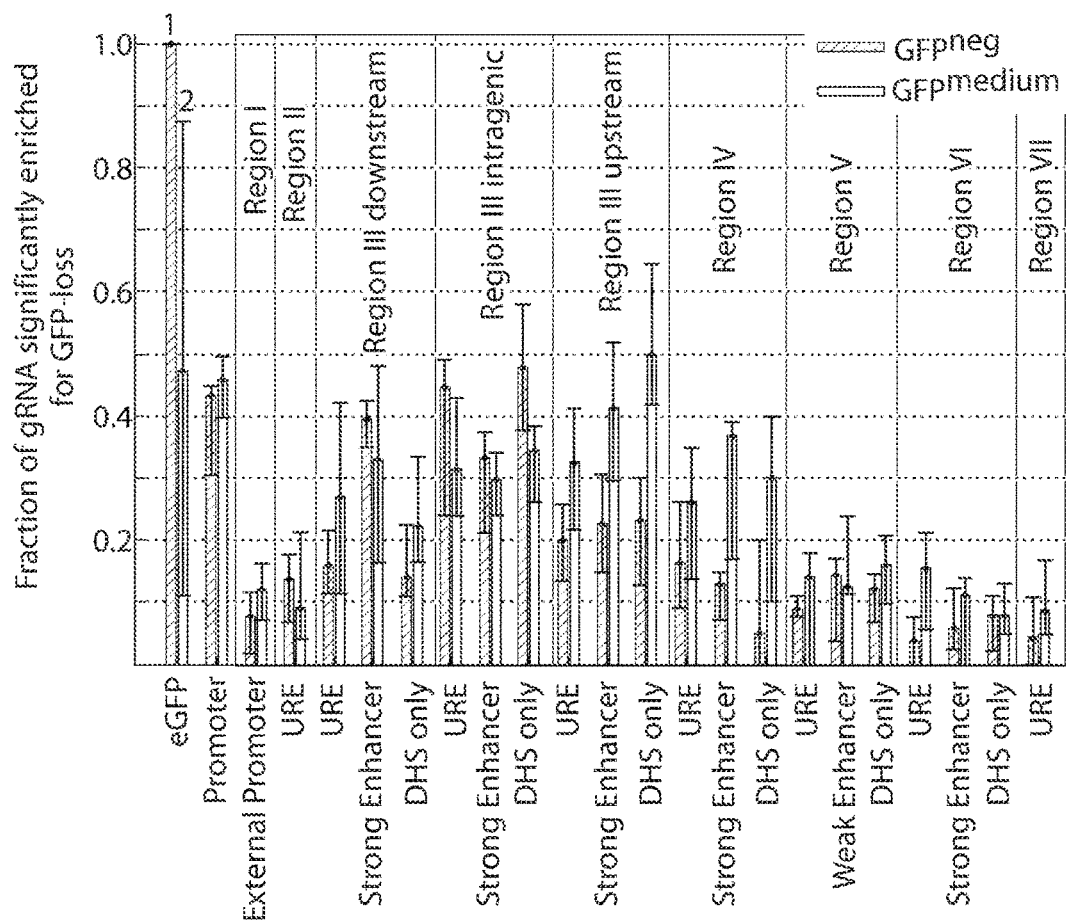

In our MERA screen of Zfp42, we also observed the strongest enrichment for GFP loss in the promoter and proximal enhancer regions (FIGS. 3A, 3C). We observed enrichment of gRNAs in GFP$^{neg}$ and GFP$^{medium}$ population at UREs in region II and VII, and also in intervening unmarked regions in regions III to VI (FIG. 3A, data not shown). We also observed the participation of a neighboring promoter Trim12 in the regulation of the Zfp42 gene (FIG. 3A, data not shown). Upon examining the fractional enrichment of gRNAs causing GFP loss in various functional categories, we observe that trends for higher enrichment of gRNAs causing GFP loss are strongly associated with proximity to the gene rather than functional annotation of the region (FIGS. 3A, 3C). gRNAs in UREs flanking enhancers as in regions III to VI are more likely to induce GFP loss than those in distal UREs. Some of these UREs are over 1 kb along as in the case of region IV (chr8:43322062-43323500), hence it is unlikely that GFP loss is an artifact of long disruptions caused by individual gRNAs in the URE region. We also note that regulatory regions upstream of Zfp42 tended to cause intermediate loss of GFP as compared to a complete loss of GFP (GFP$^{medium}$ vs. GFP$^{neg}$, FIG. 3C), suggesting that these enhancers are each responsible for only part of the overall Zfp42 expression level in cells.

To determine the accuracy of the MERA screen in systematically determining required cis-regulatory regions, we first examined replicate consistency among our Tdgf1, Zfp42, and Nanog MERA data. Spatial patterns of gRNA enrichment in the GFP$^{neg}$ population were largely conserved between replicates (FIG. 2B, FIG. 3B, data not shown). The Pearson correlation between the fraction of GFP$^{neg}$ gRNA enriched within bins improves with bin length achieving a correlation coefficient of 0.9 at a bin size of 1 kb in Tdgf1. In Zfp42, we observe a correlation of 0.85 even at bin sizes of 100 bp. Thus, MERA has utility in detecting the relative importance of regulatory regions for a particular gene. At an individual level, the overlap between gRNAs enriched in GFP$^{neg}$ populations between replicates was significant for all replicates in the 3 lines, Tdgf1$^{GFP}$, Zfp42$^{GFP}$ and Nanog$^{GFP}$ (hyper geometric p-value <0.001); however, some gRNAs found to be significant in one replicate were not observed to be so in another. We found that several of the gRNAs that were significant in only one replicate induced significant GFP loss in an individual test (FIG. 2B), suggesting that the high complexity of MERA data in which a single gRNA can cause hundreds of distinct mutant genotypes leads to some experimental variability.

To analyze potential false positives caused by off-target effects, we built a model of CRISPR off-target cutting using data from 13 gRNAs that were generated by GUIDE-Seq[37]. We found that in inverse proportion to the GC-content, guide RNAs could tolerate between a maximum of 3 to 6 total mismatches including the PAM region, with up to 3 mismatches in the seed region (9-20 bp) (data not shown). We defined a true negative set as pairs of gRNAs causing significant GFP-loss in at least 2 replicates and gRNAs that were integrated in all replicates but did not cause any significant loss of GFP. Any gRNA found to be non-significant could not possibly have an off-target effect at a site where a significant gRNA was cutting. Using our model of off-target effects no pairs in the above-defined negative set had any predicted interactions (data not shown).

We then used our model of potential off-target effects to determine the promiscuity of gRNAs in the Tdgf1 and Zfp42 libraries. In the Tdgf1 library, 1160/3621 of the integrated gRNAs have potential off-target effects, and 150/925 of the gRNAs that were significantly enriched in GFP$^{neg}$ populations have one or two potential off-target sites within the topological domain containing the Tdgf1 gene as determined from mESC HiC data[38]. In the Zfp42 library, 632/1643 integrated guide RNAs have predicted off-target effects, and 34/332 of the gRNAs enriched in GFP$^{neg}$ cells have predicted off-target effects in the topological domain containing the Zfp42 gene[38]. We found that when we eliminate gRNAs with potential off-target effects from our analysis, the global distribution of significantly enriched gRNAs along the regulatory landscape of the gene is unaltered and relative contributions of different functional categories are unaffected (data not shown). Furthermore, several gRNAs with no predicted off-target effects support the regulation of Tdgf1 by the promoter of Lrrc2 (data not shown), the promoter of Trim12, and a URE region (data not shown), and none of these regions are more likely to contain off-target effects than other screened regions. Our off-target predictions are overly cautious, as off-target cutting is typically much more rare than on-target cutting[37] and the off-target sites predicted for MERA hits are often >200 kb away from the gene reducing the likelihood of there existing a functional association. However, even this overestimate of off-target effects does not alter the patterns seen in MERA data.

To analyze potential off-target effects with an independent method, we asked whether any gRNAs from the Tdgf1 library would extinguish Zfp42-GFP activity and vice versa. We found that a much smaller percentage of cells lose GFP upon targeting by a mismatched gRNA library than by the matched library (data not shown). Sequencing revealed that the gRNAs enriched in GFP[neg] mismatched library-targeted cells were predominantly GFP control gRNAs with a small number of non-clustered gRNAs displaying off-target activity (data not shown). Thus, the clustered enrichment of GFP loss at enhancers, neighboring promoters, and UREs in MERA is not replicated by computationally predicted or experimentally determined off-target effects, leading us to conclude that GFP loss in these regions is a result of on-target gRNA effects (data not shown).

To determine the false positive rate at the level of individual gRNAs, we introduced individual gRNAs to determine whether their rate of GFP loss correlated with their activity in the pooled MERA screen. These gRNAs fell within several of the functional categories including UREs and neighboring promoters (FIG. 2A highlighted in grey, FIG. 2B). We confirmed significantly increased GFP loss in 29/30 gRNAs from these screens as compared to five similarly located control gRNAs (FIG. 2B). Nine of these gRNA were in the URE regions downstream of the Tdgf1. Altogether, we conclude that MERA has a low false positive rate.

We next sought to determine the false negative rate of MERA. We found 10/10 GFP-targeting gRNAs in all 4 GFP-lines are highly enriched in GFP[neg] cells (FIG. 2D, FIG. 3C). Additionally, 67/83 (81%) gRNAs that target the first 700 bp of the Rpp25 open-reading frame are highly enriched in GFP[neg] cells. In a 500 bp around the Tdgf1 promoter region, 48/59 (81%) of gRNAs induce GFP loss in multiple replicates (data not shown). Thus, we find that a high percentage of gRNAs expected to have an effect on gene expression are enriched in GFP[neg] cells. It is unclear whether the 20% of gRNAs in these regions that do not induce GFP loss are false negatives or true negatives, as their mechanism of inducing GFP loss is not as direct as when the GFP ORF itself is targeted. However, even if this appreciable percentage of individual gRNAs are false negatives, it does not impair the ability of MERA to determine required regulatory regions, as the high density of gRNAs in a region (~1 per 8 bp) allows highly reproducible resolution at the level of 100-1000 bp (FIGS. 2C, 3B).

To follow up on a specific region in which only some gRNAs induce GFP loss, we tested two pairs of adjacent gRNAs in which one gRNA induces GFP loss whereas the other does not. In one pair we discovered that the gRNA that did not induce loss of GFP was able to cut DNA efficiently and thus was a true negative gRNA (data not shown). In the other pair, we found that the gRNA that did not induce GFP loss was impaired at cutting DNA because a SNP in the target genome changed an expected PAM sequence from NGG to NAG (data not shown). While this analysis is low-throughput, it illustrates that false negatives at the level of individual gRNAs can be caused by differences between the reference genotype and the genotype of the cell line used in our study.

Since each gRNA induces a spectrum of mutations at its target site, this genotypic diversity induced by the same gRNA can result in a range of GFP expression after introduction of each gRNA. For instance, individual targeting of some gRNAs in promoter regions induced GFP loss in over 40% of cells, whereas gRNAs targeting other promoter-distal elements induced GFP loss in only 5-10% of cells (FIG. 2B). Targeting the GFP ORF induces GFP loss in >90% of cells, and negative controls induce loss in <2% of cells in these assays. This is in stark contrast to CRISPR/Cas9-based gene inactivation screens in which all gRNAs are assumed to be equivalently likely to induce frameshift mutations that inactivate gene function. We utilize the genotypic heterogeneity for functional motif discovery as described herein. Regarding false negatives, however, we conclude that MERA has a low but appreciable false negative rate attributable primarily to the large range of mutations that each gRNA can induce and the variable likelihood that mutations at each site will induce GFP loss.

Our MERA results revealed that Tdgf1, Nanog, Rpp25 and Zfp42 have different regulatory architectures (FIGS. 2A-D, FIGS. 3A-C, data not shown). All regulatory regions within +/−20 kb of the Nanog promoter were associated with clusters of highly enriched gRNAs, and 20% to 40% of the tested gRNAs in predicted enhancers and DNase-I hotspots proximal to Nanog resulted in GFP[r] cells (data not shown). In contrast, the Rpp25 gene shows a dense concentration of significant gRNAs at its promoter and short ORF region. Other proximal regulatory regions of Rpp25 had 12% of tested gRNAs resulting in GFP[neg] cells (data not shown). Tdgf1 shows a similar trend to Nanog with dense clusters of significant gRNA in the proximal regulatory regions (FIGS. 2A, 2D). UREs were also seen in cis-regulatory regions near Rpp25 (data not shown). In Nanog, a distal ChIA-Pet region >92 mB away showed several strongly enriched gRNAs (data not shown), indicating that MERA is capable of measuring the functionality of long-distance chromatin interactions. One observation common to all genes is the participation of the promoters of other genes in regulation. In some cases these gene promoters are several million bases away. Examples of foreign promoter involvement can be seen in the case of Lrrc2 promoter in Tdgf1 (FIGS. 2A, 2D), Mirc35hg in Nanog (data not shown), Scamp5 and Cox5a in Rpp25 (data not shown). Previous studies have documented the existence of dual property elements[39] that can act as either promoter or enhancer in different cellular contexts. Additionally, it is known that neighboring promoters often interact with each other[40] and that neighboring gene expression is often coordinated[41]. Here we observe that active promoters may coordinate gene expression patterns of neighboring genes by functioning as enhancers within the same cellular context.

The second phase of MERA uses functional motif discovery to identify the causal elements governing expression at MERA screen hits. Because Cas9 induces random mutations, a pool of mESCs treated with Cas9 and a single gRNA will contain thousands of distinct mutant genotypes centered on the gRNA cleavage site. Recently, TAL effector nucleases have been used to derive functional footprints of regulatory DNA[42]. We hypothesized that we could pinpoint DNA sequence motif(s) that cause GFP loss by identifying sequence features that consistently differ between thousands of GFP[pos] and GFP[neg] genotypes at a given site (FIG. 4A). Functional motif discovery proceeds by performing individual scCRISPR-mediated mutation by a selected gRNA and obtaining thousands of genotypes from both GFP[pos] and GFP[medium/neg] cells by high-throughput sequencing and then summarizing the observed genotypes as motifs that reveal what bases are important for gene expression (FIG. 4A). Using the differences in fractions of genotypes at positions along the gRNA, we defined a base-level importance score that was independent of the cutting biases of the gRNA. We computed the Hellinger score of the distance of the mutational profile at each base (4 base possibilities plus a deletion) to the reference base for both GFP$^{pos}$ and GFP$^{neg}$ populations. The log-ratio of distance of GFP$^{neg}$ to the reference to the distance of GFP$^{pos}$ to the reference provided a base-level estimate of the importance of the base in causing GFP loss.

Figure 4D:
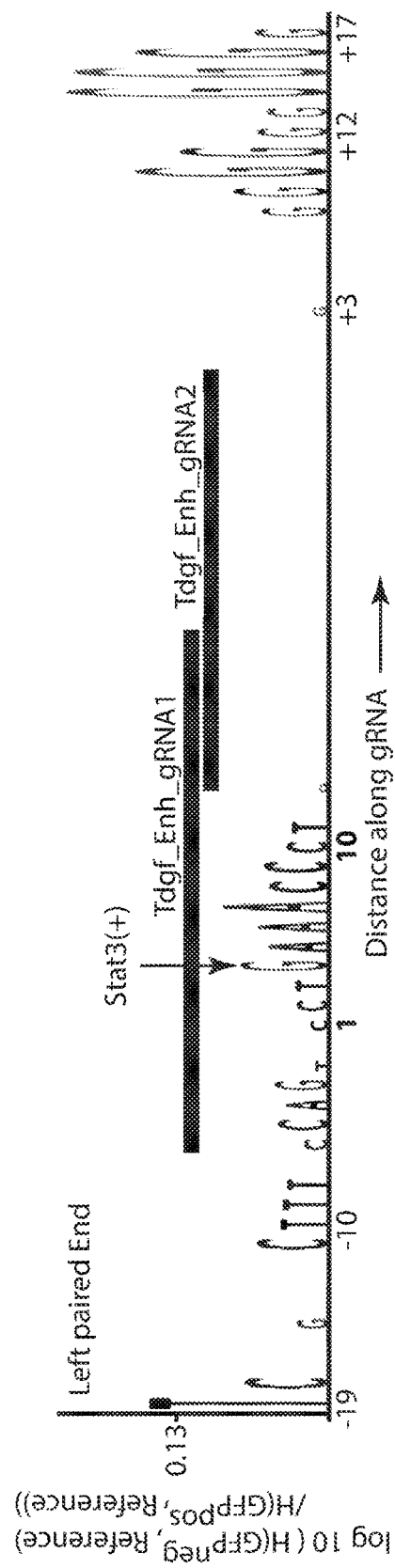

We first tested to see if functional motif discovery in Tdgf1 and Zfp42 enhancer regions would permit us to classify held out genotypes as GFP$^{neg}$ or GFP$^{pos}$ and identify motifs for transcription factors that are directly bound to these regions in mESC cells. We selected two overlapping gRNAs for functional motif discovery in a Tdgf1 proximal enhancer that overlapped binding sites for the key mESC transcription factors Stat3, Sox2 and Tcfcp2lI, of which Stat3 is the only factor with a direct binding site. We were able to classify held out genotypes with an AUC of 0.81 (FIG. 4C), and observed an enrichment of the bases for the Stat3 motif[29] in both the left and right paired end reads (FIG. 4D, data not shown). In a Zfp42 enhancer, we selected two gRNAs separated by ~100 bp with the first gRNA target containing a site for Nrf1 binding (TGCGCAG) and the second gRNA containing a direct binding site for Smad3/Med1/K14 and an indirect binding site for p300 (data not shown). Functional motif discovery for these Zfp42 gRNAs classified held out genotypes with AUCs of 0.77 and 0.71 (data not shown) and revealed bases near the Nrf1 site, around the p300 site, and a slight enrichment of the G-rich tract proximal to the Klf4 binding motif (data not shown).

Figure 5A:
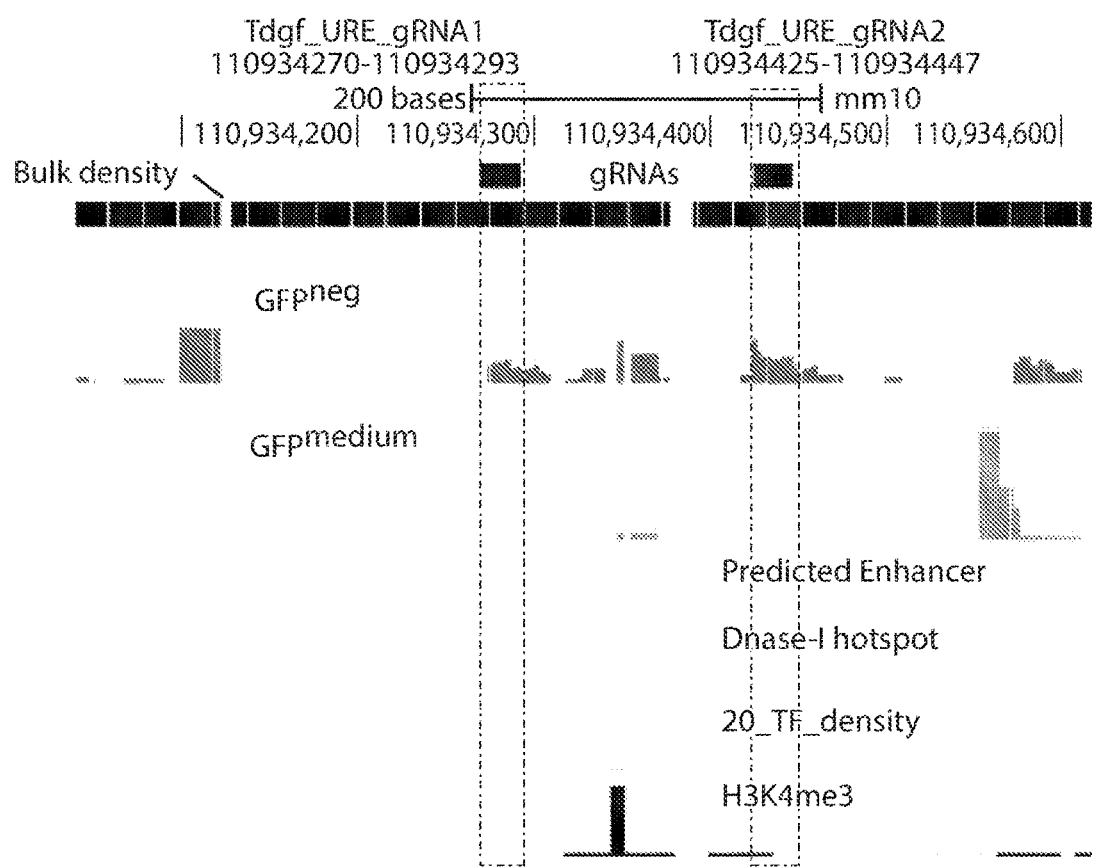
FIGS. 5A-5D. Functional motif discovery analysis of a URE reveals critical base positions involved in gene regulation.
Figure 5B:
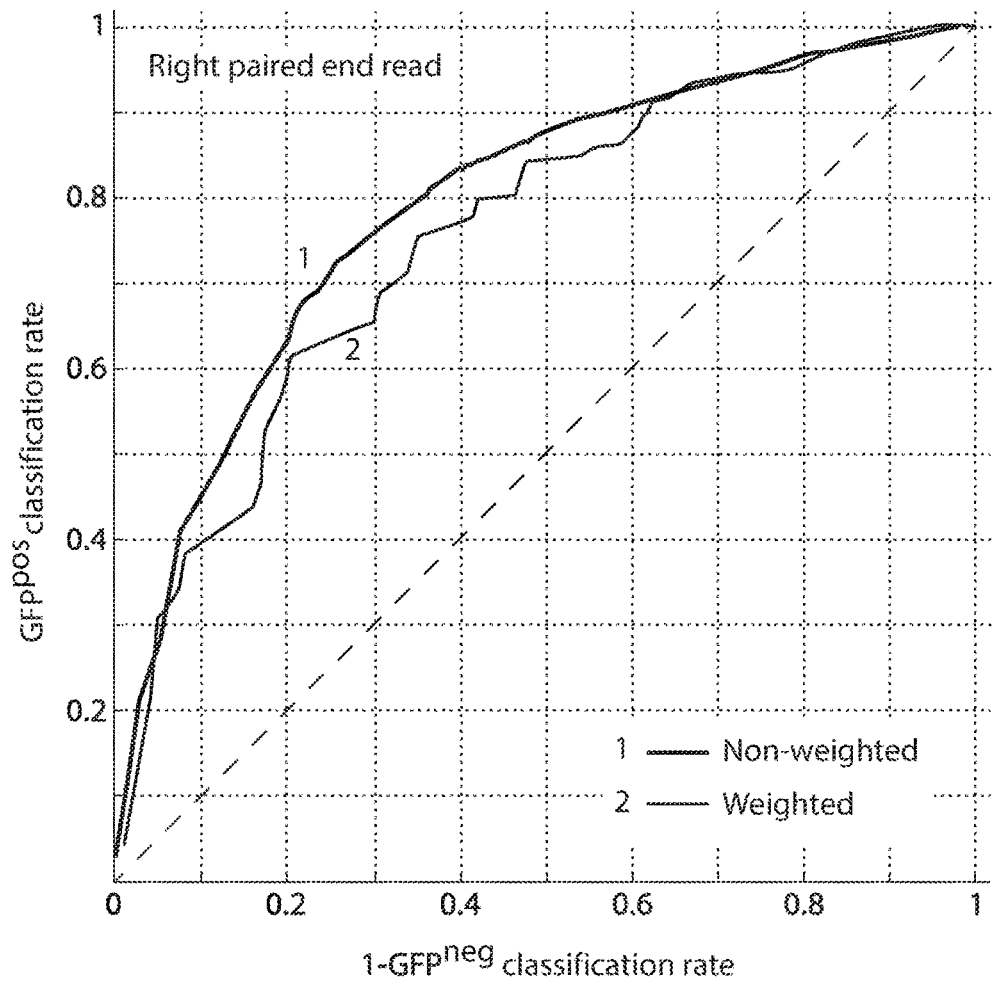
Figure 5C:
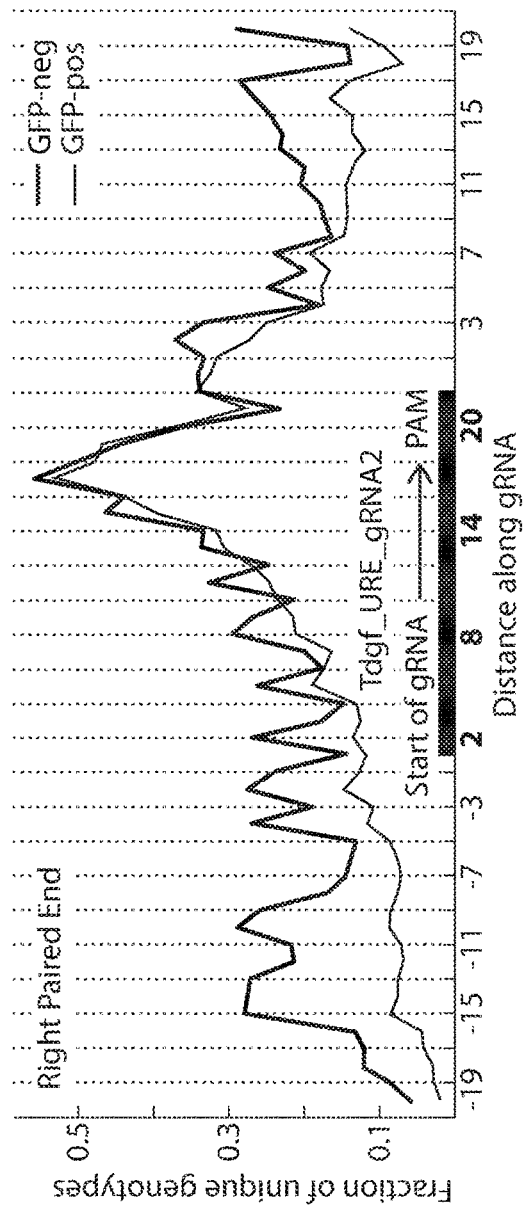
Figure 5D:
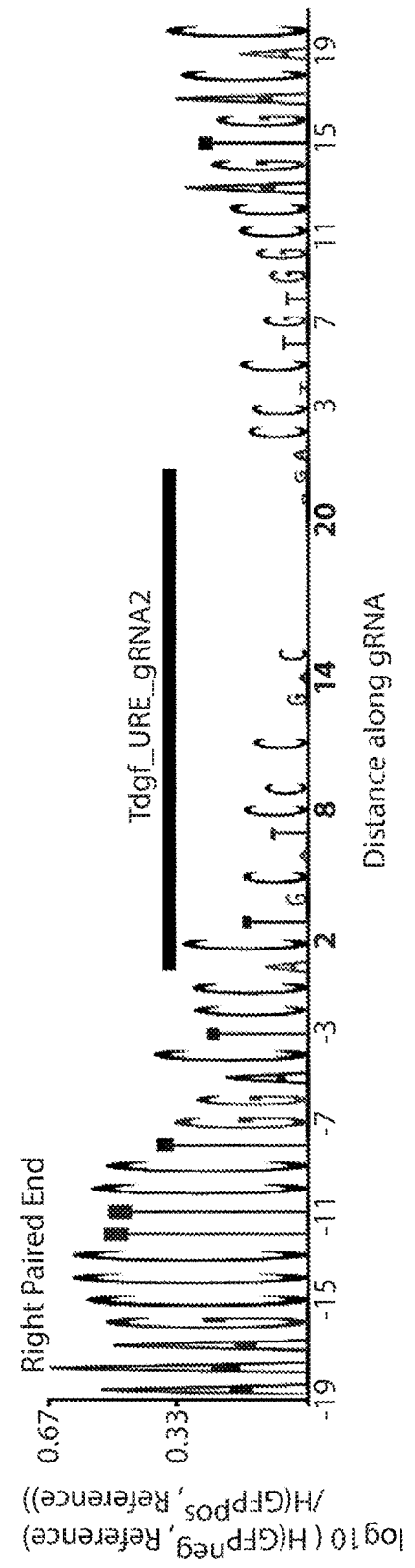

We next applied functional motif discovery to 2 gRNAs that are in a URE ~12 kb downstream of the Tdgf1 transcript (FIG. 5A). We observed higher enrichment of mutated bases in GFP$^{neg}$ genotypes over GFP$^{pos}$ genotypes for both gRNAs (FIG. 5C, data not shown), and we found distinctive patterns of base importance scores emerging for both gRNAs (FIG. 5D, data not shown). We found that we could obtain high classification accuracy for held out genotypes from both gRNAs (AUC 0.81 and 0.76) for separating GFP$^{pos}$ and GFP$^{neg}$ populations using mutations within –20 to +20 bp as features (FIG. 5B, data not shown). It was also noted that for both these gRNAs, the majority of mutations were contained within 20 bp of the gRNA (data not shown). Insertions were enriched in the GFP$^{neg}$ population vs. GFP$^{pos}$ but they were less common than deletions (data not shown). Altogether, we conclude that functional motif discovery is a valuable method for ascertaining which bases at MERA-identified regulatory regions are required for gene expression. In enhancer regions, these bases correspond to known binding motifs, and in UREs, we identify blocks of bases which are required for gene expression.

Figure 6A:
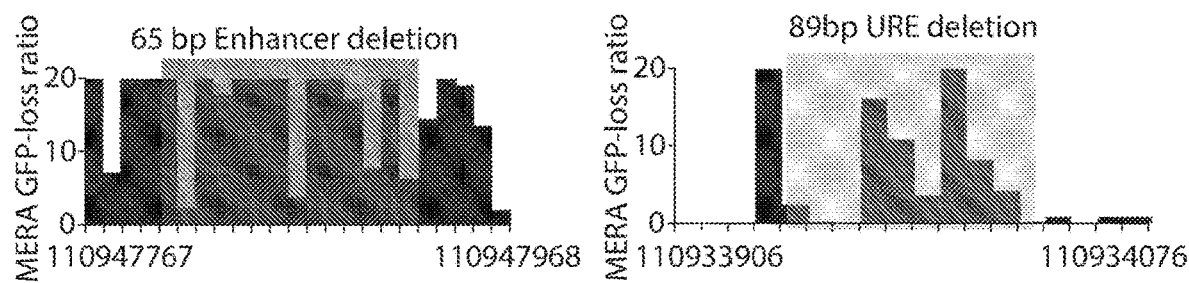
FIGS. 6A-6C. Local genotypes at an enhancer and a URE dictate Tdgf1 expression phenotype.
Figure 6B:
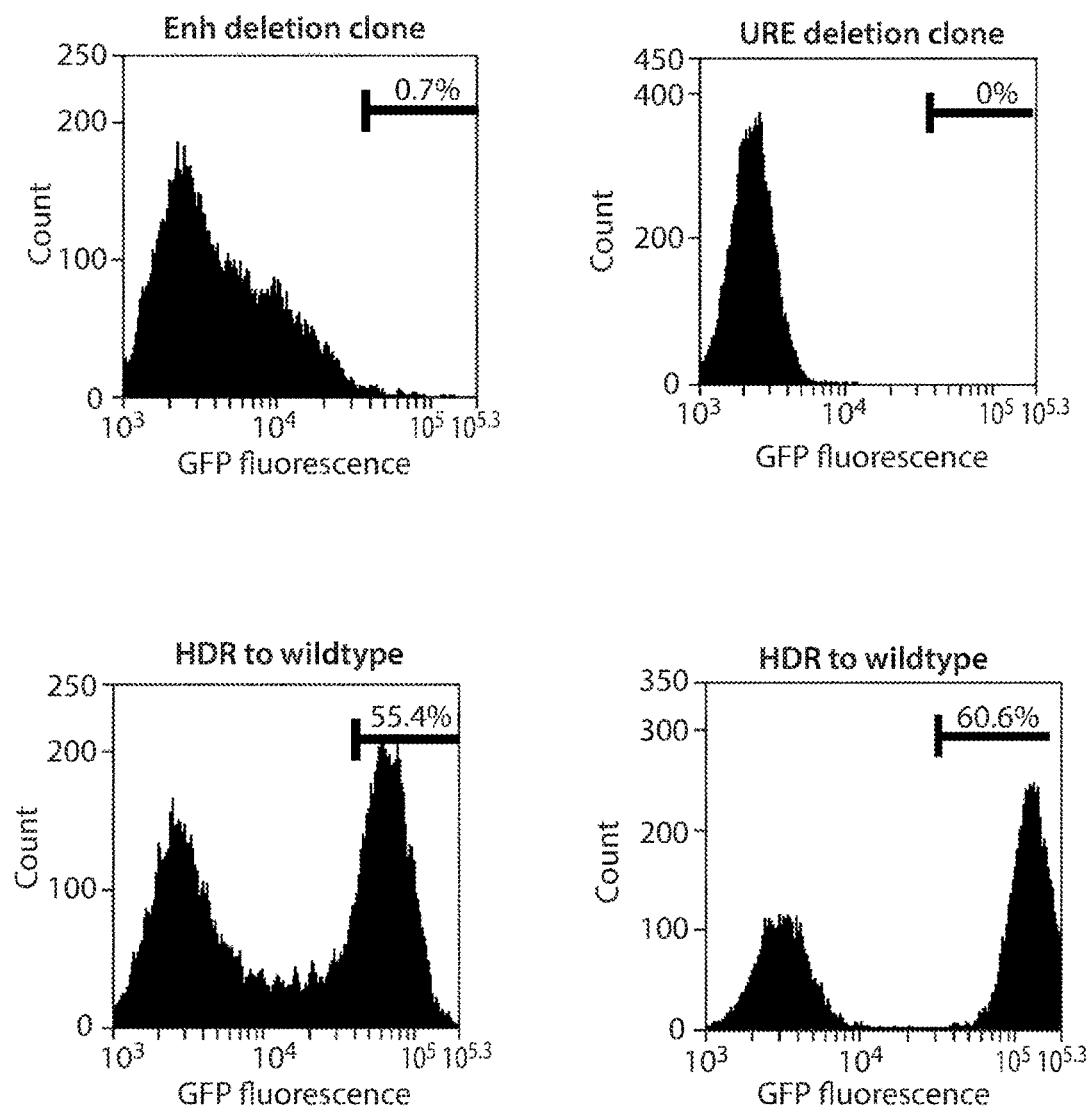
Figure 6C:
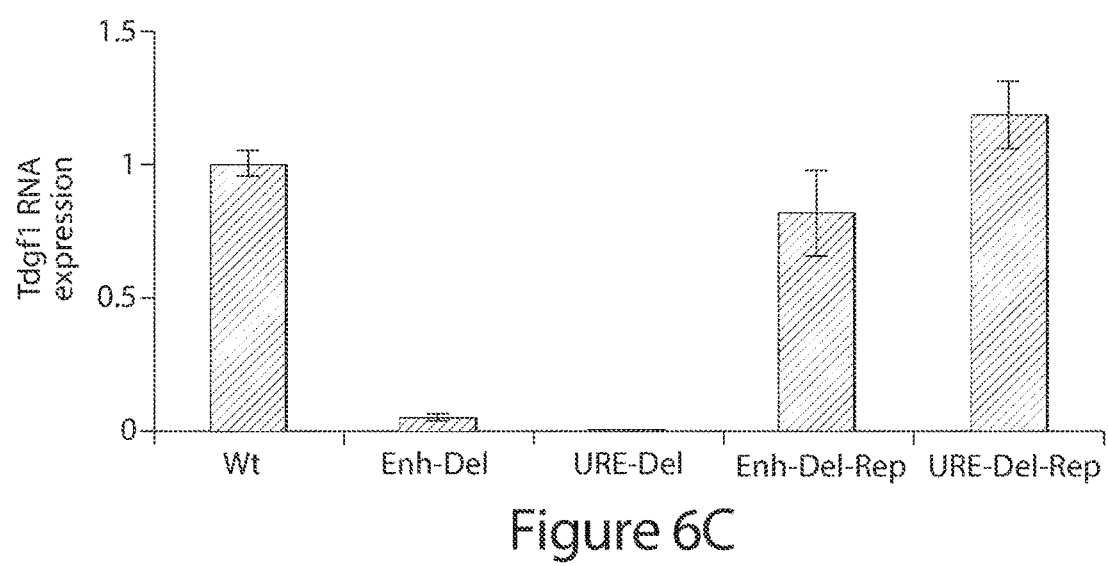

We then used homologous recombination to validate that the Tdgf1 enhancer and URE regulatory elements are truly required for gene expression in the third phase of MERA. We used flanking gRNAs to induce short (>100 bp) deletions in two regions predicted to induce GFP loss by our MERA screen, one in the Tdgf1 enhancer and one at a URE. As expected, a subset of cells lost GFP expression, and we obtained clonal GFP$^{neg}$ lines containing the deletion genotype (FIGS. 6A, 6B). We then used homology-directed repair to restore the wildtype genotype in these cells, finding at each site that a large percentage of cells reverted to a GFP$^{pos}$ state (FIG. 6C). We replicated this experiment in wildtype cells without a Tdgf1-GFP allele, finding that clonal deletion cells lost Tdgf1 RNA expression, and clonal repaired lines restored Tdgf1 expression (FIGS. 6A-6C). This robust and straightforward relationship between local genotype and GFP expression provides compelling evidence that the local DNA sequence at a URE is required for Tdgf1 expression.

In conclusion, MERA offers a new unbiased, high-resolution approach to directly interrogate the regulatory genome for function. MERA not only provides a survey of required cis-regulatory elements, it also enables functional motif discovery to dissect the precise nature of identified regulatory elements.

MERA enabled us to discover unmarked regulatory elements (UREs) that are not associated with conventionally expected DNase hypersensitivity and histone mark features. This observation reinforces the importance of direct perturbation analysis to definitively characterize genome function, as we observe that correlative analysis is insufficient. While we do not yet have definitive data as to the function of UREs, we find that a URE downstream of the Tdgf1 gene is highly sensitive to base substitution at a string of consecutive bases, suggesting that its DNA sequence is crucial to its regulatory activity. Further, we find the first half of this URE to be highly conserved (phastcons score>0.85, data not shown) indicating potential functional significance of the genomic region. Consistent with these data, UREs may be RNA templates (data not shown), elements bound by uncharacterized protein factors, or spacers where their precise base sequence is of secondary importance.

We designed our gRNA libraries to target a mix of previously annotated and unannotated cis-regulatory regions, and thus we did not uniformly tile the proximal regions of any of these genes. Therefore, we cannot estimate the frequency of UREs and expect that future MERA screens with even more extensive coverage at more loci will elucidate how pervasive UREs are in the regulatory architecture of the genome.

MERA is complementary to high-throughput reporter assays, which assess elements sufficient to induce gene expression, and future experiments performing both approaches on a defined cohort of regions should provide insight into the degree of concordance between necessary and sufficient gene regulatory elements. MERA also enables quantitative assessment of the relative contributions of distinct cis-regulatory elements on gene expression, and future studies will provide important insights into how regulatory regions combine to achieve desired levels of expression. Lastly, extending MERA to explore how changes in individual cis-regulatory elements alter gene networks will aid our understanding of how cis-regulatory variants lead to human disease. We expect that the direct interrogation of variant locations discovered in genome wide association studies by MERA will provide a rapid way to screen such variants for function in relevant cell types.

REFERENCES

1. Jenuwein, T. & Allis, C. D. Translating the histone code. *Science* 293, 1074-1080 (2001).
2. Bernstein, B. E. et al. A bivalent chromatin structure marks key developmental genes in embryonic stem cells. *Cell* 125, 315-326 (2006).
3. Rada-Iglesias, A. et al. A unique chromatin signature uncovers early developmental enhancers in humans. *Nature* 470, 279-283 (2011).
4. Heintzman, N. D. et al. Histone modifications at human enhancers reflect global cell-type-specific gene expression. *Nature* 459, 108-112 (2009).
5. Creyghton, M. P. et al. Histone H3K27ac separates active from poised enhancers and predicts developmental state.

Proceedings of the National Academy of Sciences of the United States of America 107, 21931-21936 (2010).
6. Melnikov, A. et al. Systematic dissection and optimization of inducible enhancers in human cells using a massively parallel reporter assay. *Nature biotechnology* 30, 271-277 (2012).
7. Arnold, C. D. et al. Genome-wide quantitative enhancer activity maps identified by STARR-seq. *Science* 339, 1074-1077 (2013).
8. Patwardhan, R. P. et al. Massively parallel functional dissection of mammalian enhancers in vivo. *Nature biotechnology* 30, 265-270 (2012).
9. Fullwood, M. J. et al. An oestrogen-receptor-alpha-bound human chromatin interactome. *Nature* 462, 58-64 (2009).
10. Lieberman-Aiden, E. et al. Comprehensive mapping of long-range interactions reveals folding principles of the human genome. *Science* 326, 289-293 (2009).
11. Simonis, M. et al. Nuclear organization of active and inactive chromatin domains uncovered by chromosome conformation capture-on-chip (4C). *Nature genetics* 38, 1348-1354 (2006).
12. Dostie, J. et al. Chromosome Conformation Capture Carbon Copy (5C): a massively parallel solution for mapping interactions between genomic elements. *Genome research* 16, 1299-1309 (2006).
13. Jinek, M. et al. A programmable dual-RNA-guided DNA endonuclease in adaptive bacterial immunity. *Science* 337, 816-821 (2012).
14. Cong, L. et al. Multiplex genome engineering using CRISPR/Cas systems. *Science* 339, 819-823 (2013).
15. Mali, P. et al. RNA-guided human genome engineering via Cas9. *Science* 339, 823-826 (2013).
16. Jinek, M. et al. RNA-programmed genome editing in human cells. *eLife* 2, e00471 (2013).
17. Fu, Y., Sander, J. D., Reyon, D., Cascio, V. M. & Joung, J. K. Improving CRISPR-Cas nuclease specificity using truncated guide RNAs. *Nature biotechnology* 32, 279-284 (2014).
18. Cho, S. W. et al. Analysis of off-target effects of CRISPR/Cas-derived RNA-guided endonucleases and nickases. *Genome research* 24, 132-141 (2014).
19. Gilbert, L. A. et al. CRISPR-mediated modular RNA-guided regulation of transcription in eukaryotes. *Cell* 154, 442-451 (2013).
20. Fu, Y. et al. High-frequency off-target mutagenesis induced by CRISPR-Cas nucleases in human cells. *Nature biotechnology* 31, 822-826 (2013).
21. Kleinstiver, B. P. et al. Engineered CRISPR-Cas9 nucleases with altered PAM specificities. *Nature* 523, 481-485 (2015).
22. Cradick, T. J., Fine, E. J., Antico, C. J. & Bao, G. CRISPR/Cas9 systems targeting beta-globin and CCR5 genes have substantial off-target activity. *Nucleic acids research* 41, 9584-9592 (2013).
23. Wang, T., Wei, J. J., Sabatini, D. M. & Lander, E. S. Genetic screens in human cells using the CRISPR-Cas9 system. *Science* 343, 80-84 (2014).
24. Shalem, O. et al. Genome-scale CRISPR-Cas9 knockout screening in human cells. *Science* 343, 84-87 (2014).
25. Zhou, Y. et al. High-throughput screening of a CRISPR/Cas9 library for functional genomics in human cells. *Nature* 509, 487-491 (2014).
26. Koike-Yusa, H., Li, Y., Tan, E. P., Velasco-Herrera Mdel, C. & Yusa, K. Genome-wide recessive genetic screening in mammalian cells with a lentiviral CRISPR-guide RNA library. *Nature biotechnology* 32, 267-273 (2014).
27. Chen, S. et al. Genome-wide CRISPR screen in a mouse model of tumor growth and metastasis. *Cell* 160, 1246-1260 (2015).
28. Orlando, S. J. et al. Zinc-finger nuclease-driven targeted integration into mammalian genomes using donors with limited chromosomal homology. *Nucleic acids research* 38, e152 (2010).
29. Young, R. A. Control of the embryonic stem cell state. *Cell* 144, 940-954 (2011).
30. Yue, F. et al. A comparative encyclopedia of DNA elements in the mouse genome. *Nature* 515, 355-364 (2014).
31. Singh, A. M., Hamazaki, T., Hankowski, K. E. & Terada, N. A heterogeneous expression pattern for Nanog in embryonic stem cells. *Stem cells* 25, 2534-2542 (2007).
32. Rajagopal, N. et al. RFECS: a random-forest based algorithm for enhancer identification from chromatin state. *PLoS computational biology* 9, e1002968 (2013).
33. Consortium, E. P. An integrated encyclopedia of DNA elements in the human genome. *Nature* 489, 57-74 (2012).
34. John, S. et al. Chromatin accessibility pre-determines glucocorticoid receptor binding patterns. *Nature genetics* 43, 264-268 (2011).
35. Sherwood, R. I. et al. Discovery of directional and nondirectional pioneer transcription factors by modeling DNase profile magnitude and shape. *Nature biotechnology* 32, 171-178 (2014).
36. Guo, Y., Mahony, S. & Gifford, D. K. High resolution genome wide binding event finding and motif discovery reveals transcription factor spatial binding constraints. *PLoS computational biology* 8, e1002638 (2012).
37. Tsai, S. Q. et al. GUIDE-seq enables genome-wide profiling of off-target cleavage by CRISPR-Cas nucleases. *Nature biotechnology* 33, 187-197 (2015).
38. Dixon, J. R. et al. Topological domains in mammalian genomes identified by analysis of chromatin interactions. *Nature* 485, 376-380 (2012).
39. Leung, D. et al. Integrative analysis of haplotype-resolved epigenomes across human tissues. *Nature* 518, 350-354 (2015).
40. Li, G. et al. Extensive promoter-centered chromatin interactions provide a topological basis for transcription regulation. *Cell* 148, 84-98 (2012).
41. Woo, Y. H., Walker, M. & Churchill, G. A. Coordinated expression domains in mammalian genomes. *PloS one* 5, e12158 (2010).
42. Vierstra, J. et al. Functional footprinting of regulatory DNA. *Nature methods* (2015).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A multiplexed editing regulatory assay (MERA) construct comprising: one or more copies of a defective gRNA expression construct wherein each defective gRNA expression construct comprises:
   i. a dummy gRNA that is not homologous to a eukaryotic genome, and is unable to target a Cas nuclease to the genome for a double strand break,
   ii. a guide hairpin sequence,
   iii. a native regulatory region which will be targeted using CRISPR/Cas endonuclease; and
   iv. an operably linked promoter.

2. The MERA construct of claim 1, wherein the eukaryotic genome is a human genome.

3. The MERA construct of claim 1, wherein the gRNA is 19-21 nucleotides in length.

4. The MERA construct of claim 1, wherein the guide hairpin sequence is about 40 nucleotides in length and once transcribed can be bound to a CRISPR/Cas nuclease.

5. A host cell comprising the MERA construct of claim 1.

6. The host cell of claim 5, wherein a single defective gRNA expression construct is integrated into the host cell genome.

7. The host cell of claim 5, wherein 2-10 defective gRNA expression constructs are integrated into the host cell genome.

8. A population of host cells of claim 5.

9. The host cell of claim 5, further comprising a CRISPR/Cas nuclease and/or a coding sequence for the CRISPR/Cas nuclease.

10. The host cell of claim 5, further comprising Cas9 nuclease.

11. The host cell of claim 9 or 10, further comprising a library of exogenous gRNA homology fragments spanning across the targeted native regulatory region, optionally wherein the gRNA homology fragment further comprises a coding sequence for a reporter protein or a reporter fusion protein.

12. A population of cells of claim 11, wherein each cell has integrated into its genome one or more functional gRNA expression construct at the dummy guide locus.

13. The population of cells of claim 12, wherein the genomic integration is in a virus-independent manner.

14. A method comprising:
   (1) introducing into a host cell comprising the MERA construct of claim 1: a library of exogenous gRNA homology fragments spanning across the targeted native regulatory region, wherein the gRNA homology fragment further comprises a coding sequence for a reporter protein or a reporter fusion protein, and
   (2) allowing a single exogenous gRNA homology fragment to homologously recombine with the dummy gRNA construct in the presence of a CRISPR/Cas nuclease to form a functional guide RNA construct, wherein the host cell comprises a reporter gene coding sequence integrated into its genome.

* * * * *

SEQUENCE LISTING

```
<160> NUMBER OF SEQ ID NOS: 176

<210> SEQ ID NO 1
<211> LENGTH: 113
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: n is a, c, g, or u

<400> SEQUENCE: 1
nnnnnnnnnn nnnnnnnnnn guuuaagagc uaugcuggaa acagcauagc aaguuuaaau    60
```
aaggcuaguc cguuaucaac uugaaaaagu ggcaccgagu cggugcuuuu uuu        113

<210> SEQ ID NO 2
<211> LENGTH: 40
<212> TYPE: RNA
<213> ORGANISM: Artificial Sequence
<220> FEATURE:
<223> OTHER INFORMATION: Synthetic Polynucleotide

<400> SEQUENCE: 2
guuuaagagc uaugcuggaa acagcauagc aaguuuaaau        40

<210> SEQ ID NO 3
<211> LENGTH: 100
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(49)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, t, g, or absent

<400> SEQUENCE: 3
ttatatatct tgtggaaagg acgaaacacc gnnnnnnnnn nnnnnnnnnn ngtttaagag        60
ctatgctgga aacagcatag caagtttaaa taaggctagt        100

<210> SEQ ID NO 4
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 4
ccaggttagc ctttaagcct gcccagaaga ctcccgccca gcatgtgagg gcctatttcc        60

<210> SEQ ID NO 5
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 5
ggagaatccc ttccccctct tccctcgtga tctgcatcgc gattttacca catttgtaga        60

<210> SEQ ID NO 6
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 6
cacctgttca attcccctgc aggacaacgc ccacacacca ggttagcctt taagcctgc        59

<210> SEQ ID NO 7
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 7
tctgctgcct cctggcttct gaggaccgcc ctgggcctgg gagaatccct tccccctctt        60

<210> SEQ ID NO 8
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 8
tctacaaatg tggtaaaatc gcga                                              24

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
gggaggggag tgttgcaata                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
tgggaagtct tgtccctcca                                                   20

<210> SEQ ID NO 11
<211> LENGTH: 330
<212> TYPE: DNA
<213> ORGANISM: Mus musculus

<400> SEQUENCE: 11
tcccattttc cttatttgcc cctattaaaa aacttcccga caaaaccgaa aatctgtggg        60
aagtcttgtc cctccaattt tacacctgtt caattcccct gcaggacaac gcccacacac       120
caggttagcc tttaagcctg cccagaagac tcccgcccat cttctagaaa gactggagtt       180
gcagatcacg agggaagagg gggaagggat tctcccaggc ccagggcggt cctcagaagc       240
caggaggcag cagagaactc ccagaaaggt attgcaacac tcccctcccc cctccggaga       300
agggtgcggc cttctccccg cctactccac                                        330

<210> SEQ ID NO 12
<211> LENGTH: 1010
<212> TYPE: DNA
<213> ORGANISM: Artificial Sequence
<220> FEATURE:
<223> OTHER INFORMATION: Synthetic Polynucleotide

<400> SEQUENCE: 12
tcccattttc cttatttgcc cctattaaaa aacttcccga caaaaccgaa aatctgtggg        60
aagtcttgtc cctccaattt tacacctgtt caattcccct gcaggacaac gcccacacac       120
caggttagcc tttaagcctg cccagaagac tcccgcccag catgtgaggg cctatttccc       180
atgattcctt catatttgca tatacgatac aaggctgtta gagagataat tggaattaat       240

```
ttgactgtaa acacaaagat attagtacaa aatacgtgac gtagaaagta ataatttctt        300
gggtagtttg cagttttaaa attatgtttt aaaatggact atcatatgct taccgtaact        360
tgaaagtatt tcgatttctt ggctttatat atcttgtgga aaggacgaaa caccgaggcg        420
tctgggtggc tcttggttta agagctatgc tggaaacagc atagcaagtt taaataaggc        480
tagtccgtta tcaacttgaa aaagtggcac cgagtcggtg ctttttttgtt ttagagctag       540 aaatagcaag ttaaaataag gctagtccgt ttttagcgcg tgcgccaatt ctgcagacaa        600
atggctctag aggtacggcc gcttcgagca gacatgataa gatacattga tgagtttgga       660
caaaccacaa ctagaatgca gtgaaaaaaa tgctttattt gtgaaatttg tgatgctatt        720
gctttatttg taaccattat aagctgcaat aaacaagtta acaacaacaa ttgcattcat        780
tttatgtttc aggttcaggg ggagatgtgg gaggtttttt aaagcaagta aaacctctac        840
aaatgtggta aaatcgcgat gcagatcacg agggaagagg gggaagggat tctcccaggc       900
ccagggcggt cctcagaagc caggaggcag cagagaactc ccagaaaggt attgcaacac        960 tccccctcccc cctccggaga agggtgcggc cttctccccg cctactccac                1010
```

<210> SEQ ID NO 13  
<211> LENGTH: 20  
<212> TYPE: DNA  
<213> ORGANISM: Artificial Sequence  
<220> FEATURE:  
<223> OTHER INFORMATION: Synthetic Polynucleotide

<400> SEQUENCE: 13

```
gaaacaccga ggcgtctggg                                                    20
```

<210> SEQ ID NO 14  
<211> LENGTH: 21  
<212> TYPE: DNA  
<213> ORGANISM: Artificial Sequence  
<220> FEATURE:  
<223> OTHER INFORMATION: Synthetic Polynucleotide

<400> SEQUENCE: 14

```
gagatggggt acttctcatc c                                                  21
```

<210> SEQ ID NO 15  
<211> LENGTH: 215  
<212> TYPE: DNA  
<213> ORGANISM: Mus musculus

<400> SEQUENCE: 15

```
ttgggtgttt cgagaatggc tttatgaact aaagccatct gctaatattg tgtttcttgt         60
cttttcctcc aacgttttta cgagccgtcg aagatggggt acttctcatc caggtatgag        120
ctaaccttga cttttggtt gctggagata gccacttcgg aaaatcacgt tctatgacgc         180
tctgattttt gtcttgcttg aaccttgtca gtaac                                   215
```

<210> SEQ ID NO 16  
<211> LENGTH: 1519  
<212> TYPE: DNA  
<213> ORGANISM: Artificial Sequence  
<220> FEATURE:  
<223> OTHER INFORMATION: Synthetic Polynucleotide

<400> SEQUENCE: 16

```
ctctctcatt tggcatatct ttctttttaa tctactgttt tcattttgtg aaattagcct         60
ttgggtgttt cgagaatggc tttatgaact aaagccatct gctaatattg tgtttcttgt        120
```

-continued

```
cttttcctcc aacgttttta cgagccgtcg aagatggtga gcaagggcga ggagctgttc      180
accggggtgg tgcccatcct ggtcgagctg gacggcgacg taaacggcca caagttcagc      240
gtgtccggcg agggcgaggg cgatgccacc tacggcaagc tgacccctga agttcatctg      300
accaccggca agctgcccgt gccctggccc accctcgtga ccaccctgac ctacggcgtg      360
cagtgcttca gccgctaccc cgaccacatg aagcagcacg acttcttcaa gtccgccatg      420
cccgaaggct acgtccagga gcgcaccatc ttcttcaagg acgacggcaa ctacaagacc      480
cgcgccgagg tgaagttcga gggcgacacc ctggtgaacc gcatcgagct gaagggcatc      540
gacttcaagg aggacggcaa catcctgggg cacaagctgg agtacaacta caacagccac      600
aacgtctata tcatggccga caagcagaag aacggcatca aggtgaactt caagatccgc      660
cacaacatcg aggacggcag cgtgcagctc gccgaccact accagcagaa cacccccatc      720
ggcgacggcc ccgtgctgct gcccgacaac cactacctga gcacccagtc cgccctgagc      780
aaagacccca cgagaagcg cgatcacatg gtcctgctgg agttcgtgac cgccgccggg      840
atcactctcg gcatggacga gctgtacaag taaagcggcc gcaattcact cctcaggtgc      900
aggctgccta tcagaaggtg gtggctggtg tggccaatgc ccttgctcac catggtgaag      960
ggtgggcgcg ccgacccagc tttcttgtac aaagtggttg atctagaggg cccgcggttc     1020
gaaggtaagc ctatccctaa ccctctcctc ggtctcgatt ctacgcgtac cggtcatcat     1080
caccatcacc attgagttta tccatcacac tggcggccgc tcgaggggga tccactagtt     1140
ctagagcggc cgcttcgagc agacatgata agatacattg atgagtttgg acaaaccaca     1200
actagaatgc agtgaaaaaa atgctttatt tgtgaaattt gtgatgctat tgctttattt     1260
gtaaccatta taagctgcaa taaacaagtt aacaacaaca attgcattca ttttatgttt     1320
caggttcagg gggagatgtg ggaggttttt taaagcaagt aaaacctcta caaatgtggt     1380
aaaatcgcga gagctaacct tgacttttg gttgctggag atagccactt cggaaaatca     1440
cgttctatga cgctctgatt tttgtcttgc ttgaaccttg tcagtaacat tgctgctttt     1500
cctgaagaac ctggaactt                                                   1519
```

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17

```
gaatgaacaa atgaagaaaa                                                    20
```

<210> SEQ ID NO 18
<211> LENGTH: 226
<212> TYPE: DNA
<213> ORGANISM: Mus musculus

<400> SEQUENCE: 18

```
tgggttatta tctaaggcag gtgtttgcgg atcagtgccc cctggaagtg agtcataggc       60
attgttcaag aaggaagcag ctaagacaac atgaatgaac aaaaaatgaa tgaacaaatg      120 aagaaacgg caaagacaag tggccagaaa gggccgggcg aagagccct cgacagactg       180 accctaaagc aagacgaggc aaggccagtc cagaatacca gagtgg                     226
```

<210> SEQ ID NO 19

```
<211> LENGTH: 1438
<212> TYPE: DNA
<213> ORGANISM: Artificial Sequence
<220> FEATURE:
<223> OTHER INFORMATION: Synthetic Polynucleotide

<400> SEQUENCE: 19
tgggttatta tctaaggcag gtgtttgcgg atcagtgccc cctggaagtg agtcataggc      60
attgttcaag aaggaagcag ctaagacaac atgaatgaac aaaaaatgaa tgtgagcaag     120
ggcgaggagc tgttcaccgg ggtggtgccc atcctggtcg agctggacgg cgacgtaaac    180
ggccacaagt tcagcgtgtc cggcgagggc gagggcgatg ccacctacgg caagctgacc    240
ctgaagttca tctgcaccac cggcaagctg cccgtgccct ggcccaccct cgtgaccacc    300
ctgacctacg gcgtgcagtg cttcagccgc taccccgacc acatgaagca gcacgacttc    360
ttcaagtccg ccatgcccga aggctacgtc caggagcgca ccatcttctt caaggacgac    420
ggcaactaca agacccgcgc cgaggtgaag ttcgagggcg acaccctggt gaaccgcatc    480
gagctgaagg gcatcgactt caaggaggac ggcaacatcc tggggcacaa gctggagtac    540
aactacaaca gccacaacgt ctatatcatg gccgacaagc agaagaacgg catcaaggtg    600
aacttcaaga tccgccacaa catcgaggac ggcagcgtgc agctcgccga ccactaccag    660
cagaacaccc ccatcggcga cggccccgtg ctgctgcccg acaaccacta cctgagcacc    720
cagtccgccc tgagcaaaga ccccaacgag aagcgcgatc acatggtcct gctggagttc    780
gtgaccgccg ccgggatcac tctcggcatg gacgagctgt acaagtaaag cggccgcaat    840
tcactcctca ggtgcaggct gcctatcaga aggtggtggc tggtgtggcc aatgcccttg    900
ctcaccatgg tgaagggtgg cgcgccgac ccagctttct tgtacaaagt ggttgatcta     960
gagggcccgc ggttcgaagg taagcctatc cctaaccctc tcctcggtct cgattctacg   1020
cgtaccggtc atcatcacca tcaccattga gtttatccat cacactggcg gccgctcgag   1080
ggggatccac tagttctaga gcggccgctt cgagcagaca tgataagata cattgatgag   1140
tttggacaaa ccacaactag aatgcagtga aaaaaatgct ttatttgtga atttgtgat    1200
gctattgctt tatttgtaac cattataagc tgcaataaac aagttaacaa caacaattgc   1260
attcatttta tgtttcaggt tcaggggggag atgtgggagg ttttttaaag caagtaaaac   1320
ctctacaaat gtggtaaaat cgcgaagaca agtggccaga aagggccggg cggaagagcc   1380
ctcgacagac tgaccctaaa gcaagacgag gcaaggccag tccagaatac cagagtgg    1438

<210> SEQ ID NO 20
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 20
gtatgagact tacgcaacat c                                                21

<210> SEQ ID NO 21
<211> LENGTH: 276
<212> TYPE: DNA
<213> ORGANISM: Mus musculus

<400> SEQUENCE: 21
gcagccttac gtacagttgc agcaaaactt ctctgccagt gatttggagg tgaatttgga     60
agccactagg gaaagccatg cgcatttag cacccacaa gccttggaat tattcctgaa     120
```
ctactctgtg actccaccag gtgaaatatg agacttacgc aacatctggg cttaaagtca    180
gggcaaagcc aggttccttc cttcttccaa atattttcat attttttta aagatttatt    240 tattcattat atgtaagtac actgtagctg tcttca                              276

```
<210> SEQ ID NO 22
<211> LENGTH: 1003
<212> TYPE: DNA
<213> ORGANISM: Artificial Sequence
<220> FEATURE:
<223> OTHER INFORMATION: Synthetic Polynucleotide

<400> SEQUENCE: 22
```
gcagccttac gtacagttgc agcaaaactt ctctgccagt gatttggagg tgaatttgga     60
agccactagg gaaagccatg cgcattttag caccccacaa gccttggaat tattcctgaa    120
ctactctgtg actccaccag gtgaaatagt gagcaagggc gaggagctgt tcaccggggt    180
ggtgcccatc ctggtcgagc tggacggcga cgtaaacggc cacaagttca gcgtgtccgg    240
cgagggcgag ggcgatgcca cctacggcaa gctgaccctg aagttcatct gcaccaccgg    300
caagctgccc gtgccctggc ccaccctcgt gaccaccctg acctacggcg tgcagtgctt    360
cagccgctac cccgaccaca tgaagcagca cgacttcttc aagtccgcca tgcccgaagg    420
ctacgtccag gagcgcacca tcttcttcaa ggacgacggc aactacaaga cccgcgccga    480
ggtgaagttc gagggcgaca ccctggtgaa ccgcatcgag ctgaagggca tcgacttcaa    540
ggaggacggc aacatcctgg ggcacaagct ggagtacaac tacaacagcc acaacgtcta    600
tatcatggcc gacaagcaga agaacggcat caaggtgaac ttcaagatcc gccacaacat    660
cgaggacggc agcgtgcagc tcgccgacca ctaccagcag aacacccccc tcggcgacgg    720
ccccgtgctg ctgcccgaca accactacct gagcacccag tccgccctga gcaaagaccc    780
caacgagaag cgcgatcaca tggtcctgct ggagttcgtg accgccgccg ggatcactct    840
cggcatggac gagctgtaca agtaaagcgg ccgcaattca ctcctcaaac atctgggctt    900
aaagtcaggg caaagccagg ttccttcctt cttccaaata ttttcatatt ttttttaaag    960
atttatttat tcattatatg taagtacact gtagctgtct tca                     1003

```
<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23
```
gctcagaggc gagaattctc                                                 20

```
<210> SEQ ID NO 24
<211> LENGTH: 249
<212> TYPE: DNA
<213> ORGANISM: Mus musculus

<400> SEQUENCE: 24
```
ctcagtcctg gtccttcgtc ccctcctacg gtgtcgacgt ccaagaggag cctgggggaa     60
tctgctgctg aagaaggcac cgctaagcgg tctcagcctg agccagaggc tgagaatgag    120
gacaggaccg cctgagaatt ctcgcctctg agccacccag accgactgaa tcatatatct    180
tcaacactcc tgcataacct tcaacacacg cacctttcat acctgggttt taaggggccc    240
atgttcctg                                                              249

<210> SEQ ID NO 25
<211> LENGTH: 973
<212> TYPE: DNA
<213> ORGANISM: Artificial Sequence
<220> FEATURE:
<223> OTHER INFORMATION: Synthetic Polynucleotide

<400> SEQUENCE: 25
ctcagtcctg gtccttcgtc ccctcctacg gtgtcgacgt ccaagaggag cctgggggaa      60
tctgctgctg aagaaggcac cgctaagcgg tctcagcctg agccagaggc tgagaatgag     120
gacaggaccg ccgtgagcaa gggcgaggag ctgttcaccg gggtggtgcc catcctggtc     180
gagctggacg gcgacgtaaa cggccacaag ttcagcgtgt ccggcgaggg cgagggcgat     240
gccacctacg gcaagctgac cctgaagttc atctgcacca ccggcaagct gcccgtgccc     300
tggcccaccc tcgtgaccac cctgacctac ggcgtgcagt gcttcagccg ctaccccgac     360
cacatgaagc agcacgactt cttcaagtcc gccatgcccg aaggctacgt ccaggagcgc     420
accatcttct tcaaggacga cggcaactac aagacccgcg ccgaggtgaa gttcgagggc     480
gacaccctgg tgaaccgcat cgagctgaag ggcatcgact tcaaggagga cggcaacatc     540
ctggggcaca agctggagta caactacaac agccacaacg tctatatcat ggccgacaag     600
cagaagaacg gcatcaaggt gaacttcaag atccgccaca acatcgagga cggcagcgtg     660
cagctcgccg accactacca gcagaacacc cccatcggcg acggccccgt gctgctgccc     720
gacaaccact acctgagcac ccagtccgcc ctgagcaaag accccaacga gaagcgcgat     780
cacatggtcc tgctggagtt cgtgaccgcc gccgggatca ctctcggcat ggacgagctg     840
tacaagtaaa gcggccgcaa ttcactcctc actgagccac ccagaccgac tgaatcatat     900
atcttcaaca ctcctgcata cctttcaaca cacgcacctt tcatacctgg gttttaaggg     960
gcccatgttc ctg                                                         973

<210> SEQ ID NO 26
<211> LENGTH: 100
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(49)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, t, g, or absent

<400> SEQUENCE: 26
ttatatatct tgtggaaagg acgaaacacc gnnnnnnnnn nnnnnnnnnn ngtttaagag      60
ctatgctgga aacagcatag caagtttaaa taaggctagt                           100

<210> SEQ ID NO 27
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 27
ttatatatct tgtggaaagg acgaaacacc gggcgaggag ctgttcaccg gtttaagagc      60
tatgctggaa acagcatagc aagtttaaat aaggctagt        99

<210> SEQ ID NO 28
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 28
ttatatatct tgtggaaagg acgaaacacc gaccaggatg ggcaccaccc gtttaagagc        60
tatgctggaa acagcatagc aagtttaaat aaggctagt        99

<210> SEQ ID NO 29
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 29
ttatatatct tgtggaaagg acgaaacacc gagctggacg gcgacgtaaa gtttaagagc        60
tatgctggaa acagcatagc aagtttaaat aaggctagt        99

<210> SEQ ID NO 30
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 30
ttatatatct tgtggaaagg acgaaacacc ggcatcgccc tcgccctcgc gtttaagagc        60
tatgctggaa acagcatagc aagtttaaat aaggctagt        99

<210> SEQ ID NO 31
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 31
ttatatatct tgtggaaagg acgaaacacc gcttcagggt cagcttgccg tgtttaagag        60
ctatgctgga aacagcatag caagtttaaa taaggctagt        100

<210> SEQ ID NO 32
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 32
ttatatatct tgtggaaagg acgaaacacc gggcacgggc agcttgccgg gtttaagagc        60
tatgctggaa acagcatagc aagtttaaat aaggctagt        99

<210> SEQ ID NO 33
<211> LENGTH: 99
<212> TYPE: DNA
<213> ORGANISM: Artificial Sequence
<220> FEATURE:

<223> OTHER INFORMATION: Synthetic Polynucleotide

<400> SEQUENCE: 33
ttatatatct tgtggaaagg acgaaacacc ggtcagggtg gtcacgaggg gtttaagagc    60
tatgctggaa acagcatagc aagtttaaat aaggctagt                          99

<210> SEQ ID NO 34
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 34
ttatatatct tgtggaaagg acgaaacacc gcttcatgtg gtcggggtag gtttaagagc    60
tatgctggaa acagcatagc aagtttaaat aaggctagt                          99

<210> SEQ ID NO 35
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 35
ttatatatct tgtggaaagg acgaaacacc gacgtagcct tcgggcatgg gtttaagagc    60
tatgctggaa acagcatagc aagtttaaat aaggctagt                          99

<210> SEQ ID NO 36
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 36
ttatatatct tgtggaaagg acgaaacacc ggagcgcacc atcttcttca gtttaagagc    60
tatgctggaa acagcatagc aagtttaaat aaggctagt                          99

<210> SEQ ID NO 37
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 37
tgttttaaaa tggactatca tatgcttacc gtaacttgaa agtatttcga tttcttggct    60
ttatatatct tgtggaaagg acgaaacacc                                    90

<210> SEQ ID NO 38
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 38
ctcggtgcca cttttcaag ttgataacgg actagcctta tttaaacttg ctatgctgtt     60

<210> SEQ ID NO 39
<211> LENGTH: 189

<212> TYPE: DNA
<213> ORGANISM: Artificial Sequence
<220> FEATURE:
<223> OTHER INFORMATION: Synthetic Polynucleotide

<400> SEQUENCE: 39

```
tgttttaaaa tggactatca tatgcttacc gtaacttgaa agtatttcga tttcttggct    60
ttatatatct tgtggaaagg acgaaacacc gggcgaggag ctgttcaccg gtttaagagc   120
tatgctggaa acagcatagc aagtttaaat aaggctagtc cgttatcaac ttgaaaaagt   180
ggcaccgag                                                           189
```

<210> SEQ ID NO 40
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 40

```
ttgtggaaag gacgaaacac c                                              21
```

<210> SEQ ID NO 41
<211> LENGTH: 576
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (23)..(40)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, t, g, or absent

<400> SEQUENCE: 41

```
ttgtggaaag gacgaaacac cgnnnnnnnn nnnnnnnnnn nngtttaaga gctatgctgg    60
aaacagcata gcaagtttaa ataaggctag tccgttatca acttgaaaaa gtggcaccga   120
gtcggtgctt ttttgtttta gagctagaaa tagcaagtta aaataaggct agtccgtttt   180
tagcgcgtgc gccaattctg cagacaaatg gctctagagg tacggccgct tcgagcagac   240
atgataagat acattgatga gtttggacaa accacaacta gaatgcagtg aaaaaaatgc   300
tttatttgtg aaatttgtga tgctattgct ttatttgtaa ccattataag ctgcaataaa   360
caagttaaca acaacaattg cattcatttt atgtttcagg ttcaggggga gatgtgggag   420
gttttttaaa gcaagtaaaa cctctacaaa tgtggtaaaa tcgcgatgca gatcacgagg   480
gaagaggggg aagggattct cccaggccca gggcggtcct cagaagccag gaggcagcag   540
agaactccca gaaaggtatt gcaacactcc cctccc                             576
```

<210> SEQ ID NO 42
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 42

```
ttgtggaaag gacgaaacac c                                              21
```

<210> SEQ ID NO 43

```
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 43
gccttattta aacttgctat gctgt                                          25

<210> SEQ ID NO 44
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 44
ctctttccct acacgacgct cttccgatct aactcttgtg gaaaggacga aacacc        56

<210> SEQ ID NO 45
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 45
ctctttccct acacgacgct cttccgatct ctggattgtg gaaaggacga aacacc        56

<210> SEQ ID NO 46
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 46
ctctttccct acacgacgct cttccgatct ggactttgtg gaaaggacga aacacc        56

<210> SEQ ID NO 47
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 47
ctctttccct acacgacgct cttccgatct tctgcttgtg gaaaggacga aacacc        56

<210> SEQ ID NO 48
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 48
ctctttccct acacgacgct cttccgatct aaccgttgtg gaaaggacga aacacc        56

<210> SEQ ID NO 49
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 49
```
ctctttccct acacgacgct cttccgatct ctctgttgtg gaaaggacga aacacc          56

<210> SEQ ID NO 50
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 50
ctctttccct acacgacgct cttccgatct ggtaattgtg gaaaggacga aacacc          56

<210> SEQ ID NO 51
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 51
ctctttccct acacgacgct cttccgatct aagctttgtg gaaaggacga aacacc          56

<210> SEQ ID NO 52
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 52
ctctttccct acacgacgct cttccgatct tcgtcttgtg gaaaggacga aacacc          56

<210> SEQ ID NO 53
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 53
ctctttccct acacgacgct cttccgatct ccaatttgtg gaaaggacga aacacc          56

<210> SEQ ID NO 54
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 54
ctctttccct acacgacgct cttccgatct gcgtattgtg gaaaggacga aacacc          56

<210> SEQ ID NO 55
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 55
ctctttccct acacgacgct cttccgatct tgagcttgtg gaaaggacga aacacc          56

<210> SEQ ID NO 56
<211> LENGTH: 53
<212> TYPE: DNA

<213> ORGANISM: Artificial Sequence
<220> FEATURE:
<223> OTHER INFORMATION: Synthetic Polynucleotide

<400> SEQUENCE: 56
cattcctgct gaaccgctct tccgatctgc cttatttaaa cttgctatgc tgt         53

<210> SEQ ID NO 57
<211> LENGTH: 142
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (50)..(67)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, t, g, or absent

<400> SEQUENCE: 57
ctctttccct acacgacgct cttccgatct aactcttgtg gaaaggacgn nnnnnnnnn    60 nnnnnnnnng tttaagagct atgctggaaa cagcatagca agtttaaata aggcagatcg  120
gaagagcggt tcagcaggaa tg                                            142

<210> SEQ ID NO 58
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 58
aatgatacgg cgaccaccga gatctacact ctttccctac acgacgctct tccgatct    58

<210> SEQ ID NO 59
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 59
caagcagaag acggcatacg agatcggtct cggcattcct gctgaaccgc tcttccgatc  60
t                                                                    61

<210> SEQ ID NO 60
<211> LENGTH: 211
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (86)..(103)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, t, g, or absent

<400> SEQUENCE: 60
aatgatacgg cgaccaccga gatctacact ctttccctac acgacgctct tccgatctaa  60
ctcttgtgga aaggacgaaa caccgnnnnn nnnnnnnnnn nnnngttta agagctatgc   120 tggaaacagc atagcaagtt taaataaggc agatcggaag agcggttcag caggaatgcc        180
gagaccgatc tcgtatgccg tcttctgctt g                                      211

<210> SEQ ID NO 61
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 61
taacttgaaa gtatttcgat ttcttggctt tatatatctt gtggaaagga cgaaacaccg        60

<210> SEQ ID NO 62
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 62
gttgataacg gactagcctt atttaaactt gctatgctgt ttccagcata gctcttaaac        60

<210> SEQ ID NO 63
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 63
atttcttggg tagtttgcag ttttaaaatt atgttttaaa atggactatc atatgcttac        60
cgtaacttga aagtatttcg atttcttggc                                        90

<210> SEQ ID NO 64
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 64
attttaactt gctatttcta gctctaaaac aaaaaagcac cgactcggtg ccacttttc       60 aagttgataa cggactagcc ttatttaaac                                        90

<210> SEQ ID NO 65
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 65
cgatacaagg ctgttagaga gataattaga attaatttga ctgtaaacac aaagatatta       60
gtacaaaata cgtgacgtag aaagtaataa                                        90

<210> SEQ ID NO 66
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 66
tcaatgtatc ttatcatgtc tgctcgattt taacttgcta tttctagctc taaaacaaaa    60

<210> SEQ ID NO 67
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 67
tggaaaggac gaaacaccgg catcgccctc gccctcgcgt ttaagagcta tgctggaaac    60

<210> SEQ ID NO 68
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 68
tggaaaggac gaaacaccga gtgagatcca ggtgatccgt ttaagagcta tgctggaaac    60

<210> SEQ ID NO 69
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 69
ggaaaggacg aaacaccgca aacagctcca tacccaaggt ttaagagcta tgctggaaac    60

<210> SEQ ID NO 70
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 70
tggaaaggac gaaacaccgc aagcaccacc ctacttgggt ttaagagcta tgctggaaac    60

<210> SEQ ID NO 71
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 71
ggaaaggacg aaacaccgcc atcccctgcc ggtctacagt ttaagagcta tgctggaaac    60

<210> SEQ ID NO 72
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 72
tggaaaggac gaaacaccgg gggtgagggg caattgggtt taagagctat gctggaaaca    60

<210> SEQ ID NO 73
<211> LENGTH: 60

<212> TYPE: DNA
<213> ORGANISM: Artificial Sequence
<220> FEATURE:
<223> OTHER INFORMATION: Synthetic Polynucleotide

<400> SEQUENCE: 73
ggaaaggacg aaacaccgaa ttcctgcttc ttaccacggt ttaagagcta tgctggaaac    60

<210> SEQ ID NO 74
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 74
tggaaaggac gaaacaccga acaaaagcc acaaacagtt taagagctat gctggaaaca    60

<210> SEQ ID NO 75
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 75
ggaaaggacg aaacaccgat ggttagcatt ccgggtgcgt ttaagagcta tgctggaaac    60

<210> SEQ ID NO 76
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 76
ggaaaggacg aaacaccgtt atgggcaagc tgtgtcccgt ttaagagcta tgctggaaac    60

<210> SEQ ID NO 77
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 77
tggaaaggac gaaacaccgg ggaagtgact aagactggtt taagagctat gctggaaaca    60

<210> SEQ ID NO 78
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 78
tggaaaggac gaaacaccgc catagttttc cagaaaggtt taagagctat gctggaaaca    60

<210> SEQ ID NO 79
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 79
ggaaaggacg aaacaccgtc tgaaggagac aatgacaagt ttaagagcta tgctggaaac          60

<210> SEQ ID NO 80
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 80
ggaaaggacg aaacaccgcc catccctgt cactctgagt tcgtttaaga gctatgctgg          60
aaac                                                                     64

<210> SEQ ID NO 81
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 81
ggaaaggacg aaacaccgat aattccttta gtctacatgt ttaagagcta tgctggaaac         60

<210> SEQ ID NO 82
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 82
tggaaaggac gaaacaccgg gattctggga aaacattggt ttaagagcta tgctggaaac         60

<210> SEQ ID NO 83
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 83
ggaaaggacg aaacaccgct ctcaggactt gtccacacgt ttaagagcta tgctggaaac         60

<210> SEQ ID NO 84
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 84
ggaaaggacg aaacaccgtt tcctaagccc tagctggagt ttaagagcta tgctggaaac         60

<210> SEQ ID NO 85
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 85
ggaaaggacg aaacaccgtt agaaattagt gcagtgttgt ttaagagcta tgctggaaac         60

<210> SEQ ID NO 86
<211> LENGTH: 60

<212> TYPE: DNA
<213> ORGANISM: Artificial Sequence
<220> FEATURE:
<223> OTHER INFORMATION: Synthetic Polynucleotide

<400> SEQUENCE: 86
ggaaaggacg aaacaccgaa tcttcccaat tgtctcctgt ttaagagcta tgctggaaac    60

<210> SEQ ID NO 87
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 87
tggaaaggac gaaacaccgt caactaaacc aacacttagt ttaagagcta tgctggaaac    60

<210> SEQ ID NO 88
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 88
ggaaaggacg aaacaccgtc tttcaaaaca agacccaagt ttaagagcta tgctggaaac    60

<210> SEQ ID NO 89
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 89
ggaaaggacg aaacaccgtt tctgtccagg acactgatgt ttaagagcta tgctggaaac    60

<210> SEQ ID NO 90
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 90
ggaaaggacg aaacaccgaa aaaactagtc aacattccgt ttaagagcta tgctggaaac    60

<210> SEQ ID NO 91
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 91
ggaaaggacg aaacaccgct gtgagccctt tgtaaggagt ttaagagcta tgctggaaac    60

<210> SEQ ID NO 92
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 92
ggaaaggacg aaacaccgac tgcatccaca gactgggcgt ttaagagcta tgctggaaac    60

<210> SEQ ID NO 93
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 93
ggaaaggacg aaacaccgcc ctcaccccct agggtttcgt ttaagagcta tgctggaaac    60

<210> SEQ ID NO 94
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 94
tggaaaggac gaaacaccgt ttcttcattg tcagagagtt taagagctat gctggaaaca    60

<210> SEQ ID NO 95
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 95
ggaaaggacg aaacaccgtt cttccttgct ttcttttggt ttaagagcta tgctggaaac    60

<210> SEQ ID NO 96
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 96
tggaaaggac gaaacaccga attttccttc atcattttgt ttaagagcta tgctggaaac    60

<210> SEQ ID NO 97
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 97
ggaaaggacg aaacaccgtt cagcacagca gatgctctgt ttaagagcta tgctggaaac    60

<210> SEQ ID NO 98
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 98
tggaaaggac gaaacaccga acagcttttt agatgtgagt ttaagagcta tgctggaaac    60

<210> SEQ ID NO 99
<211> LENGTH: 60
<212> TYPE: DNA
<213> ORGANISM: Artificial Sequence

```
<220> FEATURE:
<223> OTHER INFORMATION: Synthetic Polynucleotide

<400> SEQUENCE: 99
tggaaaggac gaaacaccga tttagaatcc cctaaggagt ttaagagcta tgctggaaac    60

<210> SEQ ID NO 100
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 100
ggaaaggacg aaacaccgtc cgagactgcg gctcttacgt ttaagagcta tgctggaaac    60

<210> SEQ ID NO 101
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 101
ggaaaggacg aaacaccgtc ggatgacctg agtagagcgt ttaagagcta tgctggaaac    60

<210> SEQ ID NO 102
<211> LENGTH: 87
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (59)..(63)
<223> OTHER INFORMATION: n is a, c, g, or t

<400> SEQUENCE: 102
aatgatacgg cgaccaccga gatctacact ctttccctac acgacgctct tccgatctnn    60
nnngccgaaa ggatgggagt actaagc                                        87

<210> SEQ ID NO 103
<211> LENGTH: 281
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (216)..(220)
<223> OTHER INFORMATION: n is a, c, g, or t

<400> SEQUENCE: 103
acgcccagtc tctctactcc cccccacccc catcccctgt cactctgagt ttccagccac    60
ttttccagtt cctgaaaccc taggggtga  ggggcaattg gtggtggtgg tggggggggg   120
gaatctgcta tttccgagaa ggctgggcct ccttcattaa caagctaatg gctgatttca   180
ctgagacctt gacatggatg caggtcgaaa ggcctnnnnn agatcggaag agcggttcag   240
caggaatgcc gagaccgatc tcgtatgccg tcttctgctt g                       281

<210> SEQ ID NO 104
<211> LENGTH: 60
<212> TYPE: DNA
<213> ORGANISM: Artificial Sequence
<220> FEATURE:
```

<223> OTHER INFORMATION: Synthetic Polynucleotide

<400> SEQUENCE: 104
tggaaaggac gaaacaccgg gggtgagggg caattgggtt aagagctat gctggaaaca    60

<210> SEQ ID NO 105
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 105
ggaaaggacg aaacaccgcc ctcaccccct agggtttcgt ttaagagcta tgctggaaac    60

<210> SEQ ID NO 106
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 106
acgcccagtc tctctactcc cc                                              22

<210> SEQ ID NO 107
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 107
tgtcaaggtc tcagtgaaat cagcca                                          26

<210> SEQ ID NO 108
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 108
cgaaaggatg ggagtactaa gctacgccca gtctctctac tcccc                    45

<210> SEQ ID NO 109
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 109
ggcctttcga cctgcatcca tgtcaaggtc tcagtgaaat cagcca                   46

<210> SEQ ID NO 110
<211> LENGTH: 88
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (59)..(63)
<223> OTHER INFORMATION: n is a, c, g, or t

<400> SEQUENCE: 110

```
aatgatacgg cgaccaccga gatctacact ctttccctac acgacgctct tccgatctnn      60
nnngccgaaa ggatgggagt actaagct                                         88
```

<210> SEQ ID NO 111
<211> LENGTH: 345
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (280)..(284)
<223> OTHER INFORMATION: n is a, c, g, or t

<400> SEQUENCE: 111

```
ccaaatgggc caagcaaaac acagccagtg agacaggcct gcacccggaa tgctaaccat      60
caagagtgga ttccgggaga ggggcaacct ggttcaacca gcgactcaca gatgagactg     120
tgagcccttt gtaaggaagg actgtctgta gactgaatgc gagctgagct cacgtgtcac     180
tggccacaga ggtccagccc agtctgtgga tgcagtggag tccaggaagg gctttctctg     240
gcttttgtag tgggaccgtg gatgcaggtc gaaaggcctn nnnnagatcg gaagagcggt     300
tcagcaggaa tgccgagacc gatctcgtat gccgtcttct gcttg                     345
```

<210> SEQ ID NO 112
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 112

```
ggaaaggacg aaacaccgat ggttagcatt ccgggtgcgt ttaagagcta tgctggaaac      60
```

<210> SEQ ID NO 113
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 113

```
ggaaaggacg aaacaccgac tgcatccaca gactgggcgt ttaagagcta tgctggaaac      60
```

<210> SEQ ID NO 114
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 114

```
ccaaatgggc caagcaaaac acag                                             24
```

<210> SEQ ID NO 115
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 115

```
cggtcccact acaaaagcca gagaa                                            25
```

<210> SEQ ID NO 116
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 116
cgaaaggatg ggagtactaa gctccaaatg ggccaagcaa aacacag            47

<210> SEQ ID NO 117
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 117
ggcctttcga cctgcatcca cggtcccact acaaaagcca gagaa              45

<210> SEQ ID NO 118
<211> LENGTH: 407
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (59)..(63)
<223> OTHER INFORMATION: n is a, c, g, or t
<220> FEATURE:
<221> NAME/KEY: misc_feature
<222> LOCATION: (342)..(346)
<223> OTHER INFORMATION: n is a, c, g, or t

<400> SEQUENCE: 118
aatgatacgg cgaccaccga gatctacact ctttccctac acgacgctct tccgatctnn    60
nnngccgaaa ggatgggagt actaagcagc ggggtggtag ctcacaagac caggtaggac   120
ggatatggct tgcgcaggc aattagtttc taagagctct cattcagtga atgtgaacag    180
tgccttttac aaaagatgct tgggtgaaag gacagaggaa ggtcgagggg gtgtggcttt   240
gagcaggcaa ttggctcccc agagctcaga ttttatgaat gtgaacagta ccctttttaaa  300 aagaggctag ggtgtaggca tggatgcagg tcgaaaggcc tnnnnnagat cggaagagcg   360
gttcagcagg aatgccgaga ccgatctcgt atgccgtctt ctgcttg                 407

<210> SEQ ID NO 119
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 119
tggaaaggac gaaacaccgt ggctttgagc aggcaatgtt taagagctat gctggaaaca    60

<210> SEQ ID NO 120
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 120
tggaaaggac gaaacaccgg acggatatgg ctttgcgcgt taagagcta tgctggaaac     60

<210> SEQ ID NO 121
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 121
tgcctacacc ctagcctctt tt                                              22

<210> SEQ ID NO 122
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 122
ggcctttcga cctgcatcca tgcctacacc ctagcctctt tt                        42

<210> SEQ ID NO 123
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 123
cgaaaggatg ggagtactaa gcttggtagc tcacaagacc aggt                      44

<210> SEQ ID NO 124
<211> LENGTH: 656
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (59)..(63)
<223> OTHER INFORMATION: n is a, c, g, or t
<220> FEATURE:
<221> NAME/KEY: misc_feature
<222> LOCATION: (591)..(595)
<223> OTHER INFORMATION: n is a, c, g, or t

<400> SEQUENCE: 124
aatgatacgg cgaccaccga gatctacact ctttccctac acgacgctct tccgatctnn     60
nnngccgaaa ggatgggagt actaagctgg tgctcagaca tacatgaagg caaaatgtca    120
tatacttaaa aaaaaaaaat gaagacatag ctcagtggct actcctccag aggaccctgg    180
tacccacatg gcagctctaa acaccagttc caggggatcc aataccctca catgcagaca    240
aaaccaatgc acataaaata aaaactaaaa cactagaaag tattccaagt gtgacccctc    300
aatacctagc ctcttttcca tgtcctctac ctttgctatt ccacctacat cttcggggag    360
aagagacaga agggccacgc tagacacata aaatcccatt ttctaggcct caaaatccag    420
ataggaacat cttgtaactt ctagagactt tttctcgtga aaggagctca gagcagaccc    480
acctttacaa ggagagccaa ccttacccct ctgagtgctc tgaggctcca gtctgaagag    540
cctgctccct aatctctgca tcttctggtt ggatgcaggt cgaaaggcct nnnnnagatc    600
ggaagagcgg ttcagcagga atgccgagac cgatctcgta tgccgtcttc tgcttg        656

<210> SEQ ID NO 125

```
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 125
tggaaaggac gaaacaccgc actcagaagg gtaaggtgtt taagagctat gctggaaaca    60

<210> SEQ ID NO 126
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 126
tggaaaggac gaaacaccgg gtaccagggt cctctgggtt taagagctat gctggaaaca    60

<210> SEQ ID NO 127
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 127
tggtgctcag acatacatga aggca                                          25

<210> SEQ ID NO 128
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 128 accagaaagat gcagagatta gggagc                                        26

<210> SEQ ID NO 129
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 129
cgaaaggatg ggagtactaa gctggtgctc agacatacat gaaggca                  47

<210> SEQ ID NO 130
<211> LENGTH: 105
<212> TYPE: DNA
<213> ORGANISM: Artificial Sequence
<220> FEATURE:
<223> OTHER INFORMATION: Synthetic Polynucleotide

<400> SEQUENCE: 130
ggcctttcga cctgcatcca ccagaaagatg cagagattag ggagcctctt tccctacacg    60
acgctcttcc gatctaactc gccgaaagga tgggagtact aagct                   105

<210> SEQ ID NO 131
<211> LENGTH: 60
<212> TYPE: DNA
<213> ORGANISM: Artificial Sequence
<220> FEATURE:
<223> OTHER INFORMATION: Synthetic Polynucleotide
```

<400> SEQUENCE: 131
ctctttccct acacgacgct cttccgatct ctggagccga aaggatggga gtactaagct    60

<210> SEQ ID NO 132
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 132
ctctttccct acacgacgct cttccgatct ggactgccga aaggatggga gtactaagct    60

<210> SEQ ID NO 133
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 133
ctctttccct acacgacgct cttccgatct tctgcgccga aaggatggga gtactaagct    60

<210> SEQ ID NO 134
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 134
ctctttccct acacgacgct cttccgatct aaccggccga aaggatggga gtactaagct    60

<210> SEQ ID NO 135
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 135
ctctttccct acacgacgct cttccgatct ctctggccga aaggatggga gtactaagct    60

<210> SEQ ID NO 136
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 136
ctctttccct acacgacgct cttccgatct ggtaagccga aaggatggga gtactaagct    60

<210> SEQ ID NO 137
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 137
ctctttccct acacgacgct cttccgatct aagctgccga aaggatggga gtactaagct    60

<210> SEQ ID NO 138

```
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 138
ctctttccct acacgacgct cttccgatct tcgtcgccga aaggatggga gtactaagct      60

<210> SEQ ID NO 139
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 139
ctctttccct acacgacgct cttccgatct ccaatgccga aaggatggga gtactaagct      60

<210> SEQ ID NO 140
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 140
ctctttccct acacgacgct cttccgatct gcgtagccga aaggatggga gtactaagct      60

<210> SEQ ID NO 141
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 141
ctctttccct acacgacgct cttccgatct tgagcgccga aaggatggga gtactaagct      60

<210> SEQ ID NO 142
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 142
cattcctgct gaaccgctct tccgatctac atcaggcctt tcgacctgca tcca            54

<210> SEQ ID NO 143
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 143
cattcctgct gaaccgctct tccgatctgc ctaaggcctt tcgacctgca tcca            54

<210> SEQ ID NO 144
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 144
```
cattcctgct gaaccgctct tccgatcttg gtcaggcctt tcgacctgca tcca       54

<210> SEQ ID NO 145
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 145
cattcctgct gaaccgctct tccgatctca ctgaggcctt tcgacctgca tcca       54

<210> SEQ ID NO 146
<211> LENGTH: 491
<212> TYPE: DNA
<213> ORGANISM: Mus musculus

<400> SEQUENCE: 146
tcctggtaaa taactgagcc ctgaaattgc ttgcttactc tgtgaatgct tccacaatgt    60
tttcccagaa tcccacccct gaaccttcgt gtgtactgag cccctctctc aggacttgtc   120
cacactggct gcagcaaaca tctgtagctt ggcgtctgct gactcctgat gtgagaaatt   180
cgtatttggt tgtttggatt tgcatgtttc gctgtgttac tggtatctgt attcagtttc   240
ctaagcccta gctggagggt ctgactgtgc cctagaactg gcttctttgg tcctttgctc   300
tggaaagtcc ttccgggcac ctttcctccc aaagctggct tccagctgtg gccttgaact   360
ggaaagcgca gagagataac gactgctcca ccccagagtt gatctttact aacactggat   420
tgtaaactgc ttatttttt gtctttcacc ccactccccc tggttcccaa tgggaggtct   480
aagcctgctc t                                                        491

<210> SEQ ID NO 147
<211> LENGTH: 426
<212> TYPE: DNA
<213> ORGANISM: Artificial Sequence
<220> FEATURE:
<223> OTHER INFORMATION: Synthetic Polynucleotide

<400> SEQUENCE: 147
tcctggtaaa taactgagcc ctgaaattgc ttgcttactc tgtgaatgct tccacaacac    60
tggctgcagc aaacatctgt agcttggcgt ctgctgactc tgatgtgag aaattcgtat   120
ttggttgttt ggatttgcat gtttcgctgt gttactggta tctgtattca gtttcctaag   180
ccctagctgg agggtctgac tgtgccctag aactggcttc tttggtcctt tgctctggaa   240
agtccttccg ggcacctttc ctcccaaagc tggcttccag ctgtggcctt gaactggaaa   300
gcgcagagag ataacgactg ctccacccca gagttgatct ttactaacac tggattgtaa   360
actgcttatt ttttgtctt tcaccccact cccctggtt cccaatggga ggtctaagcc   420
tgctct                                                              426

<210> SEQ ID NO 148
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 148
ggaaaggacg aaacaccgtt tgctgcagcc agtgttggtt taagagctat gctggaaaca    60

<210> SEQ ID NO 149
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 149
tcctggtaaa taactgagcc ctgaaat        27

<210> SEQ ID NO 150
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 150
agagcaggct tagacctccc a        21

<210> SEQ ID NO 151
<211> LENGTH: 403
<212> TYPE: DNA
<213> ORGANISM: Mus musculus

<400> SEQUENCE: 151 cccctt ggat gtgagaacct cagggttcca aggactctct tctgggagtc tgcccaactg        60
caaaaggcta ggtggctgac acttggagat gggggtggga gcagatgcca cagtcttttg        120
acatgcccac caaaaggcca tttggaaata aagctgcttt ggttgccagc agagctcttg        180
tctcagaggg gaccctggca gatggcggcg cgcctgttat cacgggcata tccctgctga        240
tgttcttcct tcttcgaaat agagcgttta ttcagctcca atttgttacc atgggttgtc        300
ccaaaatgat gaaggaaaat tcaagagact gccagggcc agttggattt gaaacatttg        360
tattcagcac agcagatgct ctcggctaca gagaacagct ttt        403

<210> SEQ ID NO 152
<211> LENGTH: 314
<212> TYPE: DNA
<213> ORGANISM: Artificial Sequence
<220> FEATURE:
<223> OTHER INFORMATION: Synthetic Polynucleotide

<400> SEQUENCE: 152 cccctt ggat gtgagaacct cagggttcca aggactctct tctgggagtc tgcccaactg        60
caaaaggcta ggtggctgac acttggagat gggggtggga gcagatgcca cagtcttttg        120
acatgcccac caaaaggcca tttggaaata aagctgcttt ggttgccagc agagctcttg        180
tctcagaggg gaccctggca gatggcggcg cgcctgttat tgaaggaaaa ttcaagagac        240
tgccaggggc cagttggatt tgaaacattt gtattcagca cagcagatgc tctcggctac        300
agagaacagc tttt        314

<210> SEQ ID NO 153
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 153
tggaaaggac gaaacaccgg cggcgcgcct gttatcacgt ttaagagcta tgctggaaac        60

<210> SEQ ID NO 154
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 154
tggaaaggac gaaacaccgg gttgtcccaa aatgatgagt ttaagagcta tgctggaaac      60

<210> SEQ ID NO 155
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 155
ggaaaggacg aaacaccgtt gaattttcct tcaataacgt ttaagagcta tgctggaaac      60

<210> SEQ ID NO 156
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 156
ccccttggat gtgagaacct c                                                21

<210> SEQ ID NO 157
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 157
aaaagctgtt ctctgtagcc gagag                                            25

<210> SEQ ID NO 158
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 158
ttgatggcaa caatctccac                                                  20

<210> SEQ ID NO 159
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 159
cgtcccgtag acaaaatggt                                                  20

<210> SEQ ID NO 160
<211> LENGTH: 19
<212> TYPE: DNA
<213> ORGANISM: Artificial Sequence
<220> FEATURE:

<223> OTHER INFORMATION: Synthetic Polynucleotide

<400> SEQUENCE: 160
atggagggga atacagccc                                                   19

<210> SEQ ID NO 161
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 161
ttctttgcag ctccttcgtt                                                  20

<210> SEQ ID NO 162
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 162
cctccaacgt ttttacgagc                                                  20

<210> SEQ ID NO 163
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 163
ggtccaaatt caaacgcact                                                  20

<210> SEQ ID NO 164
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 164
ttttacgagc cgtcgaagat                                                  20

<210> SEQ ID NO 165
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 165
tctgatggca aggtctctcc                                                  20

<210> SEQ ID NO 166
<211> LENGTH: 807
<212> TYPE: DNA
<213> ORGANISM: Mus musculus

<400> SEQUENCE: 166
atgtgggtcc cagtagtcat attccacctg gtgcctctgg cctccgagtc atctgactgg      60
cccttagtga actttgtggt tagtcatgtt gtgtgcacag tcaggaacta gagagaaggc     120
tagtattcct agtgacttag tgtccgggat gttgccactg ccactcacag tcagaatagg     180

-continued

```
gcttttctac tcagttaaac actctcacag atacccagc agagccttcc ttaggggatt      240
ctaaatccag tcaaattcac agtgaagatg aaccctccag tgctccgtag ctggggctgc      300
tgcgtagcac atttgcacac cgtgaggacc atcagtagcc caggttggcc ggagttttag      360
cctgcagatg tgaggccaca agccaggagc ccttgccgct tgctctccca ccagcgagaa      420
ccatttagta atgtccatgg agatggaagg cggtgtttat aacattcatt cttctctaca      480
tacatcgtga agggagggag gtcaggtgag ggacatcagg gattttcctg gaagaaagct      540
ttgctgggcg ttcatgtgac tcatgttcca gtaagagccg cagtctcgga tgacctgagt      600
agagcagggt tatctggatg tgcttgtggg tggaacccct tggaaggga ggtaggtaag       660 ggtgggtgta tcctcgcaga gacgtagaac ttctgtgtgt ggatgatgtt tcatcagaga      720
ctgtgagccg agccggatgc taaacacagt agttctcaac cttcctaatg ctacaaccct      780
catgctgtgg tgaccccag ccataca                                            807
```

<210> SEQ ID NO 167
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 167

```
ggaaaggacg aaacaccgct ctgctggggt atctgtgagt ttaagagcta tgctggaaac      60
```

<210> SEQ ID NO 168
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 168

```
tggaaaggac gaaacaccga tttagaatcc cctaaggagt ttaagagcta tgctggaaac      60
```

<210> SEQ ID NO 169
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 169

```
ggaaaggacg aaacaccgtc cgagactgcg gctcttacgt ttaagagcta tgctggaaac      60
```

<210> SEQ ID NO 170
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 170

```
ggaaaggacg aaacaccgtc ggatgacctg agtagagcgt ttaagagcta tgctggaaac      60
```

<210> SEQ ID NO 171
<211> LENGTH: 23
<212> TYPE: DNA
<213> ORGANISM: Artificial Sequence
<220> FEATURE:
<223> OTHER INFORMATION: Synthetic Polynucleotide

```
<400> SEQUENCE: 171
cctctggcct ccgagtcatc tga                                           23

<210> SEQ ID NO 172
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 172
tcatccacac acagaagttc tacgt                                         25

<210> SEQ ID NO 173
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(12)
<223> OTHER INFORMATION: where n is A, G, T, or C
<220> FEATURE:
<221> NAME/KEY: misc_feature
<222> LOCATION: (13)..(14)
<223> OTHER INFORMATION: where n is anything
<220> FEATURE:
<221> NAME/KEY: misc_feature
<222> LOCATION: (19)..(19)
<223> OTHER INFORMATION: where n is A or T

<400> SEQUENCE: 173
nnnnnnnnnn nnnnagaan                                                19

<210> SEQ ID NO 174
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(11)
<223> OTHER INFORMATION: where n is A, G, T, or C
<220> FEATURE:
<221> NAME/KEY: misc_feature
<222> LOCATION: (12)..(13)
<223> OTHER INFORMATION: where n is anything
<220> FEATURE:
<221> NAME/KEY: misc_feature
<222> LOCATION: (18)..(18)
<223> OTHER INFORMATION: where n is A or T

<400> SEQUENCE: 174
nnnnnnnnnn nnnagaaw                                                 18

<210> SEQ ID NO 175
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 175
tggtagctca caagaccagg t                                             21

<210> SEQ ID NO 176
<211> LENGTH: 45
```

```
<212> TYPE: DNA
<213> ORGANISM: Artificial Sequence
<220> FEATURE:
<223> OTHER INFORMATION: Synthetic Polynucleotide

<400> SEQUENCE: 176
ggcctttcga cctgcatcca ccagaagatg cagagattag ggagc            45
```